United States Patent
Kennedy et al.

(10) Patent No.: US 10,822,380 B2
(45) Date of Patent: Nov. 3, 2020

(54) DISRUPTION OF THE WAVE3 PROTEIN COMPLEX FOR SUPPRESSION OF INVASION AND METASTASIS

(71) Applicants: UNIVERSITY OF GEORGIA RESEARCH FOUNDATION, INC., Athens, GA (US); AUGUSTA UNIVERSITY RESEARCH INSTITUTE, INC., Augusta, GA (US)

(72) Inventors: Eileen J. Kennedy, Athens, GA (US); John Cowell, Augusta, GA (US)

(73) Assignees: University of Georgia Research Foundation, Inc., Athens, GA (US); Augusta University Research Institute, Inc., Augusta, GA (US)

( * ) Notice: Subject to any disclaimer, the term of this patent is extended or adjusted under 35 U.S.C. 154(b) by 159 days.

(21) Appl. No.: 15/565,229

(22) PCT Filed: Apr. 8, 2016

(86) PCT No.: PCT/US2016/026713
§ 371 (c)(1),
(2) Date: Oct. 9, 2017

(87) PCT Pub. No.: WO2016/164768
PCT Pub. Date: Oct. 13, 2016

(65) Prior Publication Data
US 2018/0072782 A1  Mar. 15, 2018

Related U.S. Application Data

(60) Provisional application No. 62/144,631, filed on Apr. 8, 2015.

(51) Int. Cl.
| | | |
|---|---|---|
| *C07K 14/47* | (2006.01) | |
| *A61K 38/08* | (2019.01) | |
| *A61K 38/18* | (2006.01) | |
| *A61K 38/00* | (2006.01) | |

(52) U.S. Cl.
CPC .............. *C07K 14/47* (2013.01); *A61K 38/08* (2013.01); *A61K 38/18* (2013.01); *A61K 38/00* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2014/0296160 A1  10/2014  Walensky et al.

FOREIGN PATENT DOCUMENTS

| WO | 0061627 A1 | 10/2000 |
|---|---|---|
| WO | 2011053636 A1 | 5/2011 |
| WO | 2015010048 A1 | 1/2015 |

OTHER PUBLICATIONS

Tame (J. Comput. Aided Mol. Des. Mar. 1999; 13 (2): 99-108).*
Dixon (Proteins. 1997; Suppl 1: 198-204).*
Lensink et al (Proteins. 2007; 69: 704-718).*
Fulton et al (BMC, 26(6):1167-1173, 2018, pp. 1-15).*
Ali et al (CSBJ, 17,263-281, 2019).*
Chen, Z. et al., Structure and Control of the Actin Regulatory WAVE Complex. Nature., Nov. 25, 2010, vol. 468, No. 7323, pp. 533-538.
Teng, Y. et al., Targeting the WASF3 CYFIP1 Complex Using Stapled Peptides Suppresses Cancer Cell Invasion. Cancer research (2015); canres-1680.
International Search Report & Written Opinion issued in corresponding application No. PCT/US2016/026713, dated Jul. 22, 2016, 9 pgs.
Supplementary European Search Report issued in corresponding Application No. EP 16777386.0, dated Sep. 17, 2018, 14 pages.
Lane, J. et al. "Structure and role of WASP and WAVE in Rho GTPase signaling in cancer", Cancer genomics & proteomics, May 1, 2014 (May 1, 2014), p. 155.
Machesky, L. et al., "Actin-Based Protrusions: Promoters or Inhibitors of Cancer Invasion?", Cancer Cell, vol. 16, No. 1, Jul. 1, 2009 (Jul. 1, 2009), pp. 5-7.
Silva, J. et al., Cyfip1 is a Putative Invasion Suppressor in Epithelial Cancers:, CELL, vol. 137, No. 6, 2009, pp. 1047-1061.
Sowell, J. et al., "Suppression of Breast Cancer Metastasis Using Stapled Peptides Targeting the WASF Regulatory Complex", Cancer Growth and Metastasis 2017, vol. 10, 2017, pp. 1-9.
Teng, Y. et al., "The WASF-3-NCKAP1-CYFIP1 Complex is Essential for Breast Cancer Metastasis", Cancer Research, vol. 76, No. 17, Jul. 18, 2016 (Jul. 18, 2016), pp. 5133-5142.
Di Marino, D. et al. "MD and Docking Studies Reveal That the Functional Switch of CYFIP1 is Mediated by a Butterfly-like Motion", Journal of chemical theory and computation: JCTC, vol. 11, No. 7, Jul. 14, 2015 (Jul. 14, 2015), pp. 3401-3410.
Innocenti, M. et al., et al: "Abi1 is essential for the formation and activation of a WAVE2 signalling complex", Nature Cell Biology, vol. 6, No. 4, Apr. 1, 2004 (Apr. 1, 2004), pp. 319-327.
Weiner, O. et al., "Hem-1 Complexes Are Essential for Rac Activation, Actin Polymerization, and Myosin Regulation during Neutrophil Chemotaxis", PLoS Biology, vol. 4, No. 2, Jan. 24, 2006 (Jan. 24, 2006), p. e38.

(Continued)

*Primary Examiner* — Brad Duffy
(74) *Attorney, Agent, or Firm* — Meunier Carlin & Curfman LLC

(57) ABSTRACT

As disclosed herein, stapled peptides targeting the interaction interface between proteins that maintain the integrity of Wiskott-Aldrich syndrome protein family member 3 (WASF3) leads to destabilization of WASF3 and suppression of invasion. Disclosed are stapled peptides that inhibit the binding of Cytoplasmic FMR1-interacting protein 1 (CYFIP1) to either WASF3 or NCK-associated protein (NCKAP1). Also disclosed are methods for treating or suppressing invasion and metastasis of a cancer in a subject that involve administering to the subject a therapeutically effective amount of a stapled peptide disclosed herein.

1 Claim, 33 Drawing Sheets

Specification includes a Sequence Listing.

(56) References Cited

OTHER PUBLICATIONS

Teng, Y. et al., "Critical role of the WASF3 gene in JAK2/STAT3 regulation of cancer cell motility", Carcinogenesis., vol. 34, No. 9, Jun. 17, 2013 (Jun. 17, 2013), pp. 1994-1999.
Communication pursuant to Article 94(3) EPC issued in corresponding EP application No. 16777386.0, dated Jun. 8, 2020, 9 pages.

* cited by examiner

| | |
|---|---|
| WASF1 | [26]LECVTNISLANIIRQL[41] |
| WASF2 | LECVTNITLANVIRQL |
| WASF3 | LECVTNSTLAAIIRQL |
| | |
| WAHM1 | LEK♦TNS♦LAKIIRQL |
| WAHM2 | LEKKTN♦TLA♦IIRQL |
| SCR1 | SRA♦LLI♦TKIQNELK |
| SCR2 | TRAILL♦ITK♦QNELK |

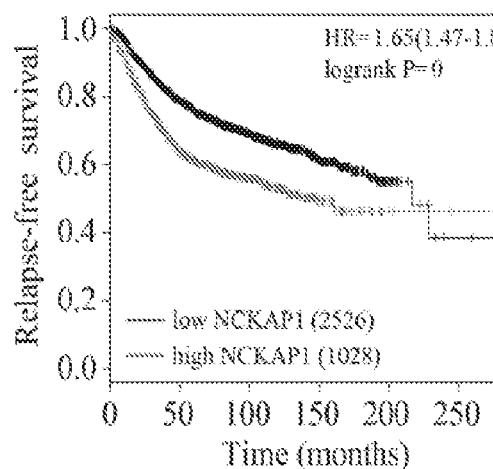
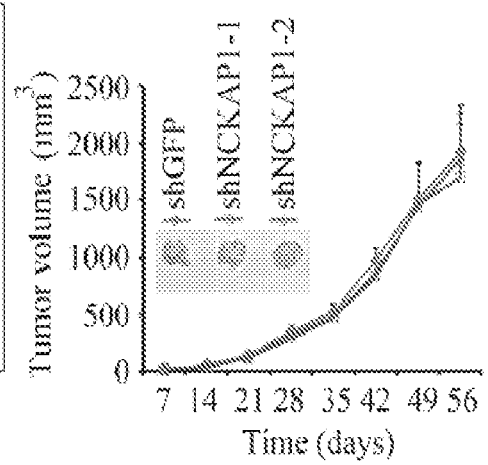
FIGURE 14A
FIGURE 14B
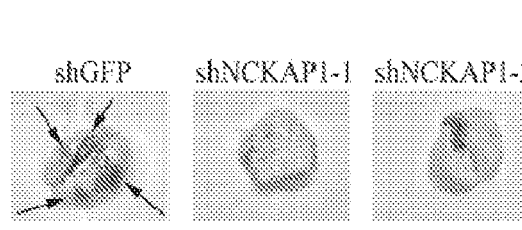
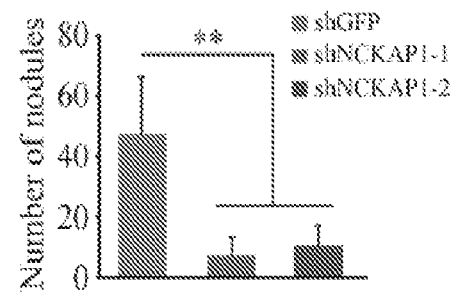
FIGURE 14C

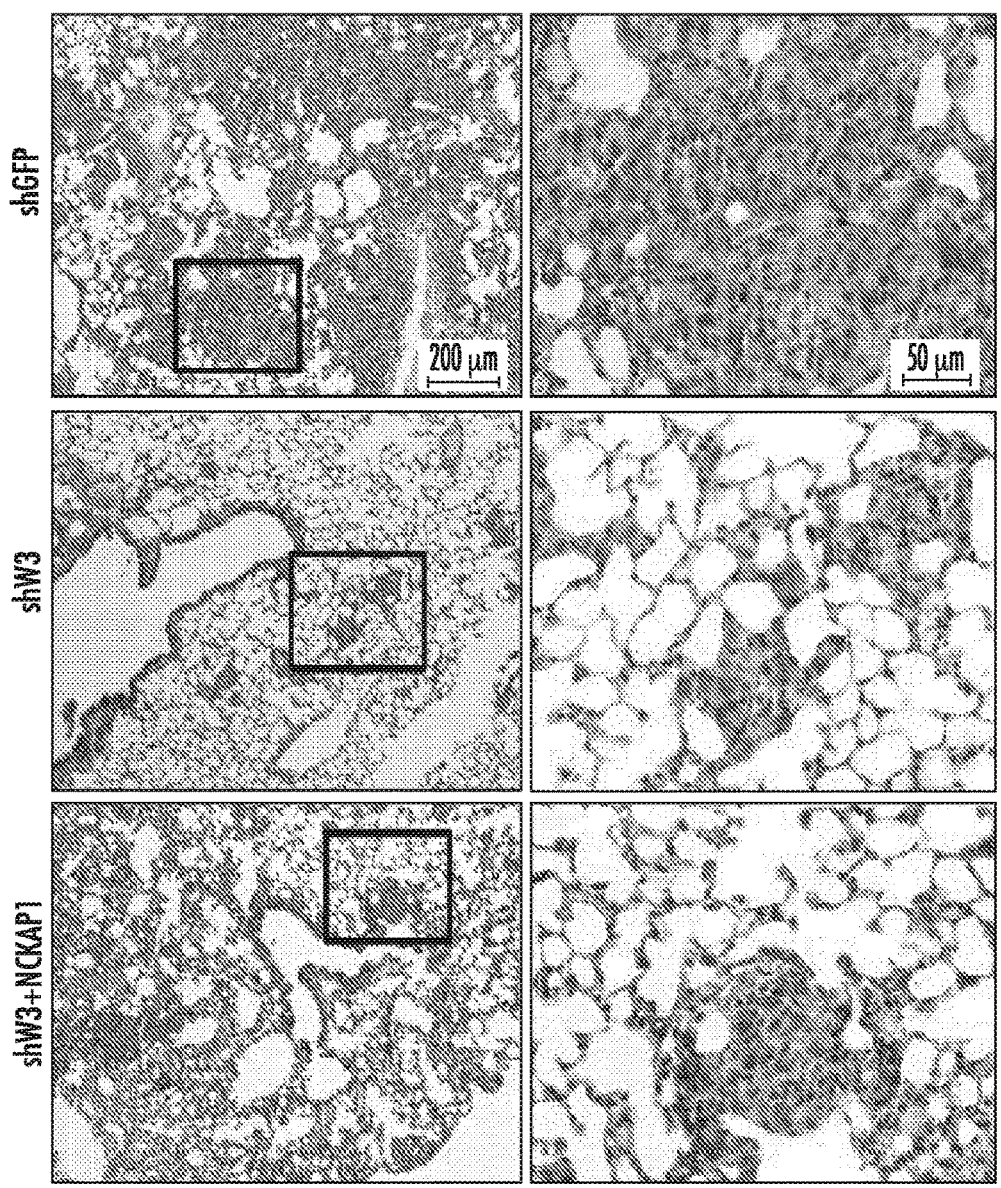
FIGURE 16D
631 KHCAKTISQAVN 642
933 PFLVSSIEDFKD 944
1110 VLLRNAYHAVYK 1121
WANT1      KHCA*TIS*AVNK
WANT2      EL*SSI*DFKDHK
WANT3      VL*RNA*HAVYK
WANT3 scr  HK*VYL*ANRAV
FIGURE 17A
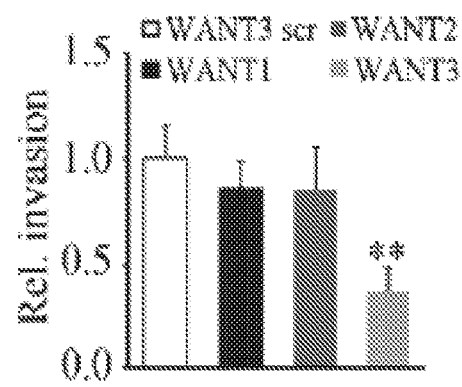
FIGURE 17B

DISRUPTION OF THE WAVE3 PROTEIN COMPLEX FOR SUPPRESSION OF INVASION AND METASTASIS

CROSS-REFERENCE TO RELATED APPLICATIONS

This application is a 371 U.S. National Stage of International Application No. PCT/US2016/026713, filed Apr. 8, 2016, which claims benefit of U.S. Provisional Application No. 62/144,631, filed Apr. 8, 2015, each of which are hereby incorporated herein by reference in their entireties.

STATEMENT REGARDING FEDERALLY SPONSORED RESEARCH OR DEVELOPMENT

This invention was made with Government Support under Grant No. CA120510 and Grant No. CA154600 awarded by the National Institutes of Health. The Government has certain rights in the invention.

BACKGROUND

Invasion and metastasis is the final stage of cancer progression and is responsible for >90% of all deaths due to cancer (Siegel, R., et al. CA Cancer J. Clin. 63:11-30 (2013); Krause, M., et al. Nat. Rev. Mol. Cell. Biol. 15:577-590 (2014)). Suppressing metastasis, therefore, could significantly impact the overall survival in cancer patients, but this strategy requires identifying a target that has regulatory control over metastasis.

SUMMARY

Inactivation of the Wiskott-Aldrich syndrome protein family member 3 (WASF3) metastasis-promoting gene leads to suppression of invasion and metastasis in a variety of different cancer cell types, suggesting that targeting its function could be a means of suppressing these phenotypes. The stability of the WASF3 protein is disclosed herein to rely on its interaction with Cytoplasmic FMR1-interacting protein 1 (CYFIP1) and NCK-associated protein (NCKAP1). Since these proteins interact via large, elongated binding surface that is largely mediated by alpha-helical structures, stapled peptides that target the protein-protein interface (PPI) between WASF3 and CYFIP1, or CYFIP1 and NCKAP1, were developed as a strategy to prevent invasion.

Disclosed are stapled peptides that inhibit the binding of CYFIP1 to either WASF3 or NCKAP1. In some cases, these peptides are capable of mimicking an alpha helix of CYFIP1 or an alpha helix of WASF3 in physiological conditions and thereby inhibit endogenous CYFIP1 from binding to endogenous WASF3, e.g. in an isoform-specific manner. In some cases, these peptides are capable of mimicking an alpha helix of CYFIP1 or an alpha helix of NCKAP1 in physiological conditions and thereby inhibit endogenous CYFIP1 from binding to endogenous NCKAP1.

Treatment of breast and prostate cancer cells with these stapled peptides led to suppression of WASF3 protein levels and reduced invasion. Therefore, also disclosed are methods for treating or suppressing invasion and metastasis of a cancer in a subject that involve administering to the subject a therapeutically effective amount of a stapled peptide disclosed herein.

The details of one or more embodiments of the invention are set forth in the accompanying drawings and the description below. Other features, objects, and advantages of the invention will be apparent from the description and drawings, and from the claims.

Figure 5A:
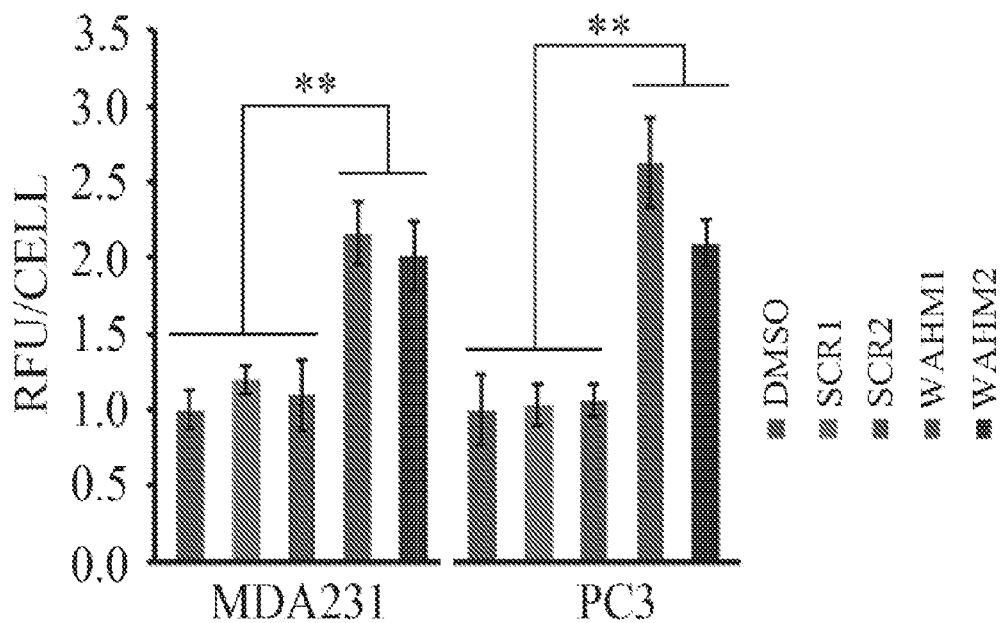
FIGS. 5A to 5C show WAHM peptides suppress cancer cell invasion. Fluorescence intensity of phalloidin stained cells demonstrates that MDA-MB-231 and PC3 cells treated with WAHM1/2 show increased intensity indicative of increased levels of stress fibers, in contrast to cells treated with either the DMSO vehicle or scrambled peptides (FIG.
Figure 5B:
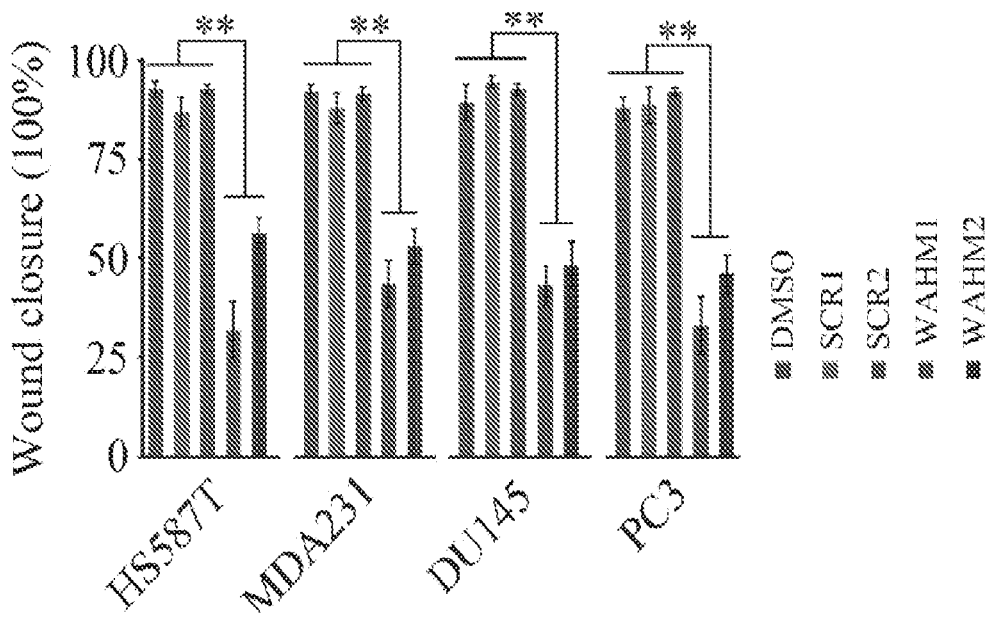

5A). When prostate and breast cancer cells were treated with WAHM1/2 there was a significant reduction in cell motility compared with DMSO and scrambled peptide treatment (FIG. 5B). Similarly, treatment with WAHM1/2 significantly suppresses invasion in breast and prostate cells (FIG. 5C). *p<0.05 and **p<0.01.

Figure 6A:
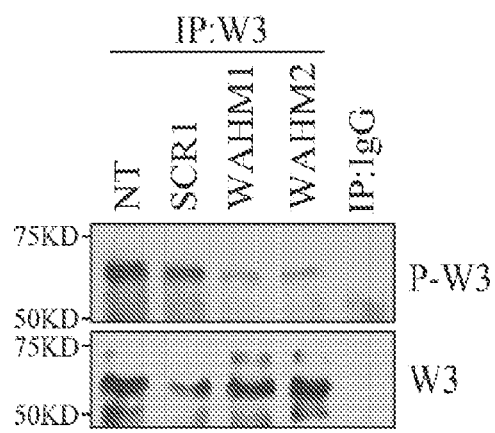
Figure 6B:
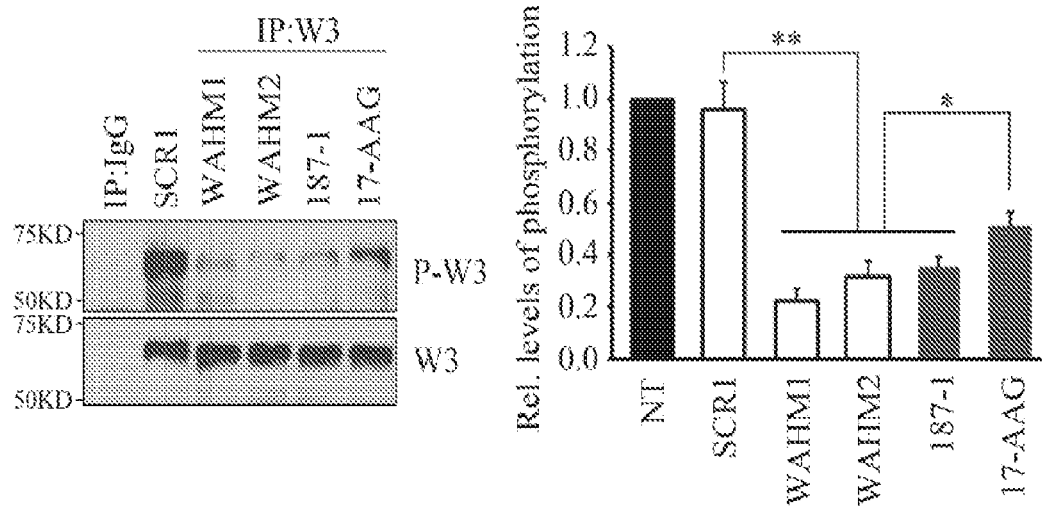
Figure 6C:
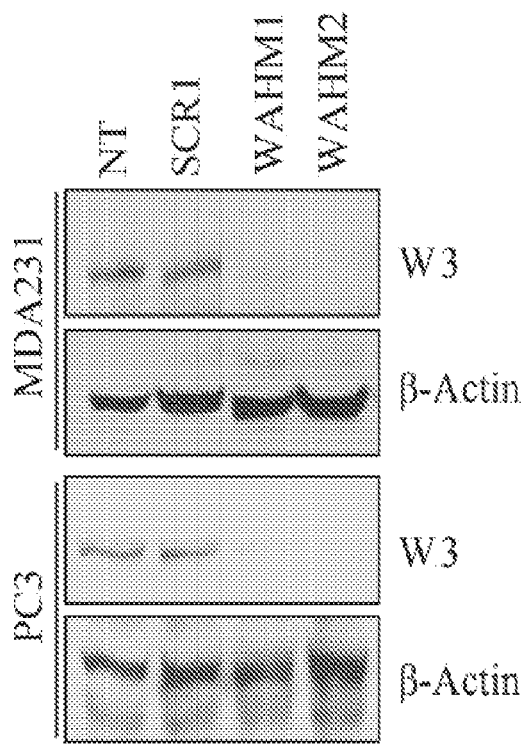
Figure 6D:
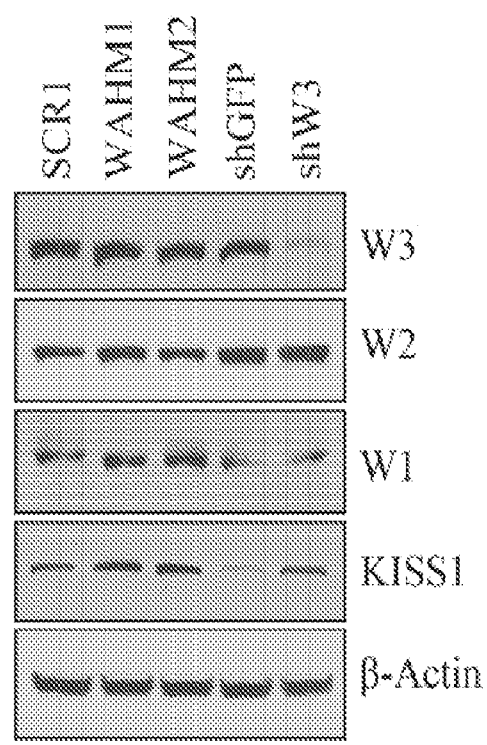

FIGS. 6A to 6E show WAHM peptides lead to loss of WASF3 phosphoactivation and suppression of downstream signaling. When MDA-MB-231 cells were treated with WAHM1/2, there was no reduction in WASF3 protein levels but, unlike cells treated with the scrambled control, there is a reduction in WASF3 phosphorylation (FIG. 6A). IgG IP was used as a negative control. When compared with the ability of HSP90 inhibitor 17-AAG to suppress WASF3 phosphorylation, WAHM1/2 proves to be more efficient (FIG. 6B). When MDA-MB-231 and PC3 cells were starved overnight and then treated with WAHM1/2, WASF3 levels reduced below detectable levels in contrast to untreated cells (NT) and cells treated with scrambled control peptides (SCR1) (FIG. 6C). Stapled peptides do not affect the protein levels of any of the WASF family members (FIG. 6D). Knockdown of WASF3 (shW3) leads to increased KISS1 protein levels compared with control shRNA treatment (shGFP). When cells are treated with WAHM1/2 KISS1 levels increase compared with treatment with the scrambled peptides, demonstrating the consequence on downstream signaling results in loss of WASF3 (FIG. 6D). This loss of signaling is supported by upregulation of MMP9 following treatment of MDA-MB-231 and PC3 cells with WAHM1/2 (FIG. 6E) which shows significantly reduced MMP9 levels, comparable to those seen in WASF3 knockdown cells (shW3). In contrast, cells treated with the scrambled peptide or control shRNA (shGFP) show no effect on MMP9 activity.

Figure 7:
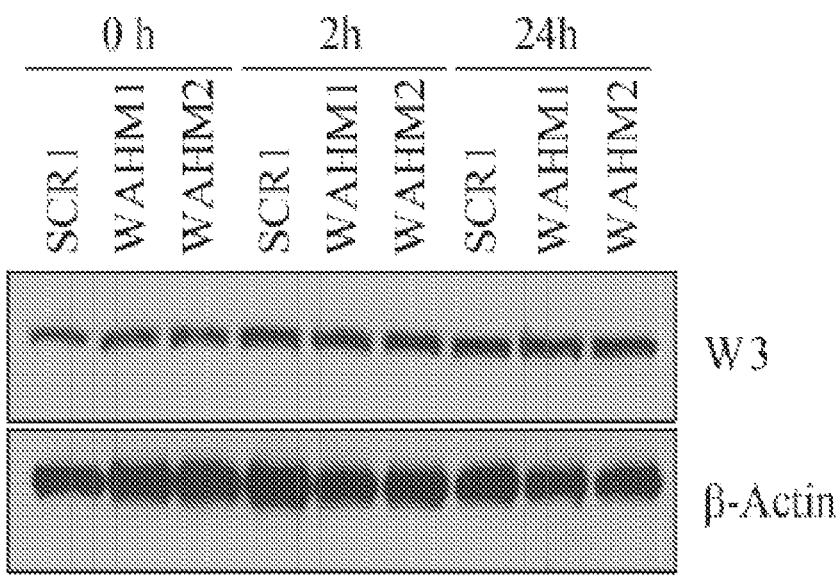

FIG. 7 shows an avidin-biotin pull down assays of MDA-MB-231 cells exposed to biotinylated WAHM1 and WAHM2 for 0, 2, and 24 hours.

Figure 8:
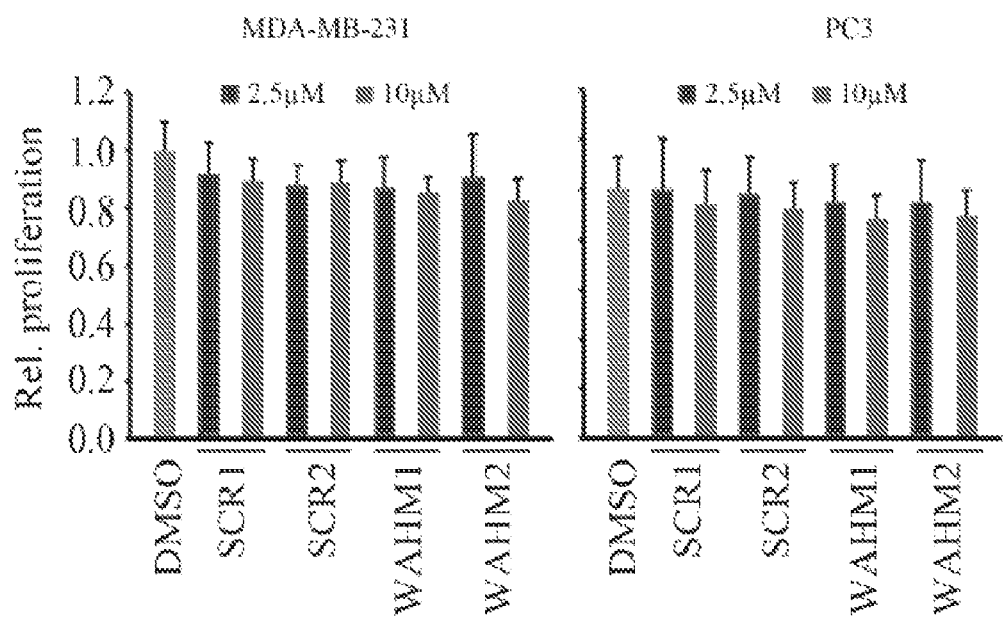

FIG. 8 shows relative proliferation (MTS assays) of MDA-MB-231 and PC3 cells treated with either WAHM1 or WAHM2, or the scrambled peptides at a 10 μM concentration over 24 hours.

Figure 9A:
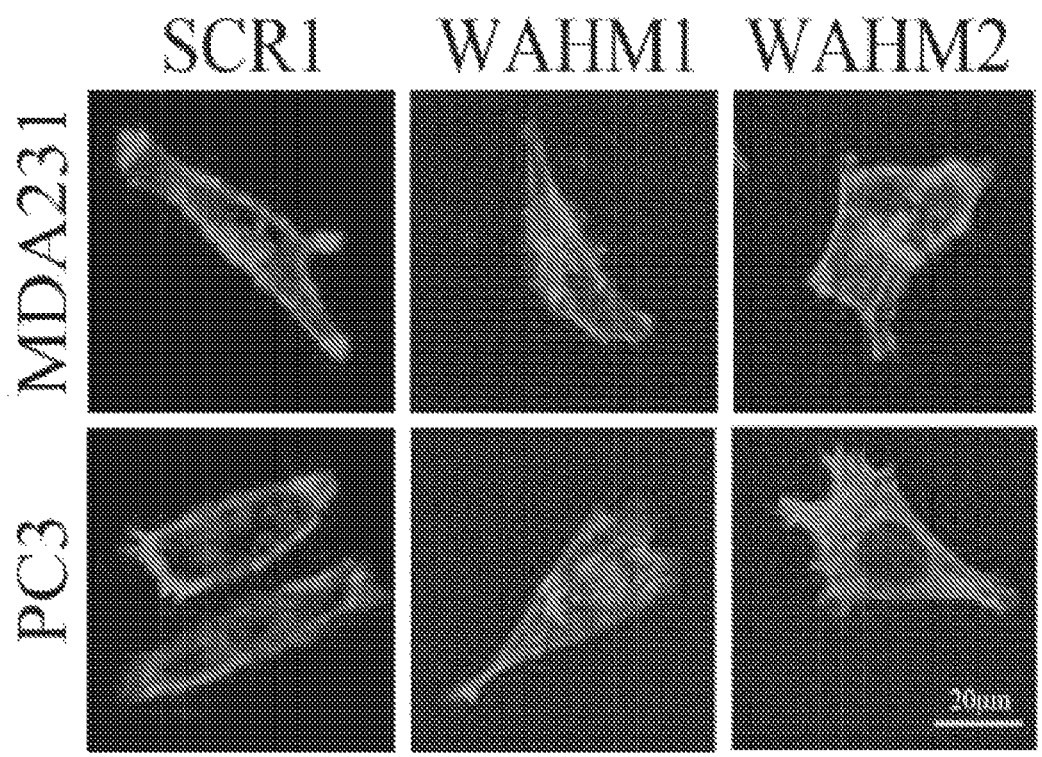
Figure 9B:
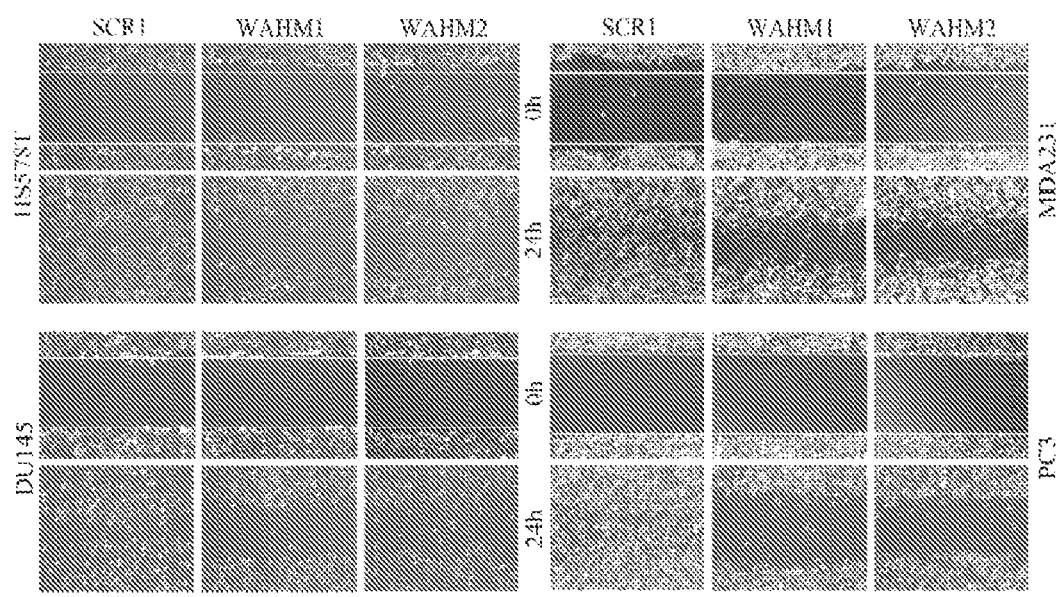
Figure 9C:
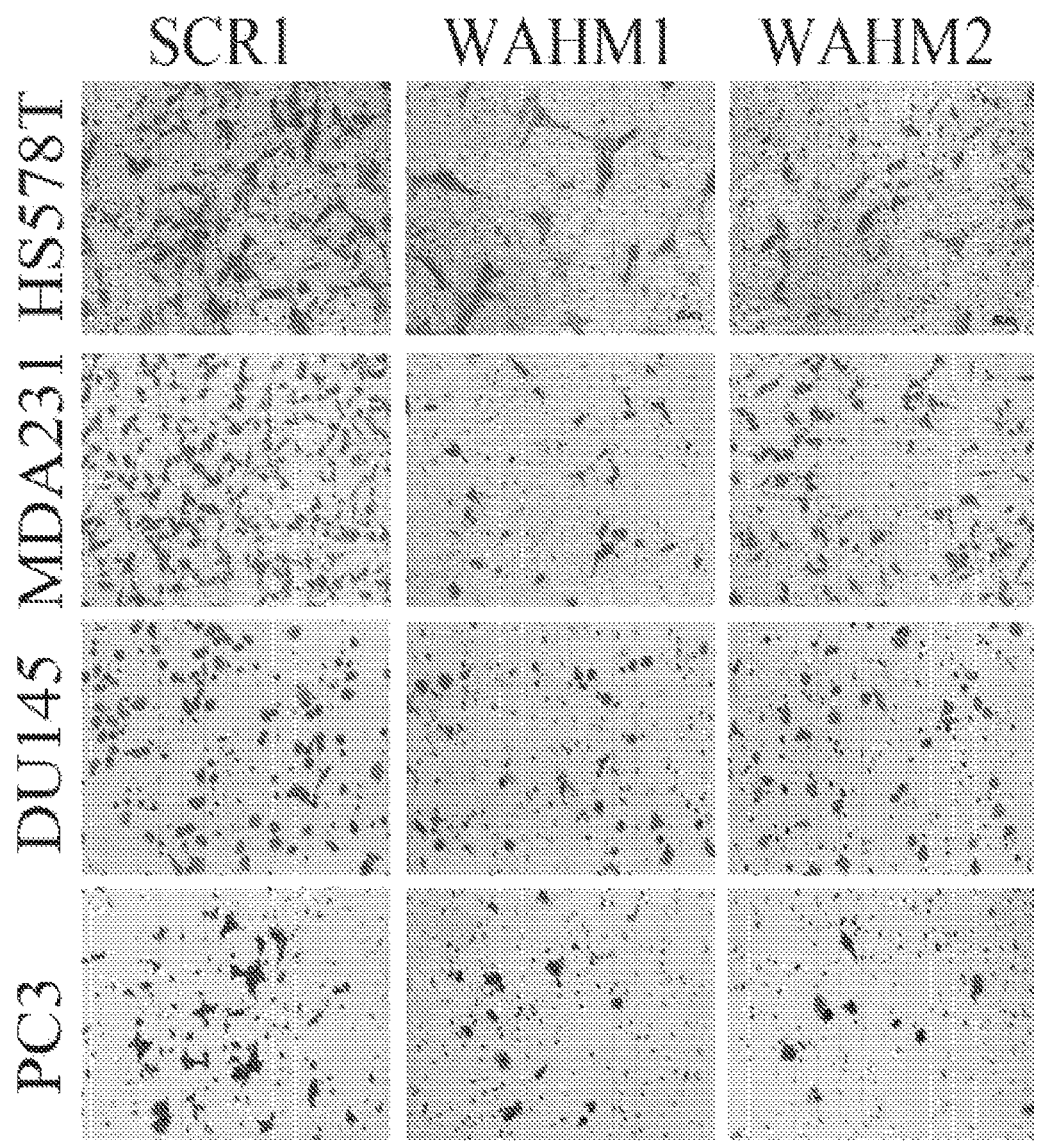

FIGS. 9A to 9C show MDA-MB-231 and PC3 cells stained for actin cytoskeleton (FIG. 9A), assayed with a scratch wound assay (FIG. 9B), or assayed with transwell invasion analysis (FIG. 9C) after treatment with either WAHM1 or WAHM2, or the scrambled peptides.

Figure 10:
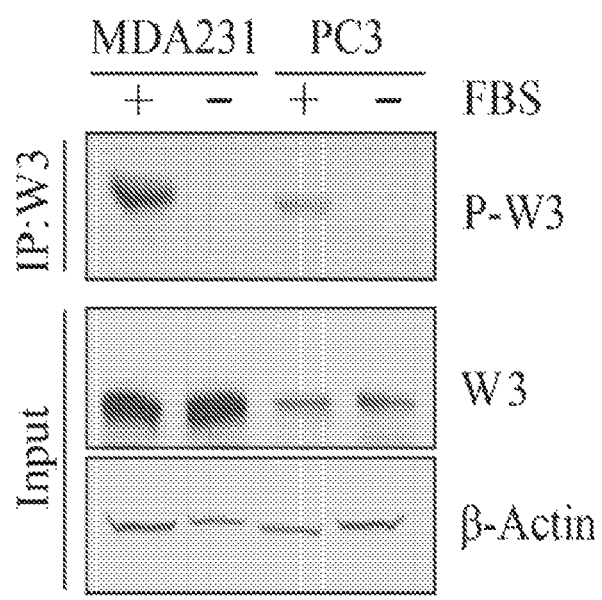

FIG. 10 shows activated WASF3 protein (IP:W3) in MDA-MB-231 and PC3 cells cultured in FBS (+) or serum starved (−).

Figure 11:
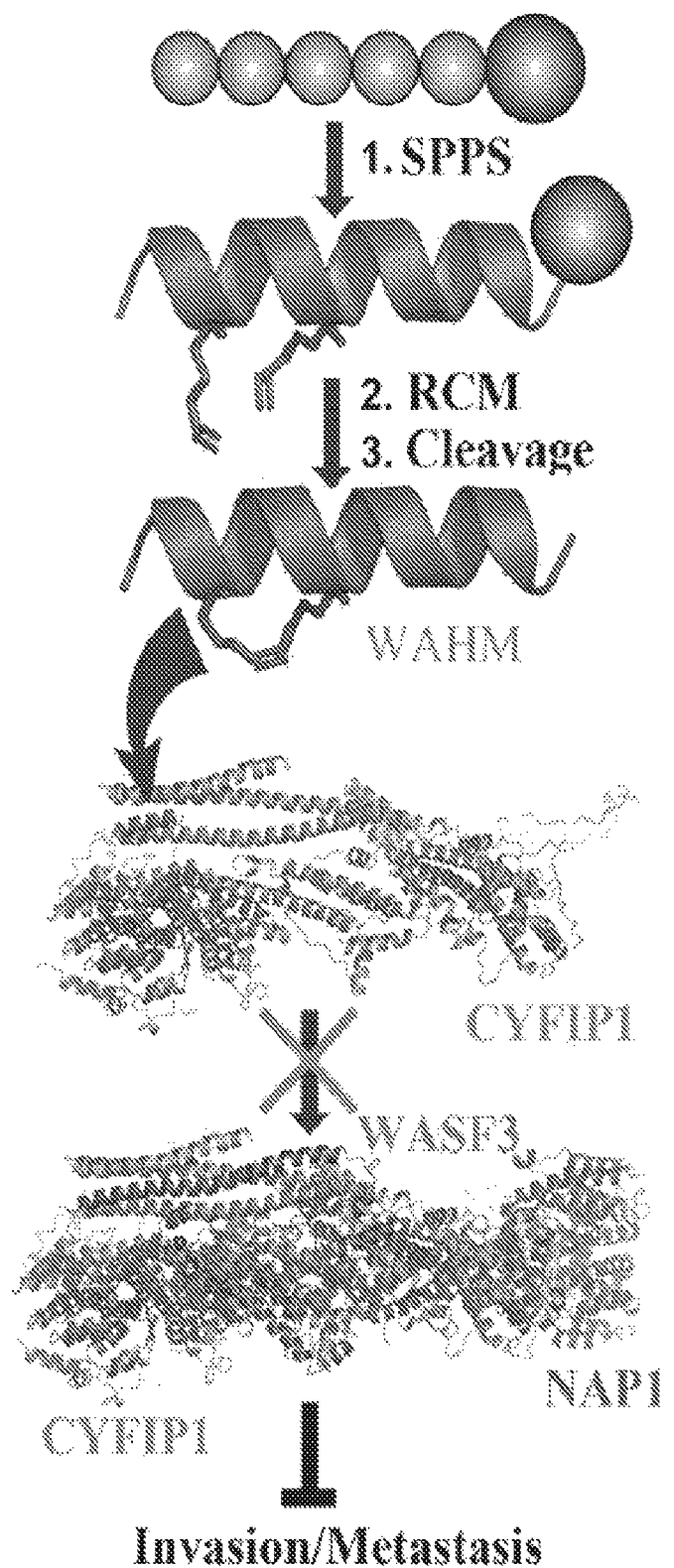

FIG. 11 graphically illustrates the formation of a stapled peptide that targets the protein-protein interface (PPI) between WASF3 and CYFIP1.

FIGS. 12A to 12D shows NCKAP1 interacts with WASF3. (A) Following immunoprecipitation (IP) of WASF3 from MDAMB-231 and Hs578T breast cancer cells, western blot analysis identified NCKAP1 in the IP. The interaction between NCKAP1 and WASF3 was further demonstrated in a GST fusion-protein pulldown assays (B). Lysates from MDA-MB-231 cells were incubated with the GST-tagged WASF3 prepared in BL21 bacterial cells, where the correct size fusion protein was confirmed using anti-GST antibodies (below). The presence of NCKAP1 was then demonstrated in the WASF3-GST (GST-W3) complex using anti-NCKAP1 antibodies. Interaction between NCKAP1 and WASF3 was also demonstrated in vivo following transfection of the NCKAP1-venus1 (NCKAP1-v1) and WASF3-venus2 (WASF3-v2) constructs into MDA-MB-231 cells (C). After 12 hours, GFP was detected by fluorescence microscopy in cells where both constructs were expressed but not in cells where either of the constructs was expressed alone. In the co-transfected cells, a membrane localization of the GFP signal could be seen (arrows).When the WASF3 complex was recovered using immunoprecipitation from MDA-MB-231 cells grown in the presence or absence of FBS (D), NCKAP1 was detected in the complex whether FBS was present or not. The presence of NCK1, however, was only seen in cells treated with FBS, where WASF3 (P-WASF3) was activated.

FIGS. 13A to 13D shows molecular and cell invasion analysis following NCKAP1 knockdown. Breast cancer MDA-MB-231 and Hs578T cells in which NCKAP1 had been stably knocked down (shNCKAP1-1 and shNCKAP1-2) show significantly reduced levels of WASF3 (A) compared with cells carrying a control shRNA (shGFP). Similarly, reduced levels of the WASF1 and WASF2 proteins were also seen in the NCKAP1 knockdown cells. When NCKAP1 knockdown cells were analyzed using Transwell invasion assays (B), their invasion potential was suppressed. Immunoprecipitation of HA-tagged WASF3 from MDA-MB-231 cells in which NCKAP1 had been knocked down shows the absence of RAC1 in the WASF3 immunocomplex (C), compared with parental cells expressing the control shRNA (shGFP). When WASF3 was overexpressed in NCKAP1 knockdown MDAMB-231 and Hs578T cells, there was no recovery of invasion potential (D). *p<0.05, **p<0.01 and ns indicates no statistical significance.

FIG. 14A to 14D shows metastasis in vivo is suppressed following NCKAP1 knockdown. Kaplan-Meier plot analyses with the log-rank test, shows that higher NCKAP1 expression was associated with lower relapse-free survival rates compared with low NCKAP1 expression (A). When MDA-MB-231 cells were implanted subcutaneously into six-week-old female NSG mice (B) primary tumor growth was not affected by knockdown of NCKAP1 (shNCKAP1-1 and shNCKAP1-2), compared to control knockdown (shGFP) cells. When the lungs were removed from these mice, however, the number of nodules on the surface of the lungs was significantly reduced in the NCKAP1 knockdown cells (C). Histological analysis of these lungs demonstrated that, while animals receiving the control cells showed extensive tumor infiltration throughout the lung (D) the NCKAP1 knockdown cells showed relatively few, small tumor foci. Images on the right derived from the boxed areas on the left. **p<0.01.

FIGS. 15A to 15I show RAC1 binding to the WASF3 complex is required for NCKAP1-mediated invasion of breast cancer cells. NCKAP1 overexpression in MDA-MB-231 cells does not affect WASF3 levels and, in T47D cells which do not express WASF3, overexpression of NCKAP1 does not increase WASF3 levels (A). Transwell assays demonstrate that overexpressing NCKAP1 in MDA-MB-231 cells significantly increases invasion potential, although T47D cells are unaffected (B). IP of WASF3 (W3) from MDA-MB-231 cells shows increased RAC1 levels in the WASF3 complex and increased WASF3 phosphorylation when NCKAP1 is overexpressed (C). Treatment of MDA-MB-231 and Hs578T breast cancer cells with the NSC23766 RAC1 inhibitor, leads to a dose-dependent reduction in invasion potential (D) but does not affect protein levels of either WASF3, NCKAP1 or RAC1 (E). IP of WASF3 (W3) from MDA-MB-231 cells treated with NSC23766 shows that, at high (50 uM) concentration, activation of WASF3 is suppressed and RAC1 engagement in the complex is virtually eliminated (F). When a dominant-negative RAC1

(RAC1DN) is introduced into MDAMB-231 cells overexpressing NCKAP1, levels of phosphoactivated WASF3 are significantly reduced in concert with reduced RAC1 levels (G). In Transwell assays, NSC23766 leads to a significant reduction in invasion in both MDA-MB-231 parental cells containing the empty vector (EV) and cells overexpressing NCKAP1 (H). Similarly, the RAC1 dominant-negative construct (RAC1DN) significantly suppresses invasion in MDA-MB-231 cells overexpressing NCKAP1 (I). *p<0.05 and **p<0.01.

FIGS. 16A to 16D show invasion and metastasis analysis after NCKAP1 overexpression in WASF3 knockdown cells. When NCKAP1 was overexpressed in WASF3 knockdown MDA-MB-231 and Hs578T cells (A), cell invasion was not significantly affected (B). Following subcutaneous implantation of MDA-MB-231 cells overexpressing NCKAP1 into NSG mice, the number of nodules on the surface of the lungs after 8 weeks in these animals was not significantly different compared with the WASF3 (shW3) knockdown cells (C). Histological analyses showed the same distribution of tumors in the lungs of these mice carrying the NCKAP1 overexpressing cells as seen for the WASF3 knockdown cells (D). **p<0.01 and ns indicates no statistical significance.

FIGS. 17A to 17H show targeting the NCKAP1-WASF3 complex using stapled peptides leads to loss of invasion in breast cancer cells. Sequence of amino acid regions 631-642 (SEQ ID NO:9), 933-944 (SEQ ID NO:10) and 1110-1121 (SEQ ID NO:11) in NCKAP1 (A) used to design stapled peptides. The three stapled peptides WANT1 (SEQ ID NO:5), WANT2 (SEQ ID NO:6) and WANT3 (SEQ ID NO:7) were designed to target interaction surfaces between CYFIP1 and NCKAP1 where (*) represent the position of the non-natural amino acids (below). The scrambled peptide WANT3 scr (SEQ ID NO:8) was used as a negative control. Transwell invasion assays show that only WANT3 significantly suppresses MDA-MB-231 cell invasion (B) and suppresses both WASF3 and NCKAP1 protein levels (C). A time course of WANT3-FITC uptake using flow cytometry over the first 30 minute of exposure (D) shows progressive fluorescein labeling in breast cancer MDA-MB-231 cells. WANT3 suppresses WASF3 protein levels in a dose-dependent manner (E). WANT3 suppresses phosphoactivation of WASF3 more significantly than the WASF3-CYFIP1 peptide mimic WAHM1 (F). Using a high dose of WANT3 (20 µM) leads to a more remarkable reduction in MDA-MD-231 cell invasion compared with low dose treatment (G). WANT3 peptides were preincubated in serum-containing medium at 37° C. for 1-7 days. When this medium was then used in invasion assays, significant suppression of invasion in MDA-MB-231 cells was still observed for up to three days (H).

Figure 18:
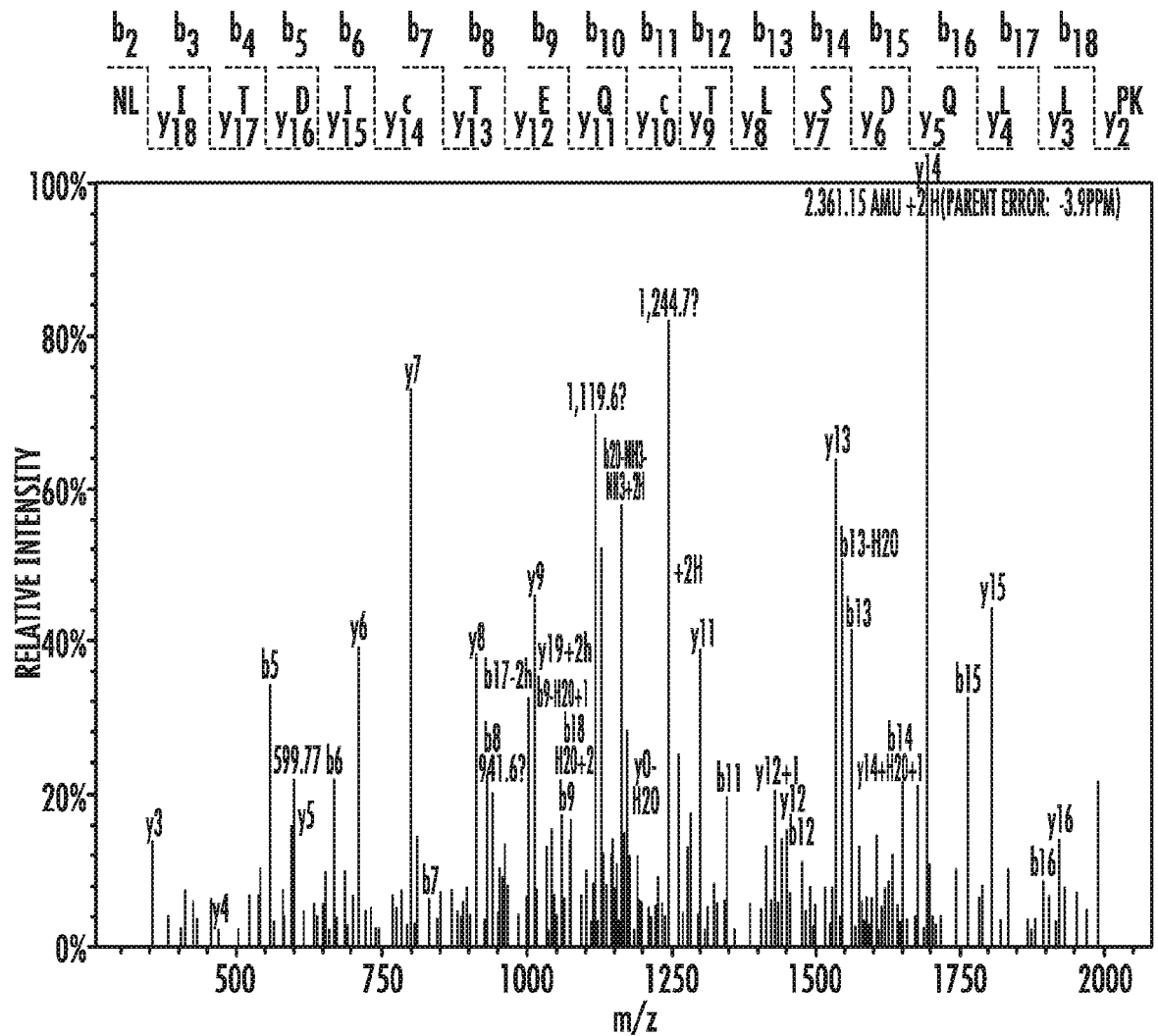

FIG. 18 shows representative MS/MS spectrum of tryptic peptides identifying NCKAP1.

Figure 19:
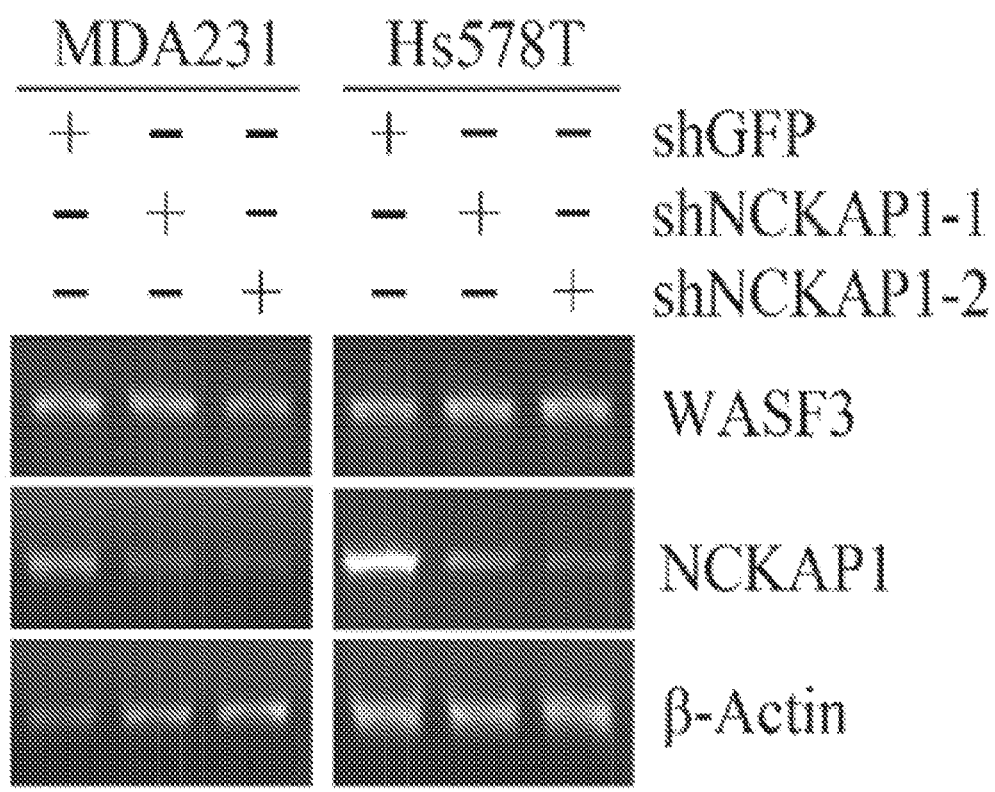

FIG. 19 shows RT-PCR analysis shows that knockdown of NCKAP1 (shNCKAP1-1 and shNCKAP1-2) in breast cancer cell lines MDA-MB-231 and HS578T, does not affect transcript levels of WASF3.

Figure 20:
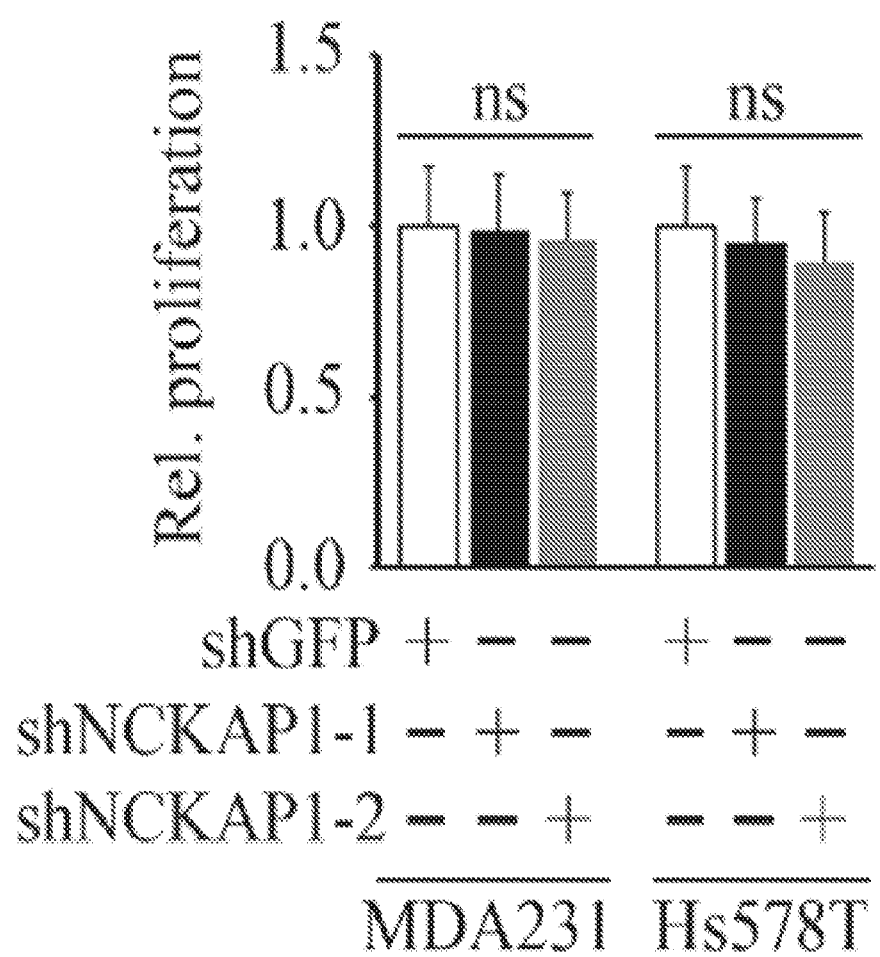

FIG. 20 shows knockdown of NCKAP1 in two different breast cancer cell lines (MDA-MB-231 and Hs578T) has no effect on cell proliferation rate.

Figure 21:
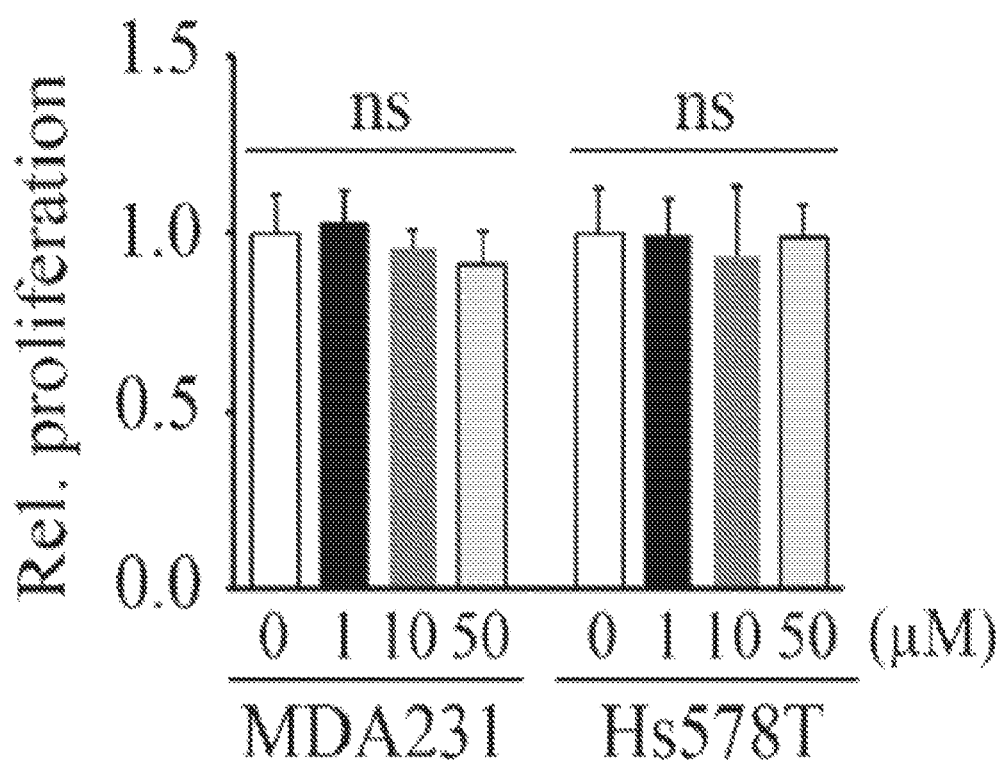

FIG. 21 shows the NSC23766 RAC1 inhibitor does not affect proliferation of breast cancer cells MDA-MB-231 and Hs578T over a range of 1-50 µM.

Figure 22:
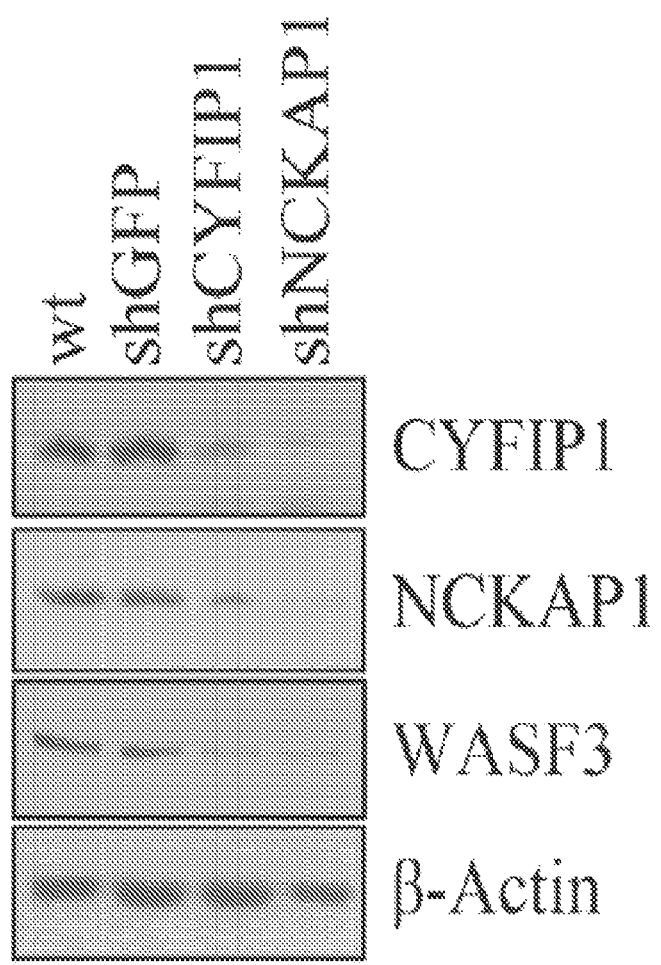

FIG. 22 shows knockdown of either CYFIP1 or NCKAP1 in MDA-MB-231 cells leads to destabilization of WASF3.

Figure 23:
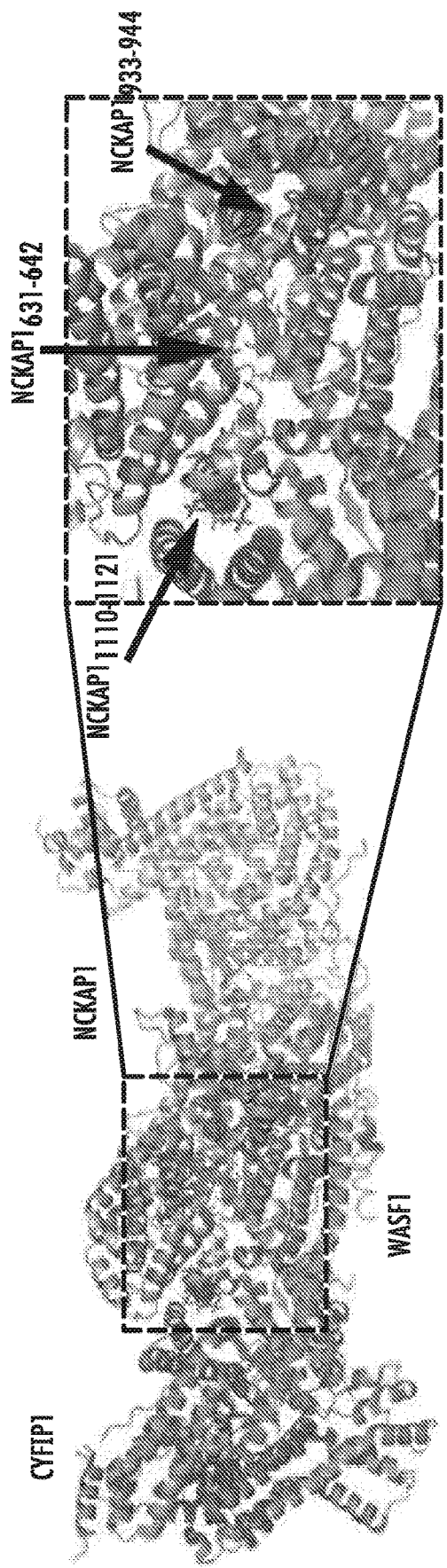

FIG. 23 shows crystal structure of WASF1 in complex with NCKAP1 (rendered in PyMol using PDB 3P8C), shows interaction surfaces between CYFIP1 and NCKAP1 (red) and defines three α-helical surfaces (arrows on right) at amino acids 631-642, 933-944 and 1110-1121 in NCKAP1 that provides contact points for the two proteins.

Figures 24A, 24B:
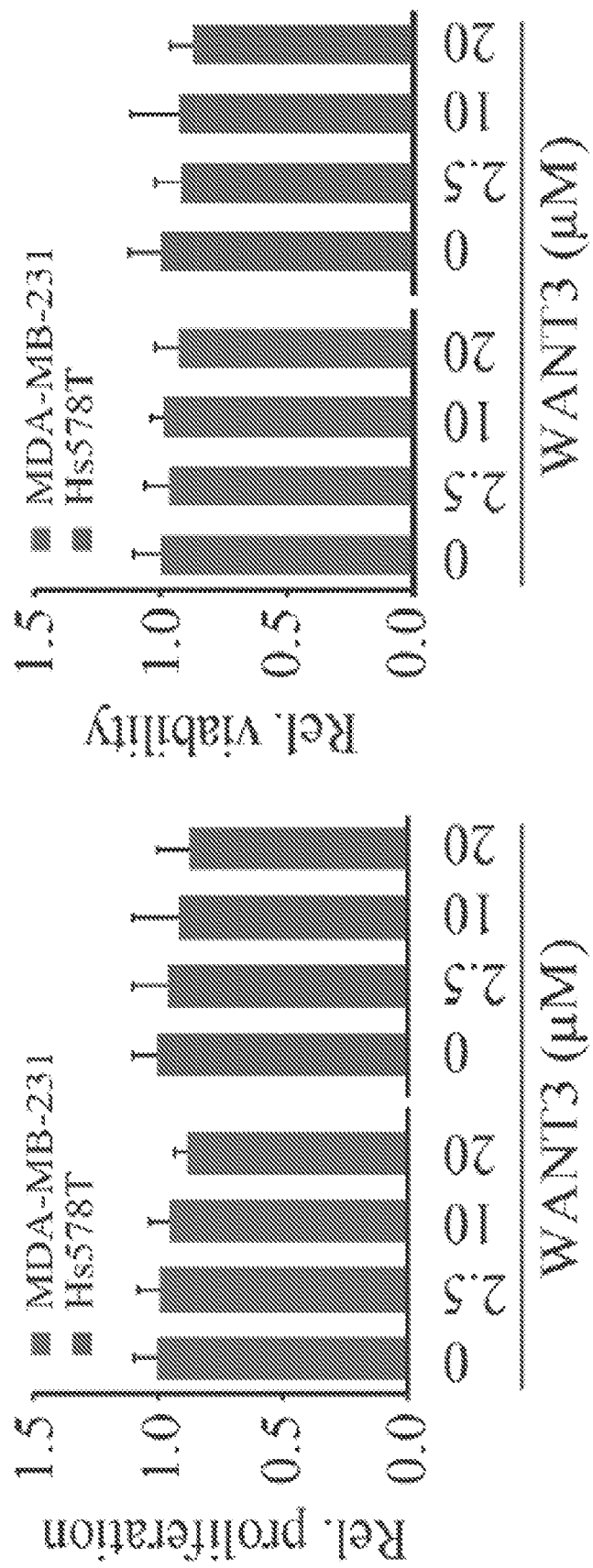

FIGS. 24A to 24B show treatment of MDA-MB-231 and Hs578T breast cancer cells with the WANT3 peptide over a concentration range of 2.5-20 µM, does not affect cell proliferation rate (A) and viability (B).

Figure 25:
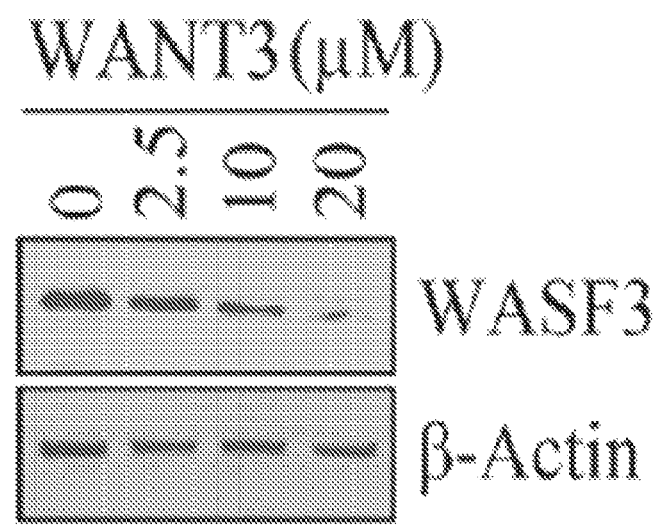

FIG. 25 shows dose-dependent destabilization of the WASF3 protein in MDA-MB-231 cells treated with the WANT3 peptide.

DETAILED DESCRIPTION

The WASF3 gene is a member of the three-member family of the Wiskott-Aldridge Syndrome family of proteins (WASF1, WASF2 and WASF3), which have been implicated in the regulation of cell movement through control of membrane protrusions resulting from reorganization of the actin cytoskeleton (Rotty, J. D., et al. Nat. Rev. Mol. Cell Biol. 14:7-12 (2013); Kurisu, S., et al. Cancer Sci. 101: 2093-2104 (2010); Mendoza, M. C. Cell Dev. Biol. 24:272-279 (2013)). The C-terminus of this protein family carries motifs (VCA) that bind the ARP2/3 complex and monomeric actin that facilitates actin polymerization. In their inactive form, these motifs are masked as a result of conformational constraints imposed by other binding proteins at the N-terminus referred to as the WASF Regulatory Complex (WRC) (Sossey-Alaoui, K., et al. Am. J. Pathol. 170: 211-221 (2007)). Activation of WASF proteins occurs through phosphorylation of tyrosine residues, which leads to disruption of the N-terminal protein complex comprised of NCKAP1 (NAP1), CYFIP1 (SRA1), ABI1 and BRLK. The WASF proteins have been implicated in cell movement related to wound healing, neuronal migration, chemotaxis and immune cell activation but WASF3 is particularly and specifically associated with invasion and metastasis of cancer cells.

The relationship between WASF3 and invasion/metastasis as seen in model cell systems is supported by the observation that high-level WASF3 expression is associated with high-grade primary breast (Sossey-Alaoui, K., et al. Am. J. Pathol. 170:211-221 (2007); Kulkarni, S., et al. PLoS One 7:e42895 (2012)) and prostate cancers (Teng, Y., et al. Br. J. Cancer 103:1066-1075 (2010)). Knockdown of WASF3 in breast and prostate cancer cells leads to a reduction in cell invasion in vitro and metastasis in xenograft models in vivo (Sossey-Alaoui, K., et al. Am. J. Pathol. 170:211-221 (2007); Teng, Y., et al. Br. J. Cancer 103:1066-1075 (2010)). Although primarily considered a protein that regulates actin cytoskeleton dynamics, WASF3 also has a regulatory function that affects expression of genes involved in metastasis such as KISS1, ZEB1 and miRNA-200 (Teng, Y., et al. Int. J. Cancer 129:2825-2835 (2011); Teng, Y., et al. Oncogene 33:203-211 (2014); Teng, Y., et al. JAKSTAT 3:e28086 (2014)). Further, its activity and expression are regulated by other proteins such as JAK2, HSP70, ABL and HIF1 (Sossey-Alaoui, K., et al. J. Biol. Chem. 82:26257-26265 (2007); Ghoshal, P., et al. Int. J. Cancer 131:E905-E915 (2012); Teng, Y., et al. J. Biol. Chem. 287:10051-10059 (2012); Teng, Y., et al. Carcinogenesis 4:1994-1999 (2013)), all of which have also been implicated in the metastasis phenotype. Recently, WASF3 has also been shown to interact with the ATAD3A mitochondrial protein which regulates its stability at the mitochondrial membrane (Teng, Y. et al.

Oncogene Mar. 30 (2015)). Since genetic inactivation of WASF3 leads to suppression of metastasis, WASF3 could potentially be targeted as an approach to suppress metastasis.

The structure of the WASF proteins determines their function, which is regulated by the WRC through interactions with two different subcomplexes (Chen, Z., et al. Nature 468:533-538 (2010)) involving the CYFIP1-NCKAP1 dimer and the ABI2-BRK1-WASF trimer. The regulation of the VCA domain, and hence actin polymerization, is facilitated by a complex structural interaction between CYFIP1/NCKAP1 and the WASF proteins that act allosterically to regulate the WASF proteins so as to prevent actin polymerization. The crystal structure of WASF1, and its association with these proteins, demonstrate several critical interacting sites throughout the WRC protein complex (Chen, Z., et al. Nature 468:533-538 (2010); Chen, B., et al. Cell 156:195-207 (2014)). Currently, there are no inhibitors described that specifically inhibit WASF3, requiring development of an approach to target its function.

A relatively new class of inhibitors that provides the potential for much greater inhibition of protein function with high specificity has been developed, in which chemically stabilized peptides are used to target protein-protein interactions (PPIs). These "stapled peptides" (SP) are synthetically designed to stabilize and constrain an α-helical structure through macrocyclic ring formation using ring closing metathesis chemistry (Schafmeister, C. E., et al. J. Am Chem. Soc. 122:5891-5892 (2000); Blackwell, H. E., et al. J. Org. Chem. 66:5291-9302 (2001); Walensky, L. D. Science 305:1466-1470 (2004); Higueruelo, A. P., et al. Curr. Opin. Pharmacol. 13:791-796 (2013)). Further, these locked peptides can exhibit drug-like properties including enhanced cell permeability and resistance to proteolytic degradation (Verdine, G. L., et al. Clin. Cancer Res. 13:7264-7270 (2007); Wittrup, K. D., et al. Methods Enzymol. 503:xiii-xiv (2012); Chang, Y. S., et al. Proc. Natl. Acad. Sci. USA. 110:E3445-E3454 (2013)).

Stapled peptides that target essential interactions between WASF3 and CYFIP1, or CYFIP1 with NCKAP1, are disclosed herein. These peptides are shown to cause suppression of WASF3 activation, thereby leading to loss of invasion potential in breast and prostate cancer cells without inhibiting cellular proliferation.

Non-natural, synthetic polypeptides are disclosed that contain a chemically stabilized α-helical shape that mimics the protein-protein interface (PPI) between WASF3 and CYFIP1, allowing them to bind to an endogenous WASF3 or CYFIP1 in physiological, or supraphysiological, conditions and to inhibit the WASF3 from binding to an endogenous CYFIP1.

In some embodiments, the polypeptide mimics amino acids 26-41 of WASF3. The following is an amino acid sequence for human WASF3, isoform 1 (Accession No. NP_006637):

```
                                          (SEQ ID NO: 15)
MPLVKRNIEPRHLCRGALPEGITSELECVTNSTLAAIIRQLSSLSKHAED

IFGELFNEANNFYIRANSLQDRIDRLAVKVTQLDSTVEEVSLQDINMKKA

FKSSTVQDQQVVSKNSIPNPVADIYNQSDKPPPLNILTPYRDDKKDGLKF

YTDPSYFFDLWKEKMLQDTEDKRKEKRRQKEQKRIDGTTREVKKVRKARN

RRQEWNMMAYDKELRPDNRLSQSVYHGASSEGSLSPDTRSHASDVTDYSY
```

```
                       -continued
PATPNHSLHPQPVTPSYAAGDVPPHGPASQAAEHEYRPPSASARHMALNR

PQQPPPPPPPQAPEGSQASAPMAPADYGMLPAQIIEYYNPSGPPPPPPPP

VIPSAQTAFVSPLQMPMQPPFPASASSTHAAPPHPPSTGLLVTAPPPPGP

PPPPPGPPGPGSSLSSSPMHGPPVAEAKRQEPAQPPISDARSDLLAAIRM

GIQLKKVQEQREQEAKREPVGNDVATILSRRIAVEYSDSDDDSEFDENDW

SD.
```

Therefore, in some embodiments, the polypeptide mimics α-helix forming amino acids 26-41 of SEQ ID NO:15 (underlined above). Therefore, in some embodiments, the polypeptide mimics α-helix forming amino acids LECVTNSTLAAIIRQL (SEQ ID NO:14). For example, the polypeptide can comprise a variant of the amino acid sequence SEQ ID NO:14, wherein the variant comprises pair of olefin terminated, non-natural amino acids that form a hydrocarbon staple to stabilize the α-helical shape. As an example, the polypeptide can comprise the amino acid sequence LEKXTNSXLAKIIRQL (SEQ ID NO:1) or LEKKTNXTLAXIIRQL (SEQ ID NO:2), where X is (S)-2-(4'-pentenyl)alanine.

In some embodiments, the polypeptide mimics amino acids of CYFIP1 that bind WASF3. The following is an amino acid sequence for human CYFIP1, isoform a (Accession No. NP_055423):

```
                                          (SEQ ID NO: 16)
MAAQVTLEDALSNVDLLEELPLPDQQPCIEPPPSSLLYQPNFNTNFEDRN

AFVTGIARYIEQATVHSSMNEMLEEGQEYAVMLYTWRSCSRAIPQVKCNE

QPNRVEIYEKTVEVLEPEVTKLMNFMYFQRNAIERFCGEVRRLCHAERRK

DFVSEAYLITLGKFINMFAVLDELKNMKCSVKNDHSAYKRAAQFLRKMAD

PQSIQESQNLSMFLANHNKITQSLQQQLEVISGYEELLADIVNLCVDYYE

NRMYLTPSEKHMLLKVMGFGLYLMDGSVSNIYKLDAKKRINLSKIDKYFK

QLQVVPLFGDMQIELARYIKTSAHYEENKSRWTCTSSGSSPQYNICEQMI

QIREDHMRFISELARYSNSEVVTGSGRQEAQKTDAEYRKLFDLALQGLQL

LSQWSAHVMEVYSWKLVHPTDKYSNKDCPDSAEEYERATRYNYTSEEKFA

LVEVIAMIKGLQVLMGRMESVFNHAIRHTVYAALQDFSQVTLREPLRQAI

KKKKNVIQSVLQAIRKTVCDWETGHEPFNDPALRGEKDPKSGFDIKVPRR

AVGPSSTQLYMVRTMLESLIADKSGSKKTLRSSLEGPTILDIEKFHRESF

FYTHLINFSETLQQCCDLSQLWFREFFLELTMGRRIQFPIEMSMPWILTD

HILETKEASMMEYVLYSLDLYNDSAHYALTRFNKQFLYDEIEAEVNLCFD

QFVYKLADQIFAYYKVMAGSLLLDKRLRSECKNQGATIHLPPSNRYETLL

KQRHVQLLGRSIDLNRLITQRVSAAMYKSLELAIGRFESEDLTSIVELDG

LLEINRMTHKLLSRYLTLDGFDAMFREANHNVSAPYGRITLHVFWELNYD

FLPNYCYNGSTNRFVRTVLPFSQEFQRDKQPNAQPQYLHGSKALNLAYSS

IYGSYRNFVGPPHFQVICRLLGYQGIAVVMEELLKVVKSLLQGTILQYVK

TLMEVMPKICRLPRHEYGSPGILEFFHHQLKDIVEYAELKTVCFQNLREV

GNAILFCLLIEQSLSLEEVCDLLHAAPFQNILPRVHVKEGERLDAKMKRL

ESKYAPLHLVPLIERLGTPQQIAIAREGDLLTKERLCCGLSMFEVILTRI
```

-continued
RSFLDDPIWRGPLPSNGVMHVDECVEFHRLWSAMQFVYCIPVGTHEFTVE

QCFGDGLHWAGCMIIVLLGQQRRFAVLDFCYHLLKVQKHDGKDEIIKNVP

LKKMVERIRKFQILNDEIITILDKYLKSGDGEGTPVEHVRCFQPPIHQSL

ASS.

In some embodiments, the polypeptide mimics α-helix forming amino acids of SEQ ID NO:16 that bind WASF3.

Non-natural, synthetic polypeptides are also disclosed that contain a chemically stabilized α-helical shape that mimics the protein-protein interface (PPI) between NCKAP1 and CYFIP1, allowing them to bind to an endogenous NCKAP1 or CYFIP1 in physiological, or supraphysiological, conditions and to inhibit endogenous NCKAP1 from binding to an endogenous CYFIP1.

In some embodiments, the polypeptide mimics amino acids 631-642, 933-944, or 1110-1121 of NCKAP1. The following is an amino acid sequence for human NCKAP1, isoform 1 (Accession No. NP_038464):

(SEQ ID NO: 17)
MSRSVLQPSQQKLAEKLTILNDRGVGMLTRLYNIKKACGDPKAKPSYLID

KNLESAVKFIVRKEPAVETRNNNQQLAQLQKEKSEILKNLALYYFTFVDV

MEFKDHVCELLNTIDVCQVFEDITVNEDLTKNYLDLIITYTTLMILLSRI

EERKAIIGLYNYAHEMTHGASDREYPRLGQMIVDYENPLKKMMEEFVPHS

KSLSDALISLQMVYPRRNLSADQWRNAQLLSLISAPSTMLNPAQSDTMPC

EYLSLDAMEKWIIFGFILCHGILNTDATALNLWKLALQSSSCLSLERDEV

EHIHKAAEDLEVNIRGYNKRINDIRECKEAAVSHAGSMHRERRKFLRSAL

KELATVLSDQPGLLGPKALFVFMALSFARDEIIWLLRHADNMPKKSADDF

IDKHIAELIFYMEELRAHVRKYGPVMQRYYVQYLSGFDAVVLNELVQNLS

VCPEDESIIMSSEVNTMTSLSVKQVEDGEVFDFRGMRLDWFRLQAYTSVS

KASLGLADHRELGKMMNTIIFHTKMVDSLVEMLVETSDLSIFCFYSRAFE

KMFQQCLELPSQSRYSIAFPLLCTHFMSCTHELCPEERHHIGDRSLSLCN

MELDEMAKQARNLITDICTEQCTLSDQLLP<u>KHCAKTISQAVNK</u>KSKKQTG

KKGEPEREKPGVESMRKNRLVVTNLDKLHTALSELCFSINYVPNMVVWEH

TFTPREYLTSHLEIRFTKSIVGMTMYNQATQEIAKPSELLTSVRAYMTVL

QSIENYVQIDITRVENNVLLQQTQHLDSHGEPTITSLYTNWYLETLLRQV

SNGHIAYFPAMKAFVNLPTENELTFNAEEYSDISEMRSLSELLGPYGMKF

LSESLMWHISSQVAELKKLVVENVDVLTQMRTSFDKPDQMAALFKRLSSV

DSVLKRMTIIGVILSFRSLAQEALRDVLSYHI<u>PFLVSSIEDFKD</u>HIPRET

DMKVAMNVYELSSAAGLPCEIDPALVVALSSQKSENISPEEEYKIACLLM

VFVAVSLPTLASNVMSQYSPAIEGHCNNIHCLAKAINQIAAALFTIHKGS

IEDRLKEFLALASSSLLKIGQETDKTTTRNRESVYLLLDMIVQESPFLTM

DLLESCFP<u>YVLLRNAYHAVYK</u>QSVTSSA.

Therefore, in some embodiments, the polypeptide mimics α-helix forming amino acids 631-642, 933-944, or 1110-1121 of SEQ ID NO:17 (underlined above). Therefore, in some embodiments, the polypeptide mimics α-helix forming amino acids KHCAKTISQAVNK (SEQ ID NO:9), PFLVSSIEDFKD (SEQ ID NO:10), or VLLRNAYHAVYK (SEQ ID NO:11). For example, the polypeptide can comprise a variant of the amino acid sequence SEQ ID NO:9, 10, or 11, wherein the variant comprises pair of olefin terminated, non-natural amino acids that form a hydrocarbon staple to stabilize the α-helical shape. As an example, the polypeptide can comprise the amino acid sequence KHCAXTISXAVNK (SEQ ID NO:5), ELXSSIXDFKDHK (SEQ ID NO:6), or VLXRNAXHAVYK (SEQ ID NO:7) where X is (S)-2-(4'-pentenyl)alanine.

In some embodiments, the polypeptide mimics amino acids of CYFIP1 that bind NCKAP1. Therefore, in some embodiments, the polypeptide mimics α-helix forming amino acids of SEQ ID NO:16 that bind NCKAP1.

"Peptide stapling" is a term coined from a synthetic methodology wherein two olefin-containing side-chains present in a polypeptide chain are covalently joined (e.g., "stapled together") using a ring-closing metathesis (RCM) reaction to form a cross-linked ring. However, the term "peptide stapling," as used herein, encompasses the joining of two double bond-containing side-chains, two triple bond-containing side-chains, or one double bond-containing and one triple bond-containing side chain, which may be present in a polypeptide chain, using any number of reaction conditions and/or catalysts to facilitate such a reaction, to provide a singly "stapled" polypeptide. Additionally, the term "peptide stitching," as used herein, refers to multiple and tandem "stapling" events in a single polypeptide chain to provide a "stitched" (multiply stapled) polypeptide.

In some embodiments, the disclosed peptides include a hydrocarbon staple. The genesis of the hydrocarbon stapling technique can be traced to the ruthenium based Grubb's catalysis used for ring closing metathesis. The α-helix features 3.6 residues per complete turn, which places the i, i+4, i+7, and i+11 side chains on the same face of the folded structure. Therefore, stapling cross-links two α,α disubstituted amino acids bearing olefinic chains of variable length at positions "i" and "i+4" or "i+7" in the peptide sequence. In general, the first step in designing stapled peptides for macromolecular target is the identification of appropriate sites for incorporating the non natural amino acids used to form the hydrocarbon cross-link. Generally, residues which are not involved in the target recognition are chosen as potential sites for incorporation of olefin-bearing building blocks. These site are subsequently used to incorporate various suitable stapling systems such as i, i+3; i, i+4 or i, i+7. The classical strategy to stabilize the α-helical conformation in peptides employs covalent bonds between the i and i+3, i and i+4 or i and i+7 side chain groups.

In some embodiments, the polypeptide comprises two non-natural amino acids on the same side of the α-helix that are crosslinked to stabilize the α-helical shape. For example, the two non-natural amino acids can be four (i and i+4) or seven (i and i+7) amino acids apart. In some cases, the non-natural amino acids can comprise olefinic side chains, such as (S)-2-(2'-propenyl)alanine ("S3"), (S)-2-(4'-pentenyl)alanine ("S5"), (S)-2-(5'-hexenyl)alanine ("S6"), (S)-2-(7'-octenyl)alanine ("S8"), (R)-2-(2'-propenyl)alanine ("R3"), (R)-2-(4'-pentenyl)alanine ("R5"), (R)-2-(5'-hexenyl)alanine ("R6"), (R)-2-(7'-octenyl) alanine ("R8").

The disclosed peptides can be stapled in any suitable paring, including, but not limited to, pairing selected from the group consisting of an S5-S5 pairing (i.e., i, i+4), an S5-R8 pairing (i.e., i, i+7), an S8-R5 pairing (i.e., i, i+7), an R3-S6 pairing (i.e., i, i+3), an R6-S3 pairing (i.e., i, i+3), an R3-S5 pairing (i.e., i, i+3), an R5-S3 pairing (i.e., i, i+3), or combinations of pairings within the polypeptide sequence.

The hydrocarbon bridge can then be formed by a ring-closing metathesis reaction catalyzed by benzylidenebis (tricyclohexyl-phosphine)-dichlororuthenium (Grubb's catalyst).

Stapling of a peptide using all-hydrocarbon cross-link has been shown to help maintain its native conformation and/or secondary structure, particularly under physiologically relevant conditions. For example, stapling a polypeptide by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncross-linked (e.g., "unstapled") peptide.

Other forms of chemical stabilization may also be used in the disclosed peptides. For example, amino acids, and unstapled, partially stapled, and stapled peptides and proteins, and unstitched, partially stitched, and stitched peptides and proteins) may exist in particular geometric or stereoisomeric forms. The disclosed peptides can include all such compounds, including cis- and trans-isomers, R- and S-enantiomers, diastereomers, (D)-isomers, (L)-isomers, the racemic mixtures thereof, and other mixtures thereof. Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer.

The polypeptide can be a synthetic peptide containing non-natural amino acids, or a peptidomimetic. As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half-life, etc. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of non-natural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The disclosed compounds may also be substituted with any number of substituents or functional moieties. In general, the term "substituted" refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The disclosed peptides can contain any and all such combinations in order to arrive at a stable substituent/moiety. For the disclosed peptides, heteroatoms such as nitrogen may have hydrogen substituents and/or any suitable substituent as described herein which satisfy the valencies of the heteroatoms and results in the formation of a stable moiety.

Peptides and peptidomimetics can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used.

Examples of chemical synthesis technologies are solid phase synthesis and liquid phase synthesis. Solid phase synthesis methods are largely classified by the tBoc method and the Fmoc method, depending on the type of protective group used. Typically used protective groups include tBoe (t-butoxycarbonyl), Cl—Z (2-chlorobenzyloxycarbonyl), Br—Z (2-bromobenzyloyycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Methods of de novo synthesizing peptides and peptidomimetics are described, for example, in Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000.

Alternatively, the peptide may be synthesized using recombinant techniques. In this case, a nucleic acid encoding the peptide is cloned into an expression vector under the control of expression control sequences (e.g. a promoter, a terminator and/or an enhancer) allowing its expression. The expression vector is then transfected into a host cell (e.g. a human, CHO, mouse, monkey, fungal or bacterial host cell), and the transfected host cell is cultivated under conditions suitable for the expression of the peptide. Standard recombinant DNA and molecular cloning techniques are described for example in: Sambrook, and Maniatis, Molecular Cloning: A Laboratory Manual, Second Edition, Cold Spring Harbor Laboratory Press, Cold Spring Harbor, N.Y. (1989); Silhavy et al., Experiments with Gene Fusions, Cold Spring Harbor Laboratory Press, Cold Spring Harbor, N.Y. (1984);

and, Ausubel et al., Current Protocols in Molecular Biology, published by Greene Publishing Assoc. and Wiley-Interscience (1987).

The method of producing the peptide may optionally comprise the steps of purifying said peptide, chemically modifying said peptide, and/or formulating said peptide into a pharmaceutical composition.

The polypeptide can be isoform specific. In some embodiments, the polypeptide is selective for the protein-protein interface (PPI) WASF3 and CYFIP1. As used herein, a polypeptide is "selective" for a receptor if it specifically binds one isoform of a receptor with a binding affinity that is at least 5× higher than its affinity for the other isoform. For example, the polypeptide can have a binding affinity for one isoform that is at least 5, 6, 7, 8, 9, 10, 20, or more than that of the other isoform. For example, the polypeptide can be selective for WASF3 and not affect the function of WASF1 and WASF2.

In some embodiments, the peptide is about 8 to 100 amino acids in length, including about 10 to 50 amino acids in length. In some embodiments, the peptide is less than 51 amino acids in length, including less than 50, 45, 40, 35, 30, 25, or 20 amino acids in length. Therefore, the provided polypeptide can further constitute a fusion protein or otherwise have additional N-terminal, C-terminal, or intermediate amino acid sequences.

In some cases, introduction of a hydrocarbon staple results in poor water solubility and cell permeability. To increase cell permeability and solubility of these peptides, the disclosed polypeptide can be linked to a cell permeability moiety. A "cell permeability" or a "cell-penetration" moiety refers to any molecule known in the art which is able to facilitate or enhance penetration of molecules through membranes. Non-limitative examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids and transporter peptides. Examples for lipidic moieties which may be used according to the present invention: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoyl-phosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((-N,N,N-trimethylammoniumethyl-aminocarbonylmethylene)ethylenediamine tetraiodide; N5N"-Bis(hexadecylaminocarbonylmethylene)-N,N', N"-tris((-N,N,N-trimethylammonium-ethylaminocarbonyl-methylenediethylenetriamine hexaiodide; N,N-Bis(dodecy-laminocarbonylmethylene)-N,NM-bis((-N,N,N-trimethyl-ammonium ethylaminocarbonylmethylene)cyclohexylene-1,4-diamine tetraiodide; 1,7,7-tetra-((-N,N,N-tetrametihtylammoniumethylamino-carbonylmethylene)-3-hexadecylaminocarbonyl-methylene-1,3,7-triaazaheptane heptaiodide; N5N5N',N'-tetra((-N,N,N-trimethylammo-nium-ethylaminocarbonylmethylene)-N'-(152-dioleoyl-glycero-3-phosphoethanolamino carbonylmethylene)diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl)methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1ˆ-dipalmitoyl-sn-S-succinyl-glycerol; 1,3-dipalmitoyl-2-succinylglycerol, l-hexadecyl-2-pahnitoylglycero-phosphoethanolamine, and palmitoylhomocysteine.

In some embodiments, the disclosed polypeptide can be linked to a protein transduction domain to effectively enter a cell. The protein transduction domain sequence can be any internalization sequence (e.g., cell penetrating peptide) known or newly discovered in the art, or conservative variants thereof. Non-limiting examples of cellular internalization transporters and sequences include Polyarginine (e.g., R9), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

Addition of water soluble polymers or carbohydrates to polypeptide drugs has been shown to prevent their degradation and increase their half-life. For instance, "PEGylation" of polypeptide drugs protects them and improves their pharmacodynamic and pharmacokinetic profiles. The PEGylation process attaches repeating units of polyethylene glycol (PEG) to a polypeptide drug. PEGylation of molecules can lead to increased resistance of drugs to enzymatic degradation, increased half-life in vivo, reduced dosing frequency, decreased immunogenicity, increased physical and thermal stability, increased solubility, increased liquid stability, and reduced aggregation. Therefore, in some embodiments, the disclosed polypeptide is covalently linked to a water soluble polymer, such as a polyethylene glycol.

The most common route for PEG conjugation of polypeptides has been to activate the PEG with functional groups suitable for reactions with lysine and N-terminal amino acid groups. The monofunctionality of methoxyPEG makes it particularly suitable for protein and peptide modification because it yields reactive PEGs that do not produce cross-linked polypeptides, as long as diol PEG has been removed. Branched structures of PEG have also been proven to be useful for PEGylation of a protein or a peptide. For example, a branched PEG attached to a protein has properties of a much larger molecule than a corresponding linear mPEG of the same molecular weight. Branched PEGs also have the advantage of adding two PEG chains per attachment site on the protein, therefore reducing the chance of protein inactivation due to attachment. Furthermore, these structures are more effective in protecting proteins from proteolysis, in reducing antigenicity, and in reducing immunogenicity.

To increase cell permeability and solubility of these peptides, the peptides can be optimized to increase their amphipathic properties. In some cases, an overall net charge (neutral or positive) is needed for permeability. Any method that alters the overall net charge can affect permeability. In some cases, 1, 2, 3, 4, or more hydrophilic residues can be added on the solvent-exposed face of the helix. For example, the hydrophilic residue can be a lysine, aspartic acid, glutamic acid, arginine, histidine, serine, asparagine, or glutamine. In some cases, lysine and/or arginine is used since they have positive charges that help to increase permeability. Non-natural amino acids bearing hydrophilic or charged properties can also be added.

Pharmaceutical Compositions

Also disclosed is a pharmaceutical formulations, comprising any of the polypeptides disclosed herein in a pharmaceutically acceptable carrier. The disclosed polypeptides can be incorporated in the formulations described below as neutral compounds, pharmaceutically acceptable salts, and/or prodrugs. Pharmaceutical formulations can be designed for immediate release, sustained release, delayed release and/or burst release of one or more polypeptides in a therapeutically effective amount.

The compounds described herein can be formulated for parenteral administration. Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof. For parenteral administration, the compounds, and optionally one or more additional active agents, can be incorporated into microparticles, nanoparticles, or combinations thereof that provide controlled release. For example, the compounds and/or one or more additional active agents can be incorporated into polymeric microparticles which provide controlled release of the drug (s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

The polypeptide can also be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection. A variety of carriers may be incorporated into the depot formulation to provide for the controlled release of the active agent. In some cases, depot formulations contain one or more biodegradable polymeric or oligomeric carriers. Suitable polymeric carriers include, but are not limited to poly(lactic acid) (PLA), poly(lactic-co-glycolic acid) (PLGA), poly(lactic acid)-polyethyleneglycol (PLA-PEG) block copolymers, polyanhydrides, poly(ester anhydrides), polyglycolide (PGA), poly-3-hydroxybutyrate (PHB) and copolymers thereof, poly-4-hydroxybutyrate (P4HB), polycaprolactone, cellulose, hydroxypropyl methylcellulose, ethylcellulose, as well as blends, derivatives, copolymers, and combinations thereof. In depot formulations containing a polymeric or oligomeric carrier, the carrier and active agent can be formulated as a solution, an emulsion, or suspension. One or more neuroactive steroids, and optionally one or more additional active agents, can also be incorporated into polymeric or oligomeric microparticles, nanoparticles, or combinations thereof.

Formulations may also be in the form of an organogel (assuming the compound steroid is relatively water insoluble) or a hydrogel. Numerous gel formulations are known. See, for example, U.S. Pat. No. 5,411,737 by Hsu, et al. Hydrogels, especially those further including nanoparticles microparticles for sustained, immediate and/or delayed release, can also be used.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, vaginal and rectal administration, are also contemplated herein. Transdermal patches, including iotophoretic and electrophoretic devices, are well known to those of skill in the art. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 g.

The disclosed polypeptides can also be administered adjunctively with other active compounds such as analgesics, anti-inflammatory drugs, antipyretics, antiepileptics, antihistamines, antimigraine drugs, antimuscarinics, anxiolytics, sedatives, hypnotics, antipsychotics, bronchodilators, anti asthma drugs, cardiovascular drugs, corticosteroids, dopaminergics, electrolytes, parasympathomimetics, stimulants, anorectics and anti-narcoleptics.

Methods

Also disclosed is a method for inhibiting binding of WASF3 to CYFIP1 and/or the binding of CYFIP1 to NCKAP1. This method can involve contacting WASF3, CYFIP1, or NCKAP1 in physiological conditions with a polypeptide disclosed herein.

Also disclosed is a method for treating or suppressing invasion and metastasis of a cancer in a subject. This method can involve administering to the subject a therapeutically effective amount of a pharmaceutical composition containing a polypeptide disclosed herein.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

In some embodiments, the disclosed polypeptide is administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of polypeptide administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

Definitions

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "peptide," "protein," "polypeptide," "polyamino acid," are used interchangeably to refer to a natural or synthetic molecule comprising two or more amino acids linked by the carboxyl group of one amino acid to the alpha amino group of another. In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. Also included in the term "polypeptides" are cis- and trans-isomers, R- and S-enantiomers, D-isomers, L-isomers, and racemic mixtures.

The term "residue" as used herein refers to an amino acid that is incorporated into a polypeptide. The amino acid may be a naturally occurring amino acid and, unless otherwise limited, may encompass analogs of natural amino acids that can function in a similar manner as naturally occurring amino, acids.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Targeting the WASF3-CYFIP1 Complex Using Stapled Peptides Leads to Loss of Invasion in Cancer Cells Methods Chemical Reagents Rink amide MBHA resin and Fmoc-protected amino acids were purchased from Novabiochem unless otherwise indicated. HCTU and Fmoc-11-amino-3,6,9-trioxaundecanoic acid (PEG3) were purchased from ChemPep. (S)—N-Fmoc-2-(4'-pentenyl) alanine was purchased from Okeanos, and D-biotin from Gold Biotechnology. Piperidine, diisopropylethylamine, triisopropylsilane and Grubb's first generation catalyst were purchased from Sigma-Aldrich. Trifluoroacetic acid and all other solvents were obtained from Fisher. HABA reagent was purchased from MP Biomedicals, and Avidin from Rockland.

Stapled Peptide Synthesis

Peptides were prepared manually using standard Fmoc solid-phase peptide synthesis. Briefly, peptides were synthesized on a 50 μmol scale using rink amide MBHA resin with a loading capacity of 59 μmol/g of resin. All deprotection steps were performed using 25% piperidine in N-methylpyrrolidinone (NMP) for 25 min. All natural Fmoc-protected amino acids were coupled for 45 minutes using 0.5 M amino acid (1 mL, 500 μmol, 10 equiv), 0.5 M HCTU (0.99 mL, 495 μmol, 9.9 equiv), and diisopropylethylamine (174 μL, 1 mmol, 20 equiv) in NMP. (S)—N-Fmoc-2-(4'-pentenyl) alanine was coupled for 1.5 hours using 0.5 M amino acid (0.4 mL, 200 μmol, 4 equiv), 0.5 M HCTU (0.495 mL, 247.5 μmol, 4.95 equiv), and diisopropylethylamine (87 μmol, 500 μmol, 10 equiv) in NMP. The resin was washed three times in NMP between all deprotection and coupling steps. After completion of the peptide sequence, but prior to deprotection, olefin ring-closing metathesis was performed twice for 1 hour each using a solution of 9.72 mM Grubb's first generation catalyst (2 mL, 19.4 μmol, 0.39 equiv) in dichloroethane. The amino terminus was then deprotected and coupled for 1.5 hours using 0.5 M PEG3 (0.4 mL, 200 μmol, 4 equiv), 0.5 M HCTU (0.495 mL, 247.5 μmol, 4.95 equiv), and diisopropylethylamine (87 μmol, 500 μmol, 10 equiv) in NMP. Following deprotection, the peptide was biotinylated overnight using a 2.4 mL solution of d-biotin (499 μmol, 9.98 equiv) and HCTU (527 μmol, 10.5 equiv) in 1:1 dimethylformamide/dimethylsulfoxide and diisopropylethylamine (150 μL, 861 μmol, 17.2 equiv). The peptide was cleaved from the resin for 4 hours in a solution containing 95/2.5/2.5 TFA/water/triisopropylsilane. The peptide was then filtered through glass wool into 6 mL of ice cold tert-butyl methyl ether and pelleted by centrifugation. The supernatant was discarded and the pellet was dried and dissolved in methanol for characterization and purification by LC/MS and reverse-phase HPLC using an Agilent 1200 series HPLC coupled to an Agilent 1620 LC/MS. The peptide was purified on a Zorbax SB-C18 5 μm column using a gradient of 10%-100% acetonitrile containing 0.1% TFA. The purified peptide was quantified using the Pierce HABA-Avidin microplate protocol by measuring absorbance at 500 nm using the Biotek Synergy 2 Microplate Reader. WAHM1 molecular weight=2291.4 (expected=2291.8), WAHM2 molecular weight=2305.2 (expected=2305.8), SCR1 molecular weight=2291.4 (expected=2291.8), SCR2 molecular weight 2305.8 (expected=2305.8).

Molecular Reagents and Constructs pLKO.1 lentiviral vectors harboring shRNAs targeting WASF1, WASF2, WASF3 or NCKAP1 were obtained from Open Biosystems and shCYFIP1 was from Sigma-Aldrich. WASF2 and WASF3 antibodies were purchased from Cell Signaling Technology. Antibodies against CYFIP1, NCKAP1 and WASF1 were from Abcam and KISS1 was from Santa Cruz Biotechnology. Antibodies against PY20 and β-Actin were from Sigma. HSP90 inhibitors 17-AAG were obtained from Selleckchem.

Cell Lines and Standard Assays

Hs578T, MDA-MB-231, DU145 and PC3 cells were purchased from the American Type Culture Collection (ATCC) and maintained according to the supplier's instructions. Lentiviral transduction, cell proliferation assays, wound healing assays, Matrigel invasion assays, Western blotting, flow cytometry and confocal image analysis were carried out as described previously (Teng, Y., et al. Br. J. Cancer 103:1066-1075 (2010); Teng, Y., et al. Int. J. Cancer 129:2825-2835 (2011); Teng, Y., et al. Oncogene 33:203-211 (2014); Teng, Y., et al. J. Biol. Chem. 287:10051-10059 (2012); Teng, Y., et al. Carcinogenesis 4:1994-1999 (2013); Teng, Y. et al. Oncogene Mar. 30 (2015)).

Immunofluorescent Staining and Quantitation of Filamentous Actin

MDA-MB-231 and PC3 cells were seeded (10,000 cells per well) on slides with the Nunc™ Lab-Tek™ II Chamber Slide™ System (Thermo Fisher Scientific) in complete medium overnight and incubated with 10 μM WAHM or scrambled peptides for 24 hours. Cells were then fixed with 3.7% formaldehyde for 15 min and permeabilized with 0.1% Triton X-100 for 10 min and incubated with Texas-red phalloidin (Life technologies) for an additional 30 min to stain actin filaments. Cells were imaged using a Zeiss LSM 410 confocal microscope equipped with ×63 (1.4 numerical aperture) oil objective (Carl Zeiss) as previously described8. To quantitate the filamentous actin, cells were seeded at 2000 cells per well in a 96 well plate and treated with WAHM or scrambled peptides for 24 hours. Cells were then stained with phalloidin as described above, followed by extensive washings. Phallodin was solubilized with methanol and the supernatant was transferred to a clear-bottom black plate, and the fluorescence was determined using Infinite® M1000 PRO (Tecan). A parallel set of cells was used to determine cell number using the CellTiter-Glo® Luminescent Cell Viability kit from Promega (Madison), according to the manufacturer's parameters. Data from three independent experiments were expressed as mean relative fluorescence units per cell ±SEM.

Immunoprecipitation Assays

Immunoprecipitation assays were carried out as described previously (Sossey-Alaoui, K., et al. J. Biol. Chem. 82:26257-26265 (2007)). Specially, to determine the physical interaction with individual peptides, MDA-MB-231 cells were pretreated with 10 μM biotin-labeled peptides for 24 hours and lysates were incubated with immobilized avidin resin overnight at 4° C. The pull down samples were subjected to SDS-PAGE followed by Western blot analysis.

Detection of MMP-9 Secretion in Culture Supernatant by ELISA Assays

After incubation with WAHM or scrambled peptides for 24 hours, MDA-MB-231 and PC3 cell supernatants were recovered and centrifuged at 1000 g at 4° C. for 20 min. MMP-9 levels in supernatants were measured using the Human MMP-9 Quantikine® ELISA kit (R&D Systems) and microplate reader at 450 nm.

Results

Loss of Either CYFIP1 or NCKAP1 Expression Leads to WASF3 Instability Resulting in Suppression of Invasion Analysis of the WASF complex suggested that the WRC proteins, and in particular CYFIP1 and NCKAP1, influence its stability (Kunda, P., et al. Curr. Biol. 13:1867-1875 (2003); Innocenti, M., et al. Nat. Cell Biol. 6:319-327 (2004)). To evaluate the importance of this complex for the stabilization of WASF3, we created shRNAs to knock down the CYFIP1 and NCKAP1 proteins in MDA-MB-231 breast cancer and PC3 prostate cancer cells. In both cases, two independent shRNAs were used and, as shown in FIG. 1, high-level suppression of protein expression was achieved in both cases. Coincident with the knockdown of either CYFIP1 or NCKAP1, WASF3 protein levels were also significantly suppressed (FIG. 1A, 1C), demonstrating that the stability of WASF3 is dependent on its interaction with these two proteins. Invasion assays demonstrated that knockdown of CYFIP1 and NCKAP1 also led to a highly significant reduction in invasion potential (FIG. 1B, 1D), consistent with the same phenotype that results from suppression of WASF3 as we have shown in these cell lines previously (Sossey-Alaoui, K., et al. Am. J. Pathol. 170: 211-221 (2007); Teng, Y., et al. Br. J. Cancer 103:1066-1075

(2010); Teng, Y., et al. Int. J. Cancer 129:2825-2835 (2011)). These data suggest that disrupting the protein-protein complex involving CYFIP1 and NCKAP1 could lead to suppression of invasion by affecting WASF3 function.

Targeting the CYFIP1-WASF Interaction with Stapled Peptides

Figure 1A:
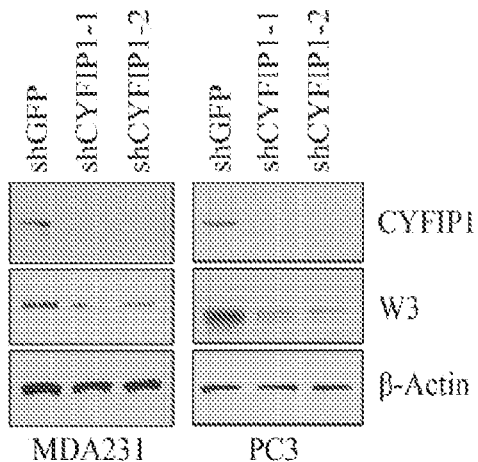
FIGS. 1A to 1D show knockdown of CYFIP1 or NCKAP1 leads to suppression of invasion. Western bot analysis following knockdown of CYFIP1 using two individual shRNAs (-1, and -2) in breast cancer MDA-MB-231 and prostate cancer PC3 cells shows loss of the CYFIP1 protein leads to concomitant loss of the WASF3 protein (FIG. 1A). As a result of CYFIP1 knockdown both breast and prostate cancer cells show significant reduction in invasion potential (FIG. 1B). In parallel experiments, knockdown of NCKAP1 using two different shRNAs also leads to reduction in WASF3 protein levels (FIG. 1C) and suppression of invasion (FIG. 1D). *$p<0.05$ and **$p<0.01$.
Figure 1B:
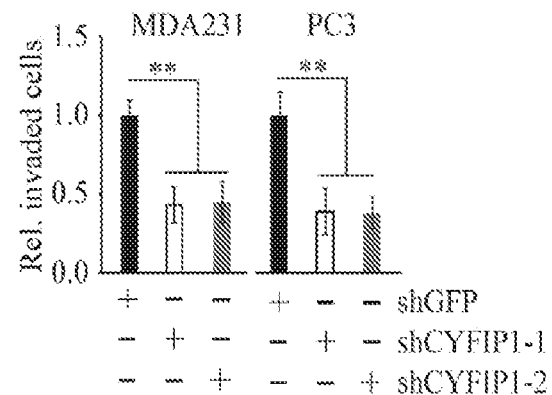
Figure 1C:
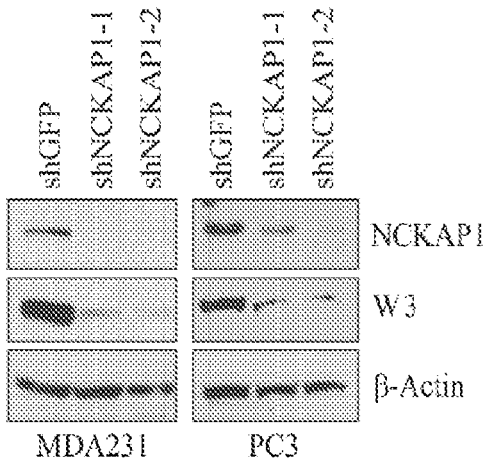
Figure 1D:
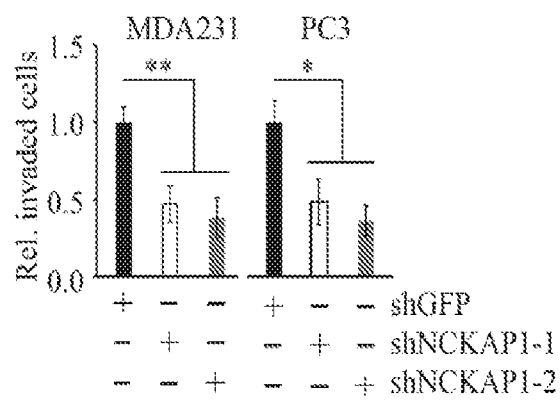
Figures 2A, 2B:
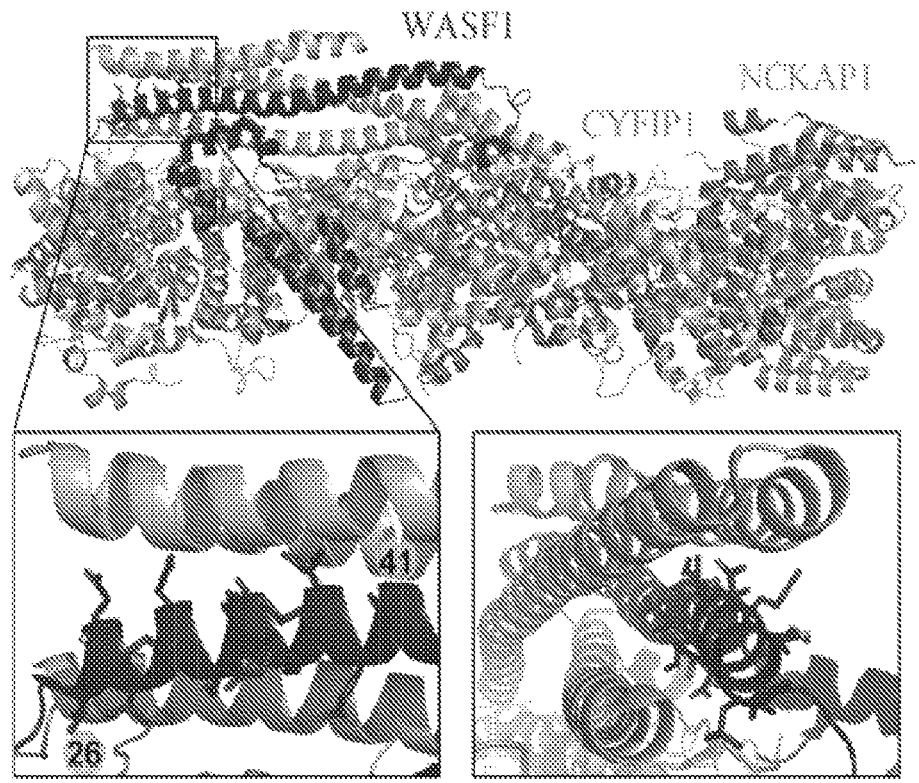
FIGS. 2A to 2D show stapled peptide design and uptake in cancer cells. The crystal structure of WASF1 in complex with CYFIP1-NCKAP1 shows the interaction surfaces derived from WASF3 and defines an α-helical surface at amino acids 26-41 in CYFIP1 that provides contact points for the two proteins (FIG. 2A). The amino acid sequence between the three members of the WASF family of proteins is highly conserved (WASF1 (SEQ ID NO:12), WASF2 (SEQ ID NO:13), WASF3 (SEQ ID NO:14)). Using the WASF3 sequence, two stapled peptides (WAHM1, SEQ ID NO:1; WAHM2, SEQ ID NO:2) were designed to target this interaction surface where diamonds represent the position of the non-natural amino acids (FIG. 2B). Scrambled peptide controls (SCR1, SEQ ID NO:3; SCR2, SEQ ID NO:4) were also generated for each WAHM peptide (FIG. 2B). MDA-MB-231 and HS578T breast cancer cells and DU145 and PC3 prostate cancer cells show cytoplasmic fluorescein labeling after 6 hours exposure to WAHM1/2 (FIG. 2C). A time course of peptide uptake using flow cytometry over the first 2 hour period of exposure shows progressive fluorescein labeling in breast and prostate cancer cells (FIG. 2D).

Using stapled peptides to target PPIs requires an α-helical interface between the target proteins, which is largely dependent on three-dimensional structural information. Although the crystal structure of WASF3 has not been established, related studies (Chen, Z., et al. Nature 468:533-538 (2010); Chen, B., et al. Cell 156:195-207 (2014)) identified a large α-helical interface between CYFIP1 and WASF1 at amino acid residues 26-41 (FIG. 2A). The amino acid sequence that forms this helix between WASF1 and CYFIP1 is virtually identical to that in WASF3 (FIG. 2A), suggesting that this region may perform the same function in both proteins. To establish whether this would serve as a target to inhibit WASF3 function and suppress invasion, inhibitors derived from this sequence were developed. These peptides are referred to as WASF Helix Mimic (WAHM) with sequences LEK*TNS*LAKIIRQL (WAHM1, SEQ ID NO:1) and LEKKTN*TLA*IIRQL (WAHM2, SEQ ID NO:2), where * indicates the position of the (S)-2-(4'-pentenyl)alanine that forms the staple (FIG. 2B). Two scrambled (SCR) peptides, SCR1: SRA*LLI*TKIQNELK (SCR1, SEQ ID NO:3) for WAHM1, and SCR2: TRAILL*ITK*QNELK (SEQ ID NO:4) for WAHM2, were also designed as negative controls for the study. All peptides were modified to contain an N-terminal 5(6)-carboxyfluorescein label for studies involving cellular uptake and intracellular location.

Figure 2C:
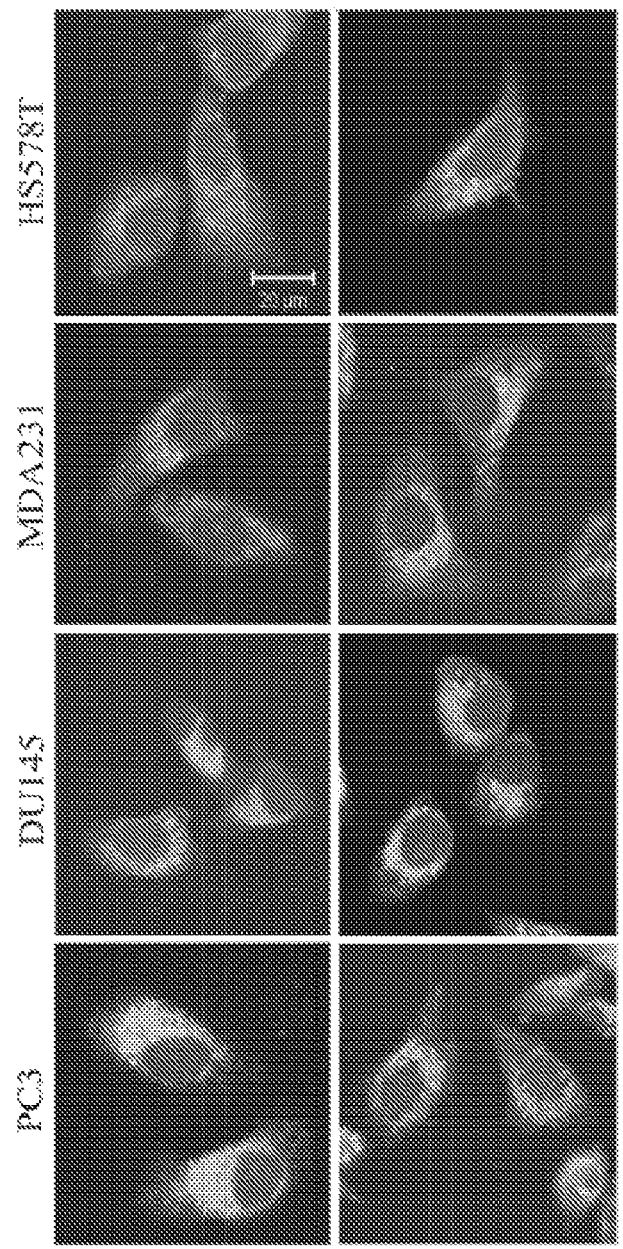
Figure 2D:
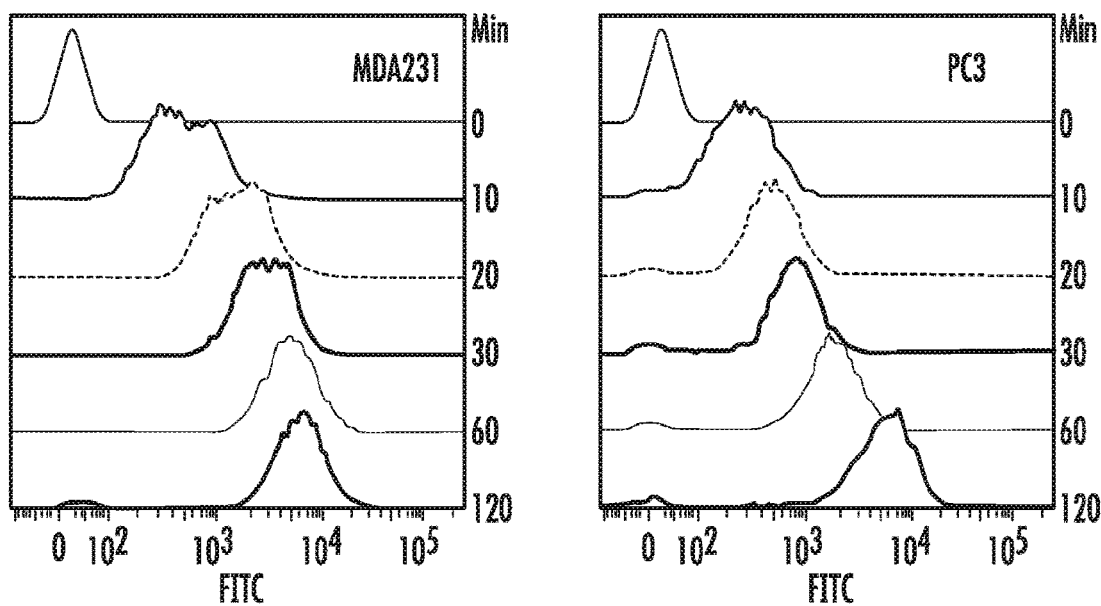

Breast cancer cells (HS587T and MDA-MB-231) and prostate cancer cells (PC3 and DU145) were exposed to WAHM1 and WAHM2 and their scramble controls at a concentration of 10 μM, and the cellular uptake was followed by assessing fluorescein levels in the cells using confocal microscopy and flow cytometry (FIG. 2C, 2D). After 6 hours, all four cell lines demonstrated high-level intracellular fluorescence, confined largely to the cytoplasm, in >80% of the cells (FIG. 2C). Monitoring uptake by flow cytometry showed a progressive increase in intracellular fluorescence over the first 2-hour exposure window (FIG. 2D). No obvious increase or decrease in fluorescence intensity was seen after 24 hours. These data demonstrate a rapid and high-level uptake of these peptides by cancer cells, as we have seen for other SPs30.

Figure 3A:
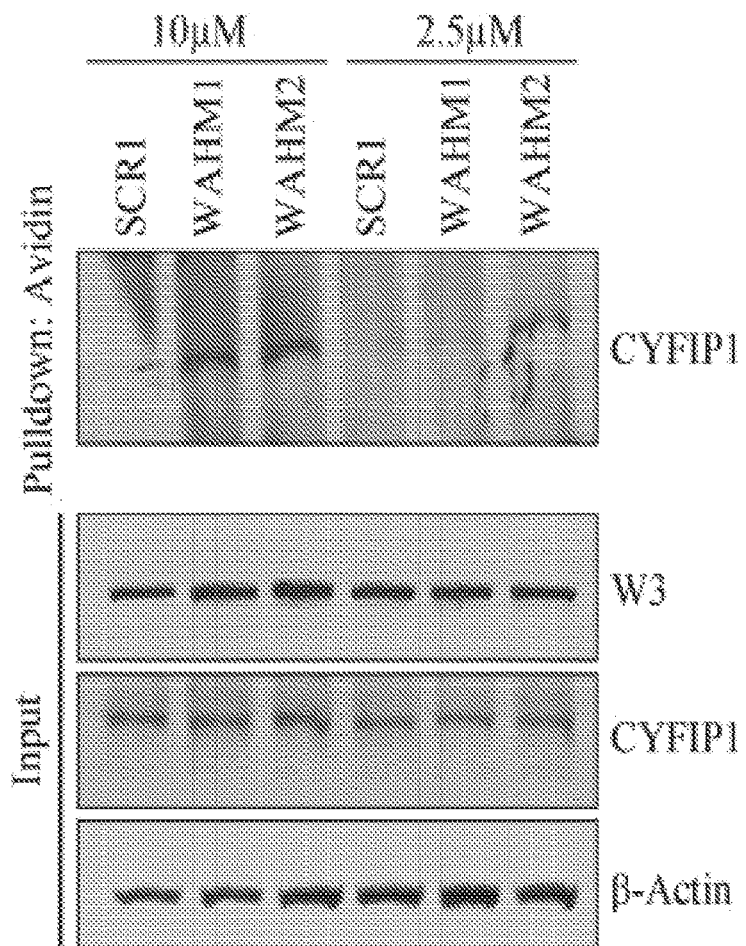
FIGS. 3A and 3B show the WAHM peptides lead to disruption of WASF3 complex. In avidin-biotin pull down assays using biotinylated stapled peptides and a concentration of 10 µM, CYFIP1 was shown to interact with WAHM1/2 but not scrambled control (SCR) peptide 1 (FIG. 3A). At lower concentrations of peptides (2.5 µM), recovery of CYFIP1 was reduced. Treatment with WAHM1/2 did not affect intracellular levels of either WASF3 or CYFIP1. In an IP of WASF3, following treatment with WAHM1/2 (FIG. 3B), CYFIP1 was not present in the immunocomplex, demonstrating that WAHM1/2 leads to disruption of the complex without affecting the protein levels.
Figure 3B:
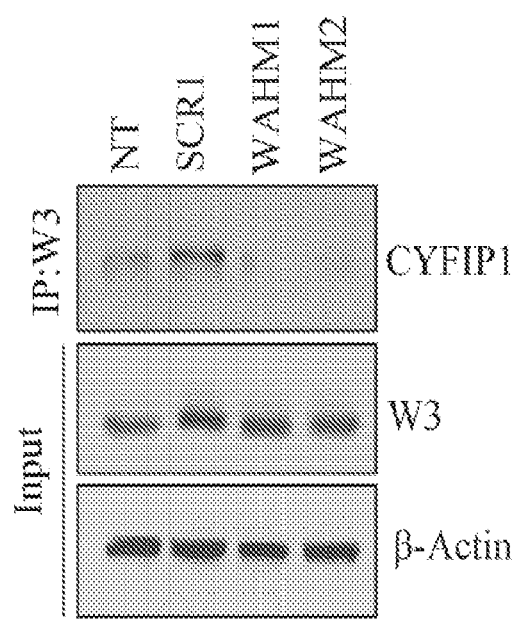

To determine whether the SPs formed a complex with WASF3 within the cells, MDA-MB-231 cells were exposed to biotinylated WAHM1 and WAHM2 for 6 hours, after which the cells were lysed and pull down assays were performed using avidin-coated beads. As shown in FIG. 3A, WASF3 protein levels were not affected by the SPs, whether they were treated for short (2 hours) or longer (24 hours) periods (FIG. 7). However, CYFIP1 was present in the pull down complex with both WAHM1 and WAHM2 but not the SCR peptides, in a concentration-dependent manner (2.5 μM versus 10 μM) (FIG. 3A). IP of WASF3 from these cells demonstrated that CYFIP1 was not present in cells treated with the two SPs (FIG. 3B), further demonstrating that the peptides target this protein complex.

Role of WASF Family Members in Invasion

Figure 4A:
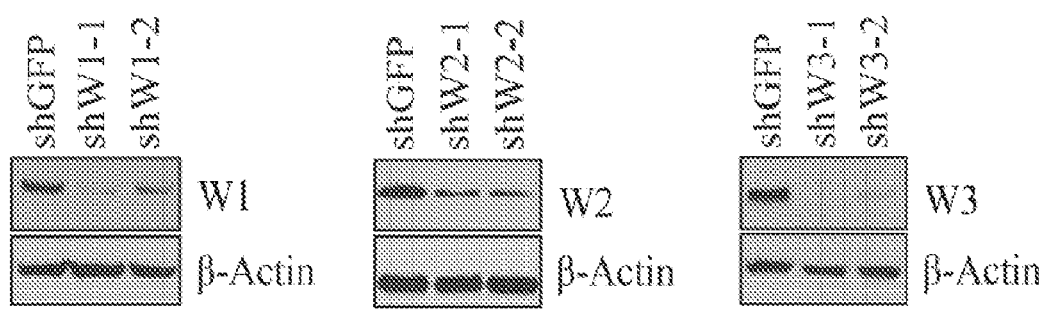
FIGS. 4A to 4C show loss of WASF1 and WASF2 does not suppress cancer cell invasion. Two independent shRNAs were used to individually knockdown WASF1, WASF2, and WASF3 in MDA-MB-231 cells (FIG. 4A). As a result of the knockdown for any of the three genes there was no change in proliferation compared to control knockdown cells (shGFP) (FIG. 4B). Transwell invasion assays showed a marked suppression of invasion potential in WASF3 knockdown cells but not in WASF1 or WASF2 knockdown cells (FIG. 4C). **$p<0.01$.
Figure 4B:
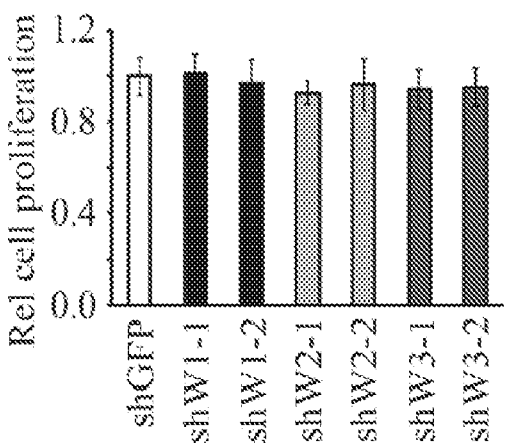
Figure 4C:
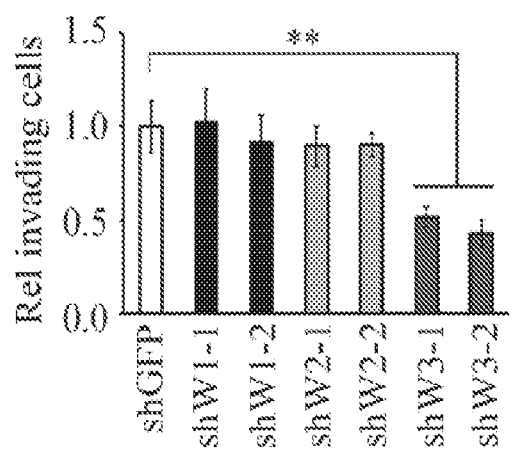

The experiments described above show that CYFIP1 and NCKAP1 interact with WASF3, and that loss of any of these three proteins leads to loss of invasion in cancer cells. The CYFIP1 and NCKAP1 proteins, however, also interact with WASF1 and WASF2, and so the SPs that affect WASF3-mediated invasion may also affect the function of these other family members as well. To date, however, there is little evidence associating WASF1/2 with invasion/metastasis, unlike the strong association with WASF3 for this phenotype that has been clearly demonstrated. Since it is possible that WAHM1 and WAHM2 may also target WASF1/2 function, experiments were conducted to determine whether this outcome would have a contribution to the suppression of invasion. To evaluate this possibility, shRNAs were used to knock down both WASF1 and WASF2 in breast cancer MDA-MB-231 cells and compared the effects on invasion with WASF3 knockdown cells. For these studies, two independently derived knockdown populations were developed for all three family members using two different shRNA constructs for each gene (FIG. 4A). As shown in FIG. 4B, there was no effect on proliferation following knockdown of any of the three WASF proteins. Using Transwell invasion assays, there was no significant suppression of invasion potential as a result of knockdown for WASF1 or WASF2 compared with the knockdown control cells (FIG. 4C). In contrast, there was a significant reduction in invasion potential when WASF3 was knocked down (FIG. 4C), as seen in previous reports (Sossey-Alaoui, K., et al. Am. J. Pathol. 170:211-221 (2007); Teng, Y., et al. Br. J. Cancer 103:1066-1075 (2010); Teng, Y., et al. Int. J. Cancer 129:2825-2835 (2011)).

These observations suggest that, in the cell systems analyzed, WASF1 and WASF2 do not play a significant role in controlling cancer cell invasion and migration phenotypes (FIG. 4) and therefore, it is unlikely that the specific invasion-suppressive effect produced by WAHM1 and WAHM2 are a result of targeting functional protein-protein interactions involving the other WASF family members.

WAHM1/2 Suppresses Cancer Cell Motility Through Targeting the WASF3/CYFIP1 Interaction Since the stapled peptides are reasonably stable for at least 24 hours within the cell, their effect was investigated on short-term cell motility, proliferation and invasion. Using MTS assays, there was no significant difference in cell proliferation in either breast or prostate cancer cells treated with either WAHM1 or WAHM2, or the scrambled peptides at a 10 μM concentration over 24 hours (FIG. 8).

Figure 5C:
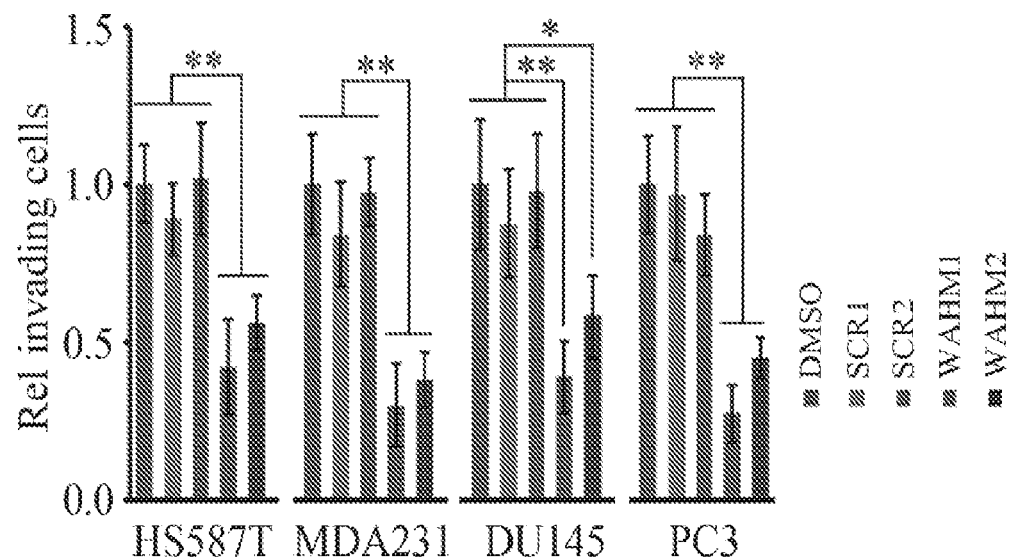

As decreased cell motility is associated with increased stress fiber formation following loss of WASF3 function (Teng, Y., et al. Br. J. Cancer 103:1066-1075 (2010); Sossey-Alaoui, K., et al. J. Biol. Chem. 82:26257-26265 (2007)), experiments were conducted to determine whether the SPs affected organization of the microfilament network by using Phalloidin-binding assays to visualize the effects on polymerized F-actin. MDA-MB-231 and PC3 cells treated with the SCR peptides were indistinguishable from untreated cells, showing only marginal stress fiber formation. F-actin cables were thin and highly unorganized (FIG. 9A). Following treatment with either WAHM1 or WAHM2, the actin cytoskeleton became more organized, resulting in an increase in both the number and thickness of the actin stress fibers (FIGS. 5A and 9A) showing that disrupting the CYFIP1-WASF interaction increases actin polymerization levels, which is also a feature of WASF3 knockdown cells. Since deregulation of the cytoskeleton is associated with altered cancer cell motility, we next determined the effects of the SPs on cancer cell migration and invasion. Using the scratch wound assay, treatment of breast and prostate cell lines led to reduced migration potential (FIGS. 5B and 9B), which is consistent with previous observations following shRNA knockdown of WASF3 (Sossey-Alaoui, K., et al. Am. J. Pathol. 170:211-221 (2007); Teng, Y., et al. Br. J. Cancer 103:1066-1075 (2010); Teng, Y., et al. Int. J. Cancer 129:

2825-2835 (2011)). Transwell invasion analysis over 24 hours following treatment with 10 µM WAHM1 or WAHM2 resulted in a reduction (~50-75%) of invasion potential, compared with cells treated with either the SCR peptides or DMSO (FIGS. 5C and 9C). The equivalency of this effect between DMSO and SCR treatment demonstrates that neither SCR control peptide had any significant effect on the invasion phenotype. These data demonstrate that targeting the CYFIP1-WASF interaction with SPs affects cancer cell cytoskeleton organization, motility and invasion, consistent with knockdown of WASF3 function achieved by other means.

WAHM Treatment Leads to Loss of WASF3 Activation

Knockdown of either CYFIP1 or NCKAP1 leads to loss of the WASF3 protein (FIG. 1). Analysis of WASF3 in the SP treated cells, however, showed that there was no change in protein levels compared with the control treated cells (FIGS. 3 and 7). Thus, it appears that targeting the WASF3 complex with WAHM1/2 does not lead to degradation of the complex seen following genetic knockdown of any of the three proteins, even though invasion and migration are dramatically affected. The same response was seen for the other WASF family members, where SP treatment did not affect WASF1 or WASF2 protein levels (FIG. 6D). Since WASF3 function has been shown to be dependent on its phosphoactivation (Sossey-Alaoui, K., et al. J. Biol. Chem. 82:26257-26265 (2007); Teng, Y., et al. J. Biol. Chem. 287:10051-10059 (2012); Teng, Y., et al. Carcinogenesis 4:1994-1999 (2013)), experiments were conducted to determine whether the phosphorylation status of WASF3 was affected following treatment with WAHM1 or WAHM2. IP analysis showed that treatment of MDA-MB-231 cells with either WAHM1 or WAHM2 led to a dramatic decrease in WASF3 phosphorylation levels (FIG. 6A), without a reduction in WASF3 protein levels. The same effect was observed in PC3 prostate cancer cells. These data demonstrate that it is the loss of WASF3 function through activation resulting from SP treatment, which accounts for the suppression of invasion. Inactivation of HSP90 with 17-AAG also leads to reduced WASF3 phosphoactivation due to suppression of ABL kinase function14. Treatment with the SPs, however, showed that suppression of WASF3 activation was far more significant (FIG. 6B) than that seen following 17-AAG treatment.

Phosphoactivation of WASF3 is induced by treatment with growth factors and cytokines (Teng, Y., et al. Carcinogenesis 4:1994-1999 (2013); Sossey-Alaoui, K., et al. Exp. Cell Res. 308:135-145 (2005)). Thus, in cells cultured in serum, there is a consistent subpopulation of the WASF3 protein that is activated as determined by its relocation to the leading edge of invading cells. In starved cells, however, WASF3 activation is virtually undetectable (FIG. 10). To study the effect of the SPs on activated WASF3, we starved MDA-MB-231 and PC3 cells overnight and then treated them for 4 hours. As shown in FIG. 6C, in the absence of serum-derived growth factors, WASF3 levels are reduced beyond detectable levels following SP treatment compared with non-treatment and scrambled peptide treatment. These data suggest that the inactivated form of WASF3 is more susceptible to degradation following disruption of the CYFIP1-WASF3 complex (FIG. 6C).

WASF3 expression is inversely related to expression of the KISS1 metastasis suppressor gene and knockdown of WASF3 in breast and prostate cancer cells leads to increased levels of KISS1 (Teng, Y., et al. Int. J. Cancer 129:2825-2835 (2011); Teng, Y., et al. Oncogene 33:203-211 (2014)). This effect was also observed when cells were treated with either WAHM1 or WAHM2 (FIG. 6D), further supporting the conclusion that the critical effect of these SPs is to disrupt WASF3 function.

WAHM1/2 Suppresses WP9 Secretion Through Inactivation of WASF3

Figure 6E:
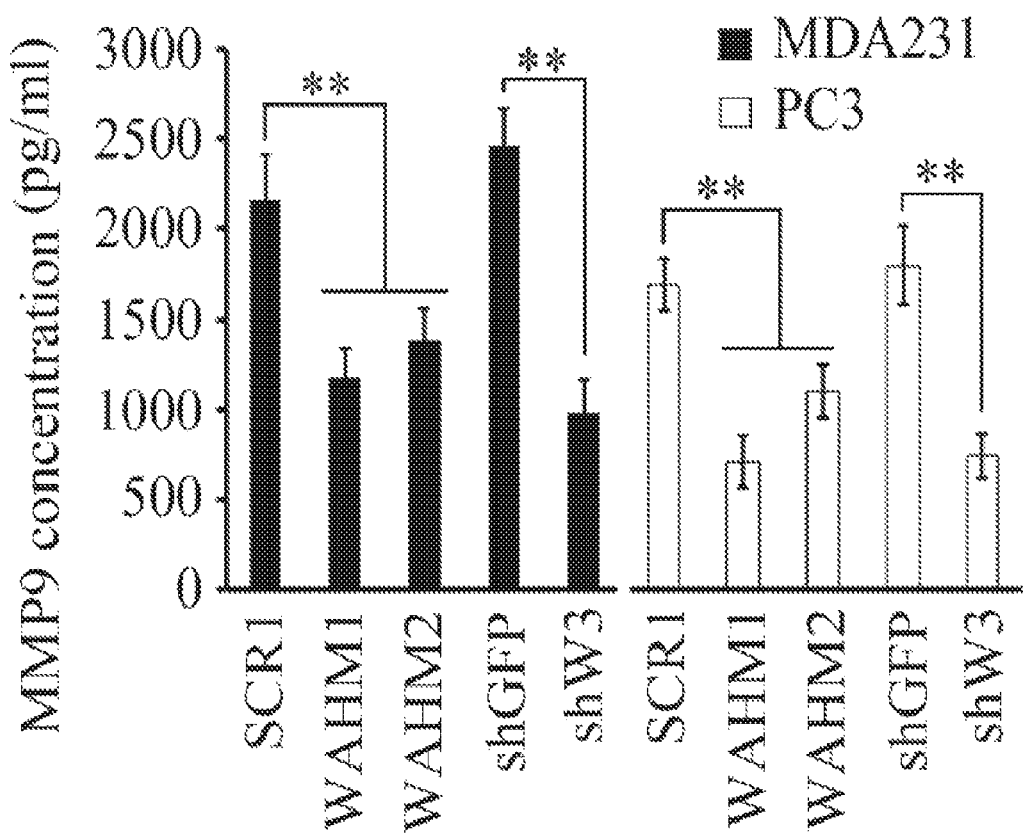

The effect of WASF3 on invasion was associated with downregulation of the KISS1 metastasis suppressor gene in breast and prostate cancer cells (Teng, Y., et al. Int. J. Cancer 129:2825-2835 (2011); Teng, Y., et al. Oncogene 33:203-211 (2014)). This effect was not seen in WASF1- or WASF2-depleted cells (Teng, Y., et al. Int. J. Cancer 129:2825-2835 (2011)). Moreover, knockdown of WASF3 led to downregulation of MMP-9 expression and secretion through repression of KISS1-mediated NFkB signaling (Teng, Y., et al. Int. J. Cancer 129:2825-2835 (2011)). As expected, Western blot analysis of MDA-MB-231 cells treated with WAHM1 or WAHM2 showed increased KISS1 levels, which is consistent with the effect seen in WASF3 knockdown cells (FIG. 6D). When MDA-MB-231 and PC3 cells were treated with WAHM1 or WAHM2, there was a remarkable reduction in secreted MMP9 levels by the cancer cells compared with treatment with the scrambled controls (FIG. 6E). Collectively, these results indicate that disruption of the CYFIP1-WASF complex leads to suppression of MMP9 secretion through inhibition of the WASF3-KISS1 signaling cascade.

Discussion

One of the challenges in exploring strategies to increase survival in cancer patients is to devise a means of suppressing the most lethal aspect of the disease that results from metastatic progression. Overexpression of WASF3 is correlated with high-grade breast and prostate cancer (Kulkarni, S., et al. PLoS One 7:e42895 (2012); Teng, Y., et al. Br. J. Cancer 103:1066-1075 (2010); Prat, A., et al. Breast Cancer Res. 12:R68 (2010)), and experimental evidence to date suggests that its inactivation leads to suppression of invasion and metastasis, in several model cell systems (Sossey-Alaoui, K., et al. Am. J. Pathol. 170:211-221 (2007); Teng, Y., et al. Br. J. Cancer 103:1066-1075 (2010); Teng, Y., et al. Int. J. Cancer 129:2825-2835 (2011); Teng, Y., et al. Oncogene 33:203-211 (2014)), raising the possibility that targeting its function may provide a means of suppressing metastasis. The present study supports this idea, where specific targeting of WASF3 function using stapled peptides affecting the protein-protein interaction between WASF3 and CYFIP1 disrupts WASF3 activity and suppresses the invasion phenotype.

Genetic knockdown of either CYFIP1 or NCKAP1 leads to a reduction in WASF3 protein levels, which leads to suppression of invasion, demonstrating a functional consequence of disrupting of the WRC complex. In the absence of the CYFIP1 or NCKAP1 proteins, WASF3 protein levels are almost completely lost, demonstrating the importance of these interactions in maintaining the stability of the complex and underscoring the importance of the CYFIP1-NCKAP1 dimer in maintaining the function of the WASF3 protein. In contrast, however, targeting the interface between CYFIP1 and WASF3 (amino acids 21-46) with the stapled peptides, does not apparently affect WASF3 protein levels, but rather prevents phosphoactivation, which is absolutely required for invasion (Sossey-Alaoui, K., et al. J. Biol. Chem. 82:26257-26265 (2007); Teng, Y., et al. J. Biol. Chem. 287:10051-10059 (2012); Teng, Y., et al. Carcinogenesis 4:1994-1999 (2013)). These observations may indicate that the SPs create partial disruption of the interface between these two proteins at the targeted site, which prevents phosphoactivation, rather than disrupting the overall protein complex and triggering its degradation. These observations are consistent with previous reports that preventing phosphoactivation of WASF3, either by targeting critical activating kinases, or destabilizing them, leads to the same loss of the invasion phenotype (Sossey-Alaoui, K., et al. J. Biol. Chem. 82:26257-26265 (2007); Teng, Y., et al. J. Biol. Chem. 287:10051-10059 (2012); Teng, Y., et al. Carcinogenesis 4:1994-1999 (2013)). In the absence of serum, WASF3 exists in an unphosphorylated, inactive form associated with absence of cell motility. WAHM1/2 leads to loss of WASF3 protein, implying that phosphoactivation protects the WASF3 protein from degradation, even in the absence of bound CYFIP1 and NCKAP1.

WASF1 and WASF2 have also been implicated in cell movement through regulation of other membrane structures such as membrane ruffles (Takenawa, T., et al. Nat. Rev. Mol. Cell Biol. 8:37-48 (2007)). While it might be expected that targeting the CYFIP1-WASF3 interface may also affect the function of the other two WASF family members, in a side-by-side comparison of the same cell types that respond to WASF3 loss, neither of these family members are required for cancer cell invasion. The SPs therefore, specifically target this phenotype through regulation of WASF3 function. These observations further support a specific role for the WASF3 family member in the regulation of invasion and metastasis.

Knockdown of CYFIP1 in highly invasive cancer cells leads to suppression of invasion due to its regulatory role over WASF3. It was suggested in a previous study (Silva, J. M., et al. Cell 137:1047-1061 (2009)), however, that CYFIP1 may have a tumor suppressive function, although these studies were largely performed in normal MCF10A breast cells, which may provide a different context for the function of CYFIP1 and in its interactions with other members of the WASF family, in particular WASF2, which does not influence invasion in highly metastatic cells. It is possible, therefore, that CYFIP1 may have different effects in normal cells that result from a disruption of the functional interaction with WASF1 and WASF2, but CYFIP1 is required to engage in the WASF3 complex to promote cancer cell invasion in different cell types.

Targeting the CYFIP1-WASF3 interaction leads to suppression of invasion as well as downregulation of invasion-related signaling cascades that were previously reported to be WASF3-dependent, including regulation of KISS1 and MMP9 levels as a result of WASF3 phosphoactivation. Thus, from a molecular and functional standpoint, the SPs can effectively suppress invasion by suppressing WASF3 signaling using levels of suppression of invasion only ~50-75%, compared with an 80-90% knockdown achieved with the best performing shRNAs.

The selected target for the WASF3 SPs was based on the trimeric crystallographic structure of CYFIP1-NCKAP1-WASF1. This interaction is highly conserved between the WASF1 and WASF2 proteins, which might suggest that these SPs could also affect the function of the other two family members. While there may be unknown effects as a result of affecting WASF1/2 function, these do not manifest into changes in cell proliferation or invasion, since knockdown of either WASF1 or WASF2 individually did not lead to a change in invasion in the cancer cell types studied. It appears, therefore, that WASF3 function is specifically related to invasion and that this relies on an interaction with the CYFIP1-NCKAP1 complex. WASF1 and WASF2 have also been implicated in regulating cell movement through influencing other membrane structures such as ruffles and filopodia (Suetsugu, S., et al. Dev. Cell 5:2595-2609 (2003); Beli, P., et al. Nat. Cell. Biol. 10:849-857 (2008)) but it is clear from the knockdown studies that these membrane structures do not have a significant effect on invasion or metastasis. As a result, targeting of the CYFIP1-NCKAP1-WASF3 complex may provide some specificity for approaches designed to target WASF3 in order to achieve suppression of invasion and metastasis.

Example 2: The WASF3-NCKAP1-CYFIP1 Complex is Essential for Breast Cancer Metastasis Methods Cell Culture and Standard Assays MDA-MB-231, Hs578T and T47D breast cancer cell lines were obtained directly from American Type Culture Collection (Rockville, Md.). MDA-MB-231 and T47D and have been verified using SNP-CGH (Teng Y, et al. Int J Cancer 2011 129:2825-2835) for characteristic cytogenetic changes. The ATCC Cell Authentication Testing service confirmed the identity of Hs578T using STR DNA fingerprinting analysis. Standard cell culture, transient transfections, RT-PCR, western blotting, immunoprecipitation (IP), flow cytometry, Biotin-Avidin pulldown, lentiviral transduction, cell proliferation and Transwell invasion assays were carried out as described previously (Teng Y, et al. Int J Cancer 2011 129:2825-2835; Teng Y, et al. J Biol Chem 2012 287:10051-10059; Teng Y, et al. Carcinogenesis 2013 34:1994-1999).

DNA Constructs, Antibodies and Other Reagents

Lentiviral pCDH-CMV-MCS-EF1-PURO-HA-WASF3 (pCDH-HA-WASF3) was generated as described previously (Teng Y, et al. Carcinogenesis 2013 34:1994-1999). To construct the HA-NCKAP1 overexpression vector, the full-length human NCKAP1 was amplified from the template NCKAP1 cDNA clone (OriGene, Rockville, Md.) and was inserted into pCDHCMV-MCS-EF1-GFP lentiviral vector (System Biosciences, Mountain View, Calif.) as described previously (Teng Y, et al. Oncogene 2014 33:203-211). To stably knock down NCKAP1, pLKO.1 lentiviral vectors harboring shRNA-targeting NCKAP1 were obtained from Open Biosystems (Huntsville, Ala.). pcDNA3-EGFP-RAC1-T17N (RAC1DN) was a gift from Dr. Gary Bokoch (Addgene plasmid #12982). The RAC1 NSC24766 inhibitor was obtained from Selleckchem (Houston, Tex.). For western blot and IP assays, the following primary antibodies were used: NCKAP1, WASF1 (Abcam, Cambridge, Mass.), WASF2, WASF3 (Cell Signaling Technology, Beverly, Mass.), HA, GST, RAC1, β-Actin (Sigma, St Louis, Mo.).

Glutathione S-Transferase (GST) Fusion Protein Interaction Assays

To determine the interaction between NCKAP1 and WASF3, GST-fusion protein pulldown assays were performed as described previously (Sossey-Alaoui K, et al. J Biol Chem 2005 280:21748-21755; Dong C, et al. Traffic 2012 13:857-868). A GST-WASF3 (GST-W3) fusion protein was expressed in BL21 bacteria and purified using MagneGST glutathione particles (Promega, Madison, Wis.). Once the correct size protein was confirmed by Coomassie Brilliant Blue staining following SDS-PAGE, the immobilized fusion protein was used immediately. Cell lysates from MDA-MB-231 cells that had been transfected with a pCD-HCMV-MCS-EF1-PURO-NCKAP1 construct were incubated in 500 µl of binding buffer (20 mm Tris-HCl, pH 7.5, 140 mm NaCl, 1% Nonidet P-40 and 0.5% BSA) with the GST fusion protein tethered to the glutathione particles for 4 h at 4° C. Precipitates were resolved by SDS-PAGE and analyzed by western blotting.

Protein Complementation Assays (PCAs)

To identify the interaction of NCKAP1 with WASF3 in live cells, PCAs were performed as described previously (Zhang X, et al. J Pharmacol Exp Ther 2009 330:109-117). In brief, expression vectors encoding NCKAP1 and WASF3 fused to N- and C-terminal fragments of GFP were constructed respectively. The NCKAP1-venus1 (NCKAP1-v1) and WASF3-venus2 (WASF3-v2) constructs were either transiently transfected individually or co-transfected into MDA-MB-231 cells and 12 hours after transfection, GFP was detected by fluorescence microscopy (Carl Zeiss, Jena, Germany).

In Vivo Tumor Growth and Metastasis Analysis

All experimental procedures were approved by the Institutional Animal Care and Use Committee (IACUC) of Georgia Regents University. Six-week-old female NSG (NOD.Cg-Prkdcscid Il2rgtm1Wjl/SzJ) mice were purchased from the Jackson Laboratory (Bar Harbor, Me., USA) and maintained in accordance with IACUC guidelines. The animal experiments were performed using the NSG mouse model as described previously. The mice were euthanized on day 56 post-injection and dissected tumors were individually weighed. The lungs were also removed from these mice and the number of nodules on the surface of the lungs was counted. For histological analyses, the lungs were fixed in 10% neutral buffered formalin, embedded in paraffin blocks, sectioned at 5 and subjected to hematoxylin and eosin (H&E) staining.

Peptide Synthesis

Peptides were synthesized on rink amide MBHA resin using 9-fluorenylmethoxycarbonyl (Fmoc) solid phase synthesis in 1-methyl-2-pyrolidinone (NMP). Fmoc protecting groups were removed using 25% (v/v) piperidine in NMP for 20-30 min. For couplings using standard N-α-Fmoc protected amino acids, 10 equivalents were added (0.25 M final concentration) along with 2-(6-chloro-1H-benzotriazole-1-yl)-1,1,3,3-tetramethylaminium hexafluorophosphate (HCTU, 0.23 M final concentration) and 8% (v/v) N,N-diisopropyl ethylamine (DIEA) in NMP. (S)—N-Fmoc-2-(4'-pentenyl) alanine couplings were performed using 4 equivalents. The ring-closing metathesis (RCM) reaction was performed prior to addition of N-terminal labeling using 0.4 equivalents bis(tricyclohexylphosphine) benzylidine ruthenium(IV) dichloride (1st generation Grubbs Catalyst, Sigma) in 1,2-dichloroethane (DCE) for two 1-hour reaction periods with agitation.

Prior to N-terminal labeling, β-alanine was added to the N-terminus of all peptides before the addition of 5(6)-carboxyfluorescein. N-terminal fluorescein labeling was performed using 2 equivalents of 5(6)-carboxyfluorescein (Acros) in DMF along with 0.046 M HCTU and 2% (v/v) DIEA. Resin cleavage was performed using a solution containing 95% trifluoroacetic acid, 2.5% water and 2.5% triisopropylsilane (Sigma) for 4 hours at room temperature. Peptides were precipitated in methyl-tert-butyl ether at 4° C. and lyophilized. Peptides were purified by high-performance liquid chromatography (HPLC) and verified by ESI mass spectrometry (ESI-MS). Fluorescein-labeled peptides were quantified by measuring the absorbance of 5(6)-carboxyfluorescein at 495 nm. Absorbance values were measured using a Synergy 2 microplate reader (Bio-Tek). The masses of the purified peptides are as follows: WANT1=1849.5 (expected mass=1849.0), WANT2=2014.5 (expected mass=2015.2), WANT3=1848.6 (expected mass=1849.1), WANT3 scr=1848.6 (expected mass=1849.1).

Results

The NCK/NCKAP1 Complex Interacts with WASF3

Figure 12A:
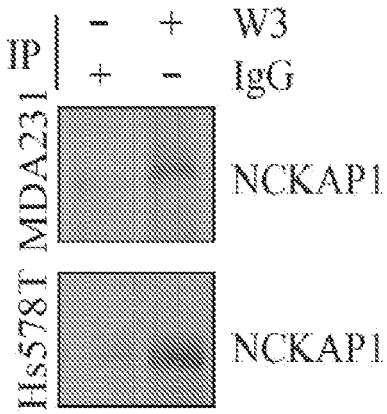
Figure 12B:
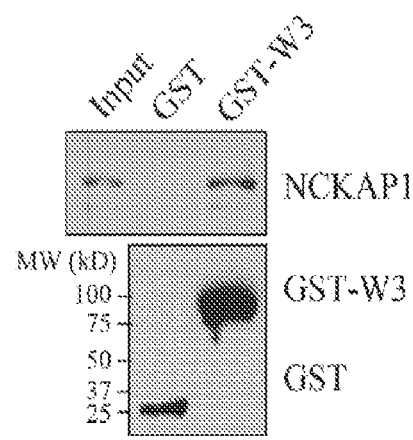
Figure 12C:
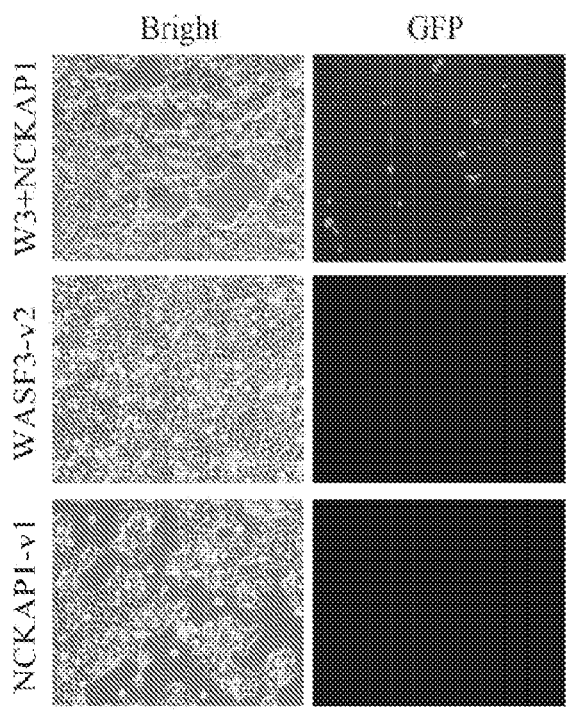
Figure 12D:
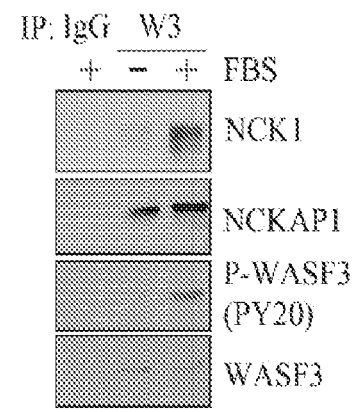

WASF3 is essential for invasion and metastasis in different cancer cell types and an analysis of the proteins specifically in the WASF3 immunocomplex using Mass Spectroscopy showed the presence of the NCK associated protein 1 (NCKAP1) (FIG. 18). Immunoprecipitation (IP) analysis of the WASF3 immunocomplex from MDA-MB-231 and Hs578T cells confirmed the presence of NCKAP1 (FIG. 12A). To further validate the interaction between NCKAP1 and WASF3, a GST-WASF3 fusion protein was immobilized on glutathione-agarose and incubated with lysates from NCKAP1 overexpressing MDA-MB-231 cells. In these pull-down assays, NCKAP1 was recovered using the GST-WASF3 fusion protein, but not GST alone (FIG. 12B), indicating that NCKAP1 indeed interacted with WASF3. To observe the intracellular interaction between NCKAP1 and WASF3, protein-fragment complementation (PCA) assays were performed based on split green fluorescent protein (GFP). Interestingly, the GFP signal was identified at the plasma membrane when NCKAP1-v1 and WASF3-v2 were co-transfected into MDA-MB-231 cells, while no fluorescence was observed when either construct was transfected alone (FIG. 12C). IP analysis showed that serum starvation strongly suppressed WASF3 phosphorylation, without affecting the engagement of NCKAP1 in the WASF3 complex (FIG. 12D).

The NCK1 protein consists exclusively of SH2/SH3 domains (Li W, et al. Mol Cell Biol 1992 12:5824-5833) and is the target of several cell surface tyrosine kinase receptors. It was shown that ligand binding activates NCK1 by phosphorylation, and that this event signals to downstream effectors that have consequences for cell motility (Rivera G M, et al. Proc Natl Acad Sci USA 2006 103:9536-9541; Lebensohn A M, et al. Mol Cell 2009 36:512-524; Zhang G, et al. J Biol Chem 2014 289:23112-23122). Growth factors such as PDGF and cytokines such as IL-6 activate WASF3 leading to increased migration and invasion and that it is recruited to the cell membrane to facilitate actin reorganization at leading edges of the cell (Sossey-Alaoui K, et al. J Biol Chem 2007 282:26257-26265; Teng Y, et al. Carcinogenesis 2013 34:1994-1999; 10, Sossey-Alaoui K, et al. Am J Pathol 2007 170:2112-2121; Teng Y, et al. JAKSTAT 2014 3:e28086). IP analysis of the WASF3 immunocomplex in starved cells, however, did not identify NCK1 (FIG. 12D).

NCKAP1 is Required for WASF3 Protein Stability and Invasion Potential

Figure 13A:
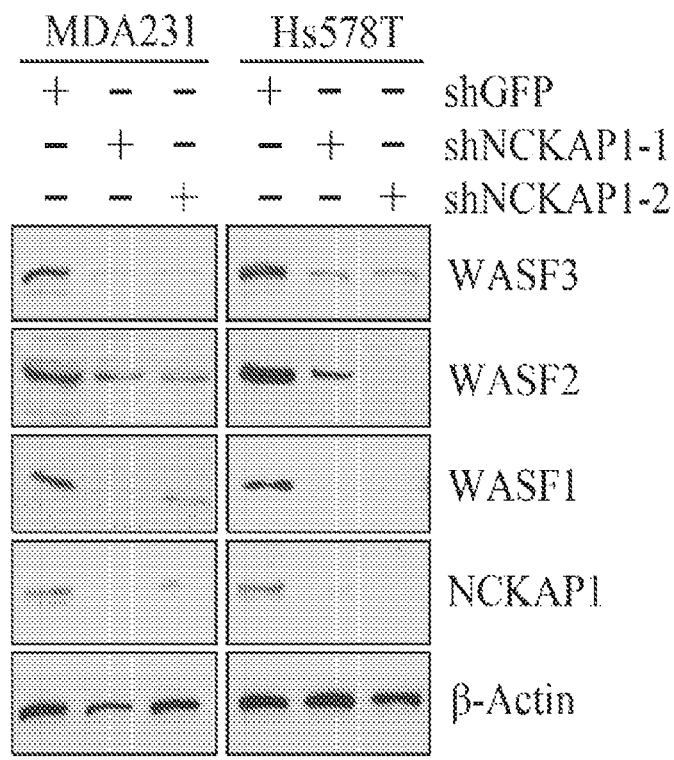
Figure 13B:
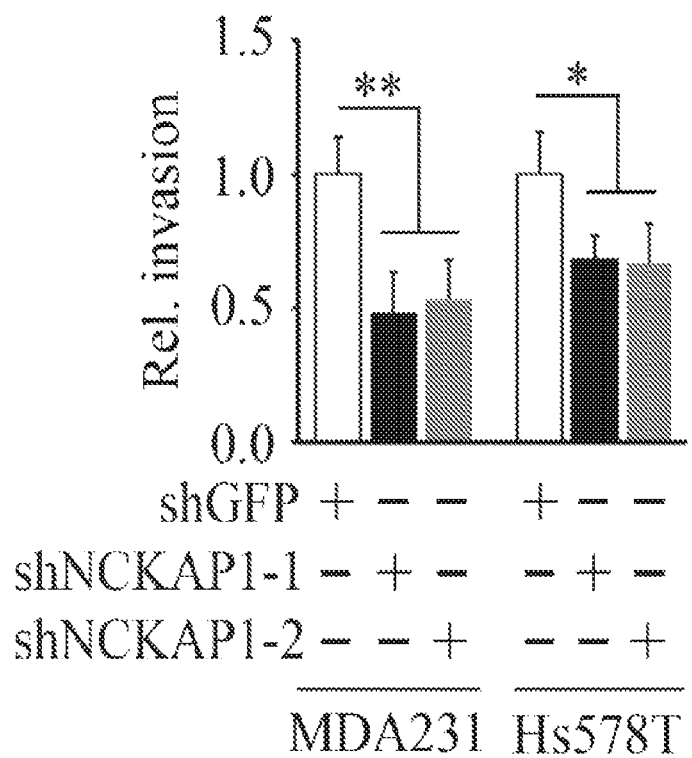
Figure 13C:
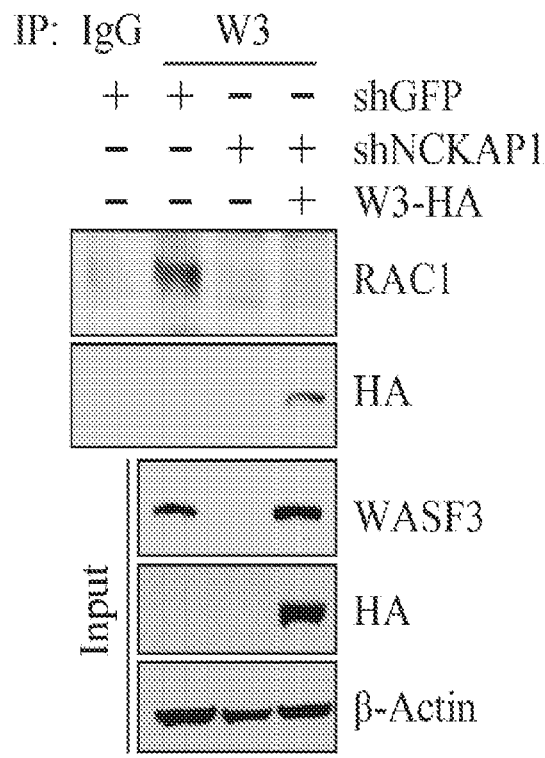
Figure 13D:
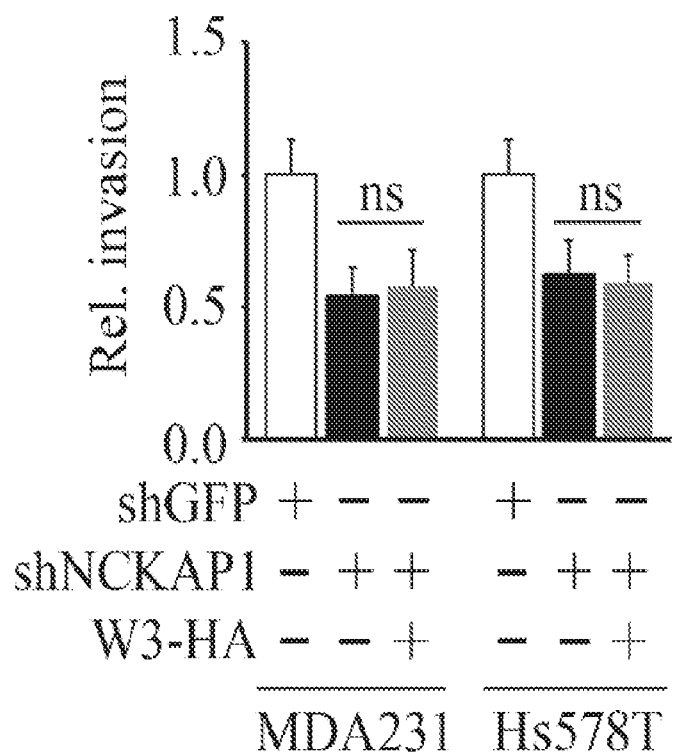

To investigate this relationship between NCKAP1 and WASF3, shRNA constructs were used to suppress NCKAP1 expression in MDA-MB-231 and Hs578T cells (FIG. 13A). Using two different shRNA constructs, knockdown of NCKAP1 led to a reduction in WASF3 protein levels (FIG. 13A), while not affecting its transcript levels (FIG. 19), supporting the idea that NCKAP1 protects WASF3 from degradation. Since NCKAP1 is also found in complex with other members of the WASF family (Nakao S, et al. J Cell Biol 2008 182:395-410; Le J, et al. Curr Biol 2006 16:895-901), the effect of its knockdown on their protein levels was analyzed. In this case, levels of both WASF1 and WASF2 were also reduced in MDA-MB-231 and Hs578T cells (FIG. 13A), demonstrating that NCKAP1 is also required for the stability of these proteins. Knockdown of WASF1 and WASF2 in MDA-MB-231 cells, however, does not affect their invasion potential. Knockdown of NCKAP1 in both MDA-MB-231 and Hs578T cells leads to a significant reduction in invasion (FIG. 13B), but does not affect cell proliferation (FIG. 20). The Rho-GTPase, RAC1, facilitates actin remodeling at the cell periphery by relaying signals to WASF proteins, leading to activation of Arp2/3-mediated actin polymerization (Steffen A, et al. EMBO J. 2004 23:749-759). To determine whether depletion of NCKAP1 abrogates the interaction with RAC1 with the WASF3 complex, an HA-tagged WASF3 construct was transfected into the NCKAP1 knockdown MDA-MB-231 cells. IP analysis in these cells using WASF3 antibodies showed that RAC1 was not co-immumoprecipitated with the exogenous WASF3 protein (FIG. 13C), indicating that RAC1 is not recruited to the WASF3 complex in the absence of NCKAP1. Moreover, suppression of invasion in NCKAP1 knockdown cells was not reversed by forced expression of WASF3 (FIG. 13D). Thus, NCKAP1 is essential for the RAC1 interaction with the WASF3 complex to promote cell invasion.

Knockdown of NCKAP1 Suppresses Metastasis in Breast Cancer Cells In Vivo

To relate the in vitro observation that links NCKAP1 expression with invasion to clinical parameters, the correlation between NCKAP1 expression and survival of patients with breast cancer was evaluated. An online gene profiling database was used to compare NCKAP1 expression levels with relapse-free survival data from 3,554 cancer patients by stratifying patients based on relative NCKAP1 expression levels as described (Gao Y, et al. Proc Natl Acad Sci USA 2004 101:7618-7623). Univariate survival analysis (Kaplan-Meier method and log-rank test) revealed that high NCKAP1 expression significantly correlates with poor, relapse-free, survival (FIG. 14A), which is likely to be related to its involvement in metastasis.

Figure 14D:
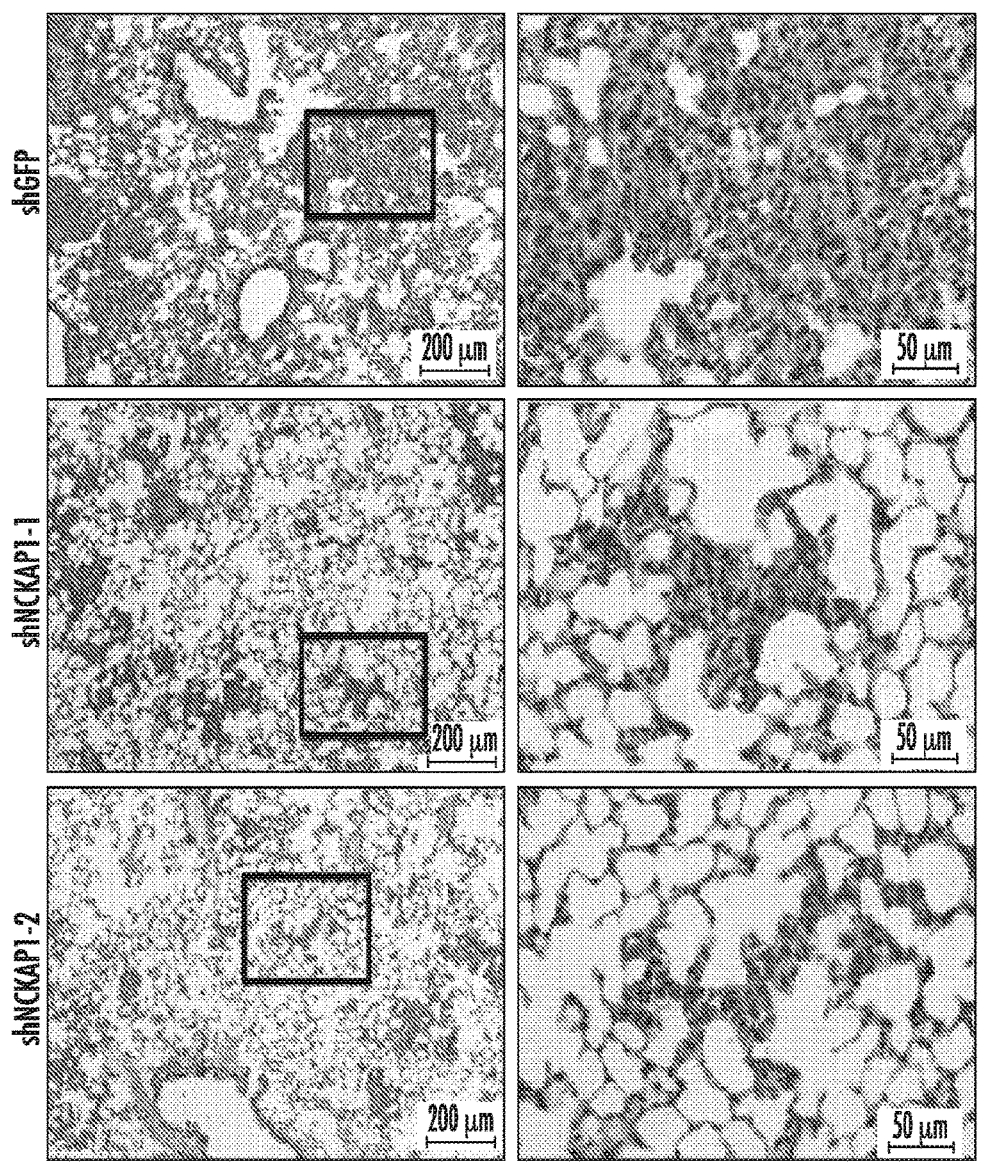

The suppression of invasion seen in vitro following knockdown of WASF3 has been correlated with suppression of metastasis in vivo in both zebrafish (Teng Y, et al. BMC Cancer. 2013 13:453) and mouse models (Sossey-Alaoui K, et al. Am J Pathol 2007 170:2112-2121; Teng Y, et al. Br J Cancer 2010 103:1066-1075). This NSG mouse model has been used for in vivo metastasis studies where, unlike SCID mouse models, primary tumor formation and metastasis occurs coincidentally within 2 months. To investigate the role of NCKAP1 in metastasis in vivo, MDA-MB-231 cells in which NCKAP1 had been knocked down were injected into the mammary fat pads of NSG mice and tumor development and metastasis followed over 8 weeks. There was no significant difference in primary tumor size (FIG. 14B) between the mice injected with either the NCKAP1 knockdown or knockdown control cells. When pulmonary metastasis was examined at the conclusion of the experiment, mice injected with the control cells showed multiple surface tumors. In contrast, those animals injected with MDA-MB-231 NCKAP1 knockdown cells showed a significantly reduced number of metastases (FIG. 14C). Histological analysis of the tumors from various animals further demonstrated that, while the mice injected with the control cells show multiple large tumors throughout the lungs, there are relatively few, small metastases in the mice injected with the NCKAP1 knockdown cells (FIG. 14D). Thus, loss of NCKAP1 expression inhibits in vivo metastasis, confirming that disrupting its interaction with the WASF3 complex may be a means of suppressing this aggressive stage of cancer.

Figure 15A:
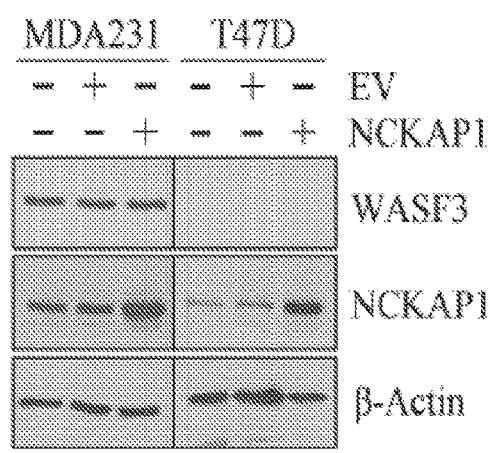
Figure 15B:
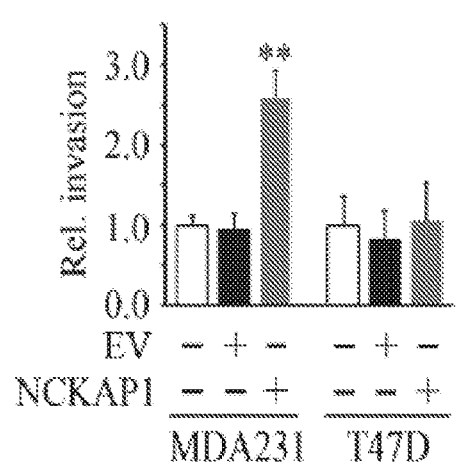
Figure 15C:
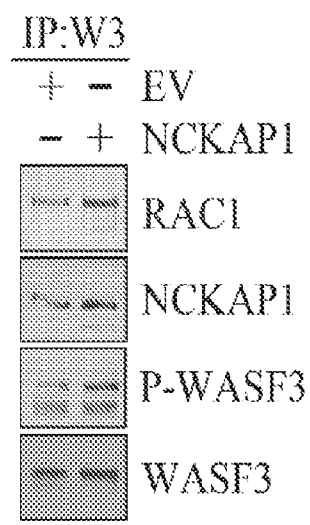
Figure 15D:
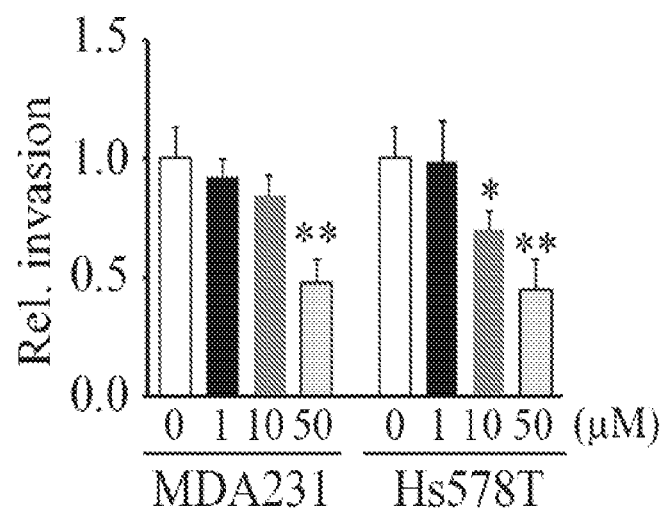
Figure 15E:
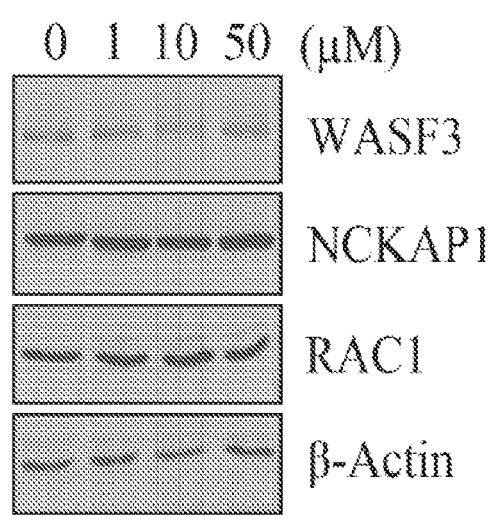
Figure 15F:
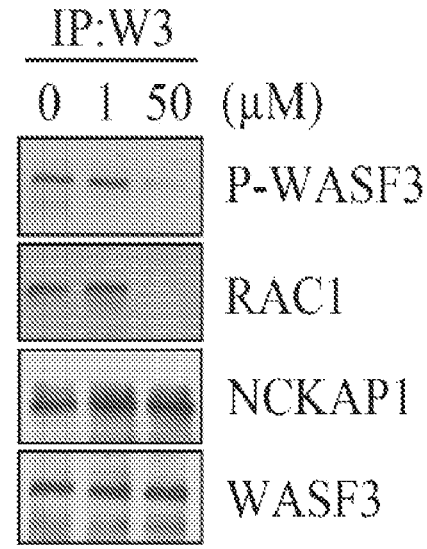
Figure 15G:
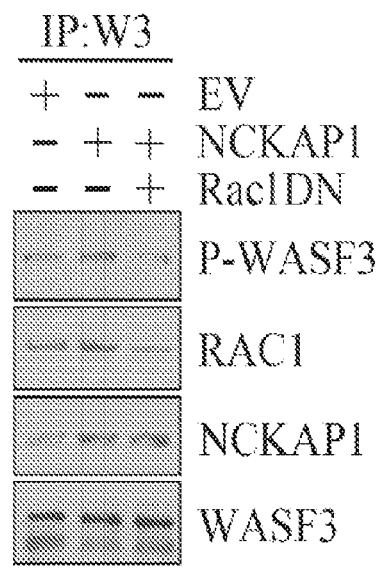
Figure 15H:
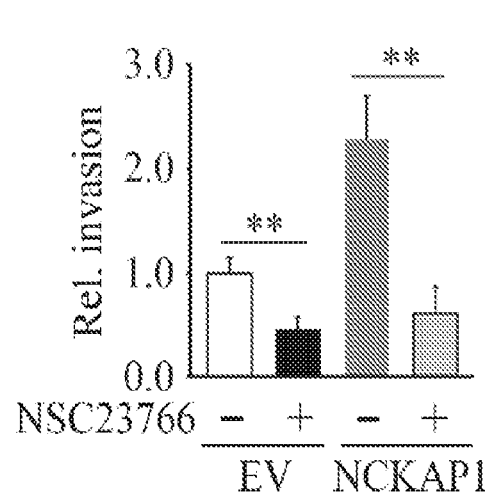
Figure 15I:
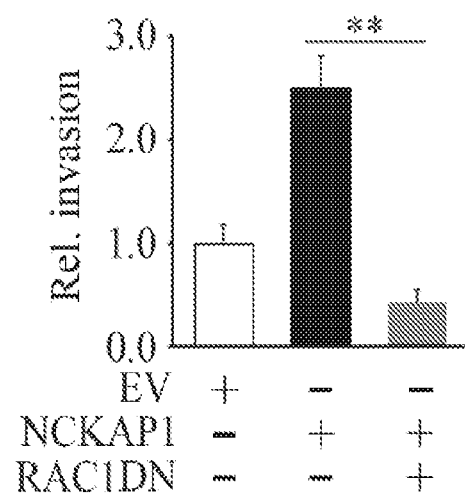

RAC1 Binding to the WASF3 Complex is Required for the NCKAP1-WASF3 Invasive Signaling Axis in Breast Cancer Cells Knockdown of NCKAP1 does not affect WASF3 transcription levels, but leads to a destabilization of the WASF3 protein. To further investigate whether NCKAP1 is functionally associated with WASF3, NCKAP1 was overexpressed in invasive MDA-MB-231 and non-invasive T47D cells, and cell invasion potential was analyzed. Overexpression of NCKAP1 did not increase WASF3 protein levels in either cell line (FIG. 15A) but significantly increased the invasion potential in MDA-MB-231 cells while making no difference in T47D cells which do not express WASF3 (FIG. 15B). Thus, WASF3 function is essential for NCKAP1-mediated invasion in breast cancer cells. IP of WASF3 from MDA-MB-231 cells demonstrated increased levels of NCKAP1 and RAC1 in the WASF3 immunocomplex, concomitant with increased WASF3 activation levels (FIG. 15C). These observations suggest that overexpressing NCKAP1 leads to increased engagement of RAC1 with the WASF3 complex. Treating MDA-MB-231 and Hs578T cells with NSC23766, which inhibits RAC1 function (Gao Y, et al. Proc Natl Acad Sci USA 2004 101:7618-7623), led to a dose-dependent reduction in invasion in both cell lines (FIG. 15D), without affecting cell proliferation (FIG. 21) or affecting the protein levels of either WASF3, NCKAP1 or RAC1 (FIG. 15E). IP analysis shows that NSC23766 does not disrupt engagement of NCKAP1 with the WASF3 complex, although high dose NSC23766 (50 µM) significantly inhibited WASF3 phosphorylation and RAC1 binding to the WASF3 complex (FIG. 15F), which is likely due to the reduced levels of active RAC1 in the cells. To further determine the role of RAC1 in the signaling axis dependent on the NCKAP1-WASF3 complex, a T17N dominant-negative RAC1 construct (RAC1DN) was transfected into MDAMB-231 cells overexpressing NCKAP1. Similar to NSC23677 treatment, expression of RAC1DN disrupted the WASF3 binding affinity with RAC1 and subsequently impaired WASF3 phosphoactivation (FIG. 15G). Moreover, both NSC23677 treatment (FIG. 15H) and overexpression of RAC1DN (FIG. 15I) led to a significant reduction of invasion potential in cells expressing NCKAP1, suggesting that inhibition of RAC1 activation attenuates NCKAP1-mediated cell invasion. Taken together, these data demonstrate that RAC1 binding to the WASF3 complex is critical for promoting invasion in breast cancer cells.

Figure 16A:
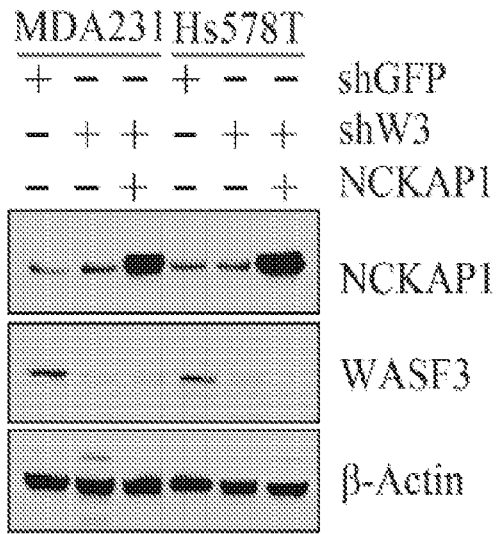
Figure 16B:
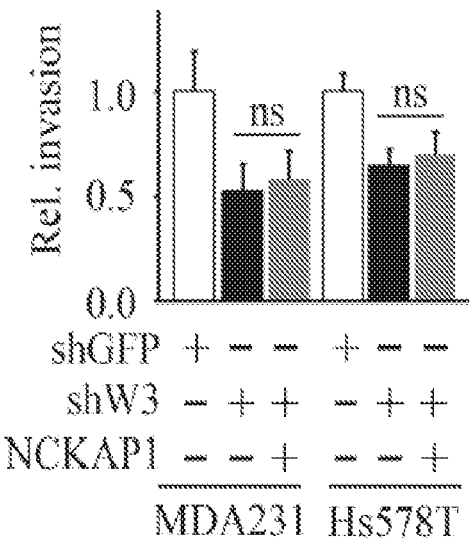
Figure 16C:
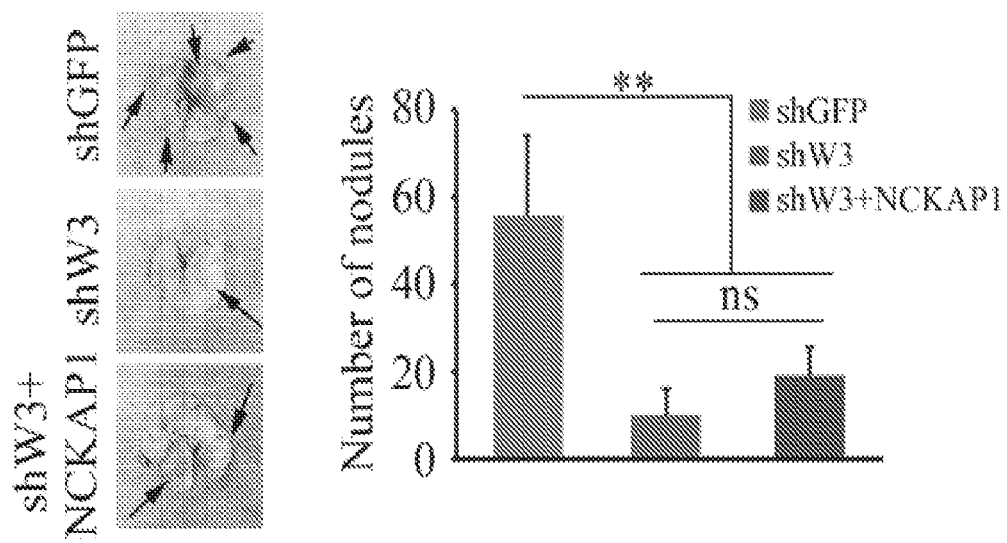

NCKAP1 Engagement with the WASF3 Complex is Required for Metastasis of Breast Cancer Cells Knockdown of WASF3 in MDA-MB-231 and Hs578T cells (FIG. 16A) led to a significant reduction in invasion potential (FIG. 16B) (Sossey-Alaoui K, et al. J Biol Chem 2005 280:21748-21755; Sossey-Alaoui K, et al. J Biol Chem 2007 282:26257-26265; Teng Y, et al. Int J Cancer 2011 129:2825-2835; Teng Y, et al. J Biol Chem 2012 287:10051-10059; Teng Y, et al. Carcinogenesis 2013 34:1994-1999; Sossey-Alaoui K, et al. Am J Pathol 2007 170:2112-2121; Teng Y, et al. Br J Cancer 2010 103:1066-1075; Teng Y, et al. BMC Cancer. 2013 13:453; 25-27). There was, however, no significant increase in invasion potential (FIG. 16B) as a result of overexpression of NCKAP1 in WASF3 knockdown cells (FIG. 16A), compared with the parental cells. When in vivo metastasis assays were performed using NSG mice, increased numbers of tumor nodules were seen on the surface of the lungs in the knockdown control cells compared with either the WASF3 knockdown cells or the WASF3 knockdown cells overexpressing NCKAP1 (FIG. 16C). In addition, there is no significant change in the number of tumor nodules on the surface of the lungs when NCKAP1 was overexpressed in WASF3 knockdown cells (FIG. 16C). Histological examination of the lungs of these mice shows large tumor foci in the knockdown control cells compared with the small tumor foci from the WASF3 knockdown cells (FIG. 16D). Thus, consistent with the in vitro invasion assays, metastasis potential to the lung was not increased in the WASF3 knockdown MDAMB-231 cells expressing NCKAP1, compared with the WASF3 knockdown cells (FIG. 16D). Collectively, these data demonstrate that the NCKAP1-WASF3 complex is essential for cell invasion and metastasis in breast cancer cells.

Suppression of Invasion by Targeting the CYFIP1-NCKAP1 Interaction Using SPs

Figure 17C:
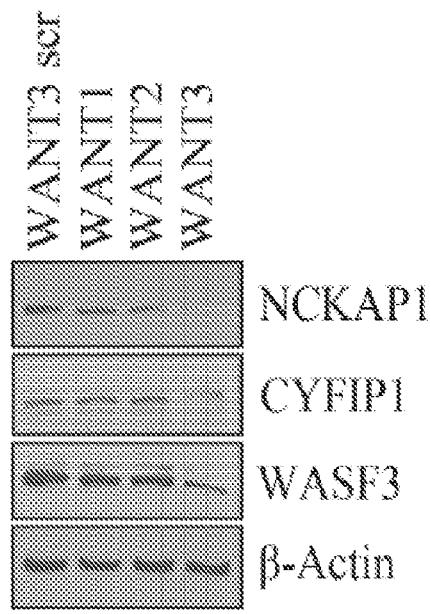
Figure 17D:
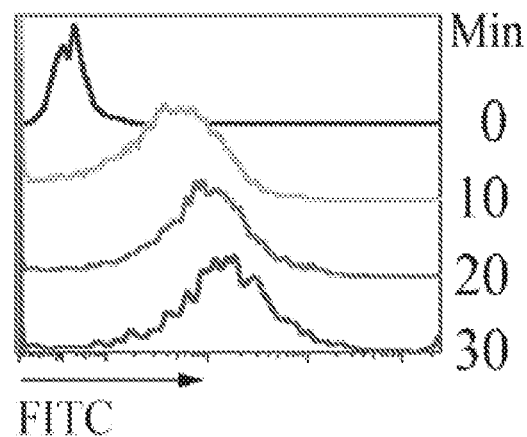
Figure 17E:
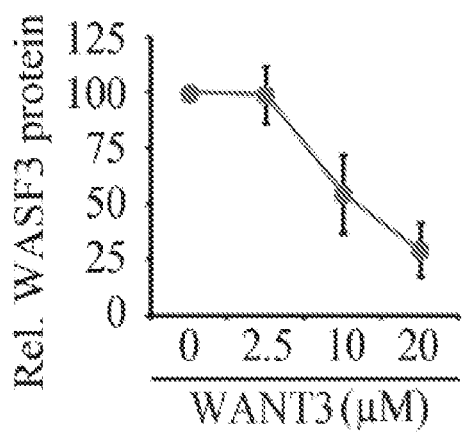

The genetic knockdown of NCKAP1 in highly invasive cancer cells leads to suppression of invasion (FIG. 13B), which is accompanied by destabilization of WASF3. The same destabilization of WASF3 was seen following knockdown of CYFIP1, which associates with WASF3 as a dimer with NCKAP1. This loss of either member of this trimeric complex leads to loss of WASF3 protein levels (FIG. 22) and suppresses invasion. These observations suggest that disrupting the engagement of NCKAP1 with the WASF3 complex could also lead disruption of the WRC and lead to loss of invasion. There are currently no small molecules that target WASF3 function directly, but targeting the WRC may provide a means of suppressing invasion. Targeting a direct protein-protein interaction between CYFIP1 and WASF3 using SPs can effectively suppress invasion in WASF3 overexpressing cancer cells and suppress activation of WASF3. It is possible, therefore that disrupting the WRC by targeting NCKAP1 might have the same consequence. Analysis of the crystal structure of the WRC complex, however, showed no direct contact between NCKAP1 and WASF3 (Chen B, et al. Cell 2014 156:195-207), even though loss of NCKAP1 leads to reduced WASF3 stability (FIG. 13A). SPs target α-helical surfaces between proteins, and several interacting α-helical surfaces between CYFIP1 and NCKAP1 (FIG. 23) were identified. To determine whether SPs targeting the NCKAP1-CYFIP1 interaction could also lead to suppression of invasion, three regions within NCKAP1 were identified that showed α-helical interactions with CYFIP1. These PPIs encompassed amino acids 631-642, 933-944 and 1110-1121 and stapled peptides, designated WASF3-NCKAP1 Targets (WANT), were designed against the NCKAP1 surface (FIG. 17A) at these three positions. Highly invasive MDA-MB-231 and HS578T breast cancer cells were treated independently with each of the three WANT peptides at a final concentration of 10 µM. When MDA-MB-231 cells were then challenged to invade in Transwell chamber assays, no significant effect on invasion potential was observed in the presence of WANT1 and WANT2 (FIG. 17B), albeit with only a single peptide designed against these regions. In contrast, treatment with WANT3 resulted in a highly significant suppression of invasion (FIG. 17B) without affecting cell proliferation (FIG. 24A). To investigate the mechanism of WANT3 action, WASF3 stability was analyzed using western blotting, compared with treatment with a scrambled peptide, which showed that WANT3 specifically resulted in a significant destabilization of WASF3 (FIG. 17C), coincident with loss of the NCKAP1 protein. Flow cytometry analysis demonstrated that, in the two different breast cancer cell lines, uptake of these peptides was rapid, achieving maximal levels after only 10-20 minutes (FIG. 17D). Significantly, in vitro cell toxicity at 10 µM, was minimal (FIG. 24) and the ability of WANT3 to suppress WASF3 stability was dose dependent (FIG. 25 and FIG. 17E), achieving a maximal effect at 20 µM. The observation that targeting the WRC with stapled peptides can lead to suppression of invasion provides preclinical evidence that this target may be a means of suppressing invasion and potentially metastasis.

Figure 17F:
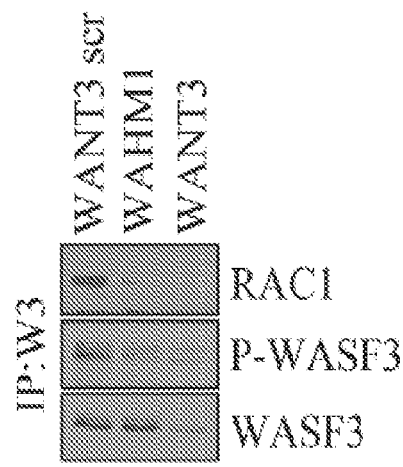
Figure 17G:
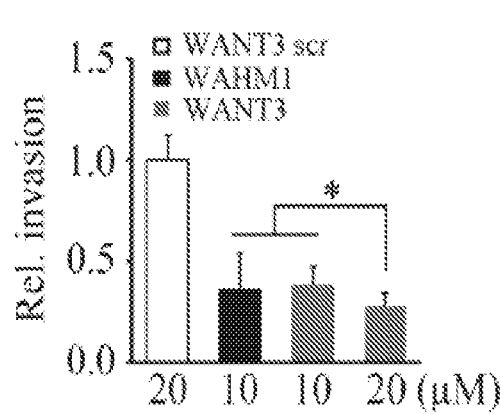
Figure 17H:
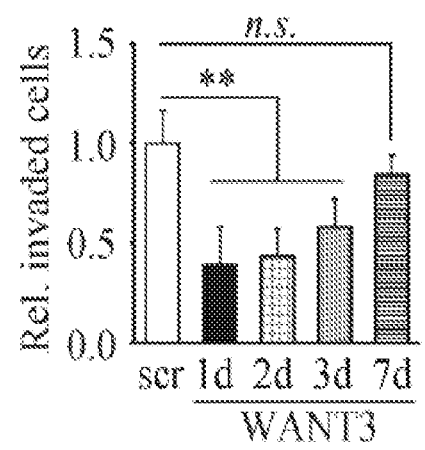

Since targeting the WASF3-CYFIP1 PPI also led to disruption of the WRC and suppression of invasion, the relative ability of targeting the WASF3-CYFIP1 (using the WHAM1 peptide) or NCKAP1-CYFIP1 (using the WANT3 peptide) interaction to disrupt the WRC was investigated. Following treatment of MDAMB-231cells with WHAM1 or WANT3 it was clear that targeting the CYFIP1-NCKAP1 interaction was more efficient in destabilizing WASF3 than targeting the WASF3-CYFIP1 interaction (FIG. 17G). WASF3 is activated through its interaction with RAC1 binding to CYFIP1 (Chen Z, et al. Nature 2010 468:533-538) and so the engagement of RAC1 in the absence of NCKAP1 is suppressed since targeting the CYFIP1-NCKAP1 interaction leads to destabilization of the WRC. The engagement of RAC1 with the WASF3 complex was more significant following treatment with WANT3 than WHAM1 (FIG. 17F). Despite this variance in the level of destabilization of the WRC, Transwell assays demonstrated that both WAHM1 and WANT3 peptides produced comparable suppression of invasion (FIG. 17H). Increasing the concentration of WANT3 led to a greater suppression of invasion (FIG. 17H).

The observation that targeting the WRC with SPs can lead to suppression of invasion provides preclinical evidence that this approach may provide a means of suppressing invasion and potentially metastasis. To evaluate the stability of these SPs, WANT3 was incubated in serum containing medium for varying lengths of time (1-7 days) at 37° C. and then this medium was added to MDA-MB-231 cells to evaluate the ability of the preincubated peptides to suppress invasion. As shown in FIG. 17I, WANT3 peptides that had been preincubated for up to three days were still able to significantly suppress invasion. Even after 7 days, although not significant, there was a residual effect on suppression of invasion.

Discussion

Reorganization of the actin cytoskeleton to facilitate cell invasion and metastasis is a complex regulatory process involving many interacting pathways (Insall R H, et al. Dev Cell 2009 17:310-322; Yilmaz M, et al. Cancer Metastasis Rev 2009 28:15-33; Krause M, et al. Nat Rev Mol Cell Biol 2014 15:577-590). One of the key initiating events is the activation of RAC1, which is known to signal actin cytoskeleton reorganization following stimulation with growth factor receptors (Lebensohn A M, et al. Mol Cell 2009 36:512-524; Akin O, et al. Cell. 2014; 156(1-2):13-14), which facilitates recruitment of WASF family members to the membrane to promote invasion. As disclosed herein, RAC1 cannot be recruited to the WASF3 complex in the absence of NCKAP1. High level expression of NCKAP1 is associated with poorer survival in breast cancer patients, which may be due to the increased stability of WASF3 since, when NCKAP1 levels are increased in MDA-MB-231 cells, invasion potential also increases, which is associated with increased RAC1 binding to the complex and increased activation of WASF3. This cascade leading to increased invasion, however, is dependent on WASF3 expression since non-invasive cells do not respond to increased NCKAP1 expression.

WASF3 is one of a three member family which share similar structural motifs that define their function in actin cytoskeletal reorganization (Sossey-Alaoui K, et al. Mamm Genome 2003 14:314-322). Knockdown of WASF3 leads to suppression of invasion and metastasis in breast and prostate cancer cells, despite sustained expression of WASF1 and WASF2, which clearly cannot compensate for the suppression of invasion. Knockdown of WASF1 and WASF2 in these same breast cancer cells does not lead to suppression of invasion or metastasis. While WASF3 regulates lamellipodia formation (Sossey-Alaoui K, et al. J Biol Chem 2005

280:21748-21755), which is essential for the development of the invasion and metastasis phenotypes, WASF1 appears to regulate dorsal ruffle formation while WASF2 regulates filopodia production (Suetsugu S, et al. Dev Cell 2003 5:595-609). It is possible, therefore, that while controlling similar actin dynamics, the specificity of WASF3 in influencing metastasis depends on the mechanisms of its regulation and possibly the proteins it binds to. WASF3, for example is under the regulation of the STAT3 transcription factor (Teng Y, et al. Carcinogenesis 2013 34:1994-1999; Teng Y, et al. JAKSTAT 2014 3:e28086) and is activated following cytokine and growth factor stimulation, but WASF1 and WASF2 do not have consensus STAT binding sites in their promoters and do not respond to IL6 stimulation (Teng Y, et al. Carcinogenesis 2013 34:1994-1999). Knockdown of NCKAP1, however, also leads to destabilization of WASF1 and WASF2 protein complexes but no specific resultant cell phenotypes were evident.

Part of the mechanism proposed for WASF protein function is through recruitment to membrane locations following growth factor stimulation resulting from actin cytoskeleton reorganization through interactions with NCK1 (Dart A E, et al. J Cell Sci 2012 125:2825-2830; Pils S, et al. PLoS One 2012 7:e32808). Consistent with this idea, NCK1 is not present in the WASF3 immunocomplex in the absence of serum, and WASF3 is not activated, but addition of serum growth factors activates WASF3 and a sub pool of protein interacts with NCK1. In contrast, NCKAP1 is associated with WASF3 in both its inactive and active forms consistent with the idea that its presence is required for protein stability. NCK1 may therefore be an important protein for the recruitment of the WASF3 complex to tyrosine kinase receptor complexes through an interaction with NCKAP1 upon extracellular stimulation. Thus, NCK1-NCKAP1-RAC1 signaling may be critical for WASF3 activation leading to the significant consequence of cell invasion.

The central role of WASF3 in regulating invasion and metastasis (Sossey-Alaoui K, et al. J Biol Chem 2005 280:21748-21755; Sossey-Alaoui K, et al. J Biol Chem 2007 282:26257-26265; Teng Y, et al. Int J Cancer 2011 129: 2825-2835; Teng Y, et al. J Biol Chem 2012 287:10051-10059; Teng Y, et al. Carcinogenesis 2013 34:1994-1999; Sossey-Alaoui K, et al. Am J Pathol 2007 170:2112-2121; Teng Y, et al. Br J Cancer 2010 103:1066-1075; Teng Y, et al. BMC Cancer. 2013 13:453; Teng Y, et al. JAKSTAT 2014 3:e28086; Teng Y, et al. Oncogene 2014 33:203-211; Ghoshal P, et al. Int J Cancer 2012 131:E905-E915), together with its overexpression in high-grade and metastatic tumors (Prat A, et al. Breast Cancer Res 2010 12:R68; Kulkarni S, et al. PLoS One 2012 7:e42895), provides an ideal target to suppress metastasis. As disclosed herein, stapled peptides targeting the large interaction interface between two key proteins that maintain the integrity of WASF3, leads to destabilization of WASF3 and suppression of invasion, suggesting this complex as a target to suppress metastasis. Since there are currently no small molecules that target WASF3, and the interface lacks pockets required for small molecule targeting, the development of the WANT3 peptide described here, and the WHAM peptides targeting the WASF3-CYFIP1 interaction provide a potential approach to suppress WASF3 function as an approach to suppress metastasis. The emerging field of stapled peptides as therapeutic agents is gaining traction through clinical trials currently underway targeting the MDM2/MDMX-p53 protein interaction (Chang Y S, et al. Proc Natl Acad Sci USA 2013 110:E3445-E3454; Qian C, et al. Med Chem Commun 2015 6:111-119) for cancer patients with tumors expressing wild type p53. Although there are many peptides currently in clinical trials, because of their limited ability to penetrate the cell, most target extracellular proteins. Stapled peptides on the other hand, are constrained in a highly stable helical conformation, and address many of the limitations of standard peptides because of (Hanahan D, et al. Cell 2011 144:646-674) their active transport into cells (Steeg P S. Nat Med 2003 9:822-823) their pharmaceutical stability (Nguyen D X, et al. Nat Rev Genet 2007 8:341-352) low immunogenicity and (Hurst D R, et al. Int Rev Cell Mol Biol 2011 286:107-180) their binding affinity for the target (Verdine G L, et al. Methods Enzymol 2012 503:3-33). Indeed, the NCKAP1 peptide mimic, WANT3, retains its ability to suppress invasion after incubation in serum for up to three days. Since phosphoactivation is required for the ability of WASF3 to regulate invasion, both peptide mimics suppress invasion equally effectively. This approach validates the WASF3 complex as a viable target for suppression of metastasis.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A synthetic polypeptide, comprising an amino acid sequence that comprises SEQ ID NO: 1 or SEQ ID NO: 2.

* * * * *

SEQUENCE LISTING

```
<160> NUMBER OF SEQ ID NOS: 17

<210> SEQ ID NO 1
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (4)..(4)
<223> OTHER INFORMATION: (S)-2-(4'-pentenyl)alanine
<220> FEATURE:
<221> NAME/KEY: SITE
<222> LOCATION: (8)..(8)
<223> OTHER INFORMATION: (S)-2-(4'-pentenyl)alanine
```

-continued

```
<400> SEQUENCE: 1

Leu Glu Lys Xaa Thr Asn Ser Xaa Leu Ala Lys Ile Ile Arg Gln Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (7)..(7)
<223> OTHER INFORMATION: (S)-2-(4'-pentenyl)alanine
<220> FEATURE:
<221> NAME/KEY: SITE
<222> LOCATION: (11)..(11)
<223> OTHER INFORMATION: (S)-2-(4'-pentenyl)alanine

<400> SEQUENCE: 2

Leu Glu Lys Lys Thr Asn Xaa Thr Leu Ala Xaa Ile Ile Arg Gln Leu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (4)..(4)
<223> OTHER INFORMATION: (S)-2-(4'-pentenyl)alanine
<220> FEATURE:
<221> NAME/KEY: SITE
<222> LOCATION: (8)..(8)
<223> OTHER INFORMATION: (S)-2-(4'-pentenyl)alanine

<400> SEQUENCE: 3

Ser Arg Ala Xaa Leu Leu Ile Xaa Thr Lys Ile Gln Asn Glu Leu Lys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (7)..(7)
<223> OTHER INFORMATION: (S)-2-(4'-pentenyl)alanine
<220> FEATURE:
<221> NAME/KEY: SITE
<222> LOCATION: (11)..(11)
<223> OTHER INFORMATION: (S)-2-(4'-pentenyl)alanine

<400> SEQUENCE: 4

Thr Arg Ala Ile Leu Leu Xaa Ile Thr Lys Xaa Gln Asn Glu Leu Lys
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (5)..(5)
```

```
<223> OTHER INFORMATION: (S)-2-(4'-pentenyl)alanine
<220> FEATURE:
<221> NAME/KEY: SITE
<222> LOCATION: (9)..(9)
<223> OTHER INFORMATION: (S)-2-(4'-pentenyl)alanine

<400> SEQUENCE: 5

Lys His Cys Ala Xaa Thr Ile Ser Xaa Ala Val Asn Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (3)..(3)
<223> OTHER INFORMATION: (S)-2-(4'-pentenyl)alanine
<220> FEATURE:
<221> NAME/KEY: SITE
<222> LOCATION: (7)..(7)
<223> OTHER INFORMATION: (S)-2-(4'-pentenyl)alanine

<400> SEQUENCE: 6

Glu Leu Xaa Ser Ser Ile Xaa Asp Phe Lys Asp His Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (3)..(3)
<223> OTHER INFORMATION: (S)-2-(4'-pentenyl)alanine
<220> FEATURE:
<221> NAME/KEY: SITE
<222> LOCATION: (7)..(7)
<223> OTHER INFORMATION: (S)-2-(4'-pentenyl)alanine

<400> SEQUENCE: 7

Val Leu Xaa Arg Asn Ala Xaa His Ala Val Tyr Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: (3)..(3)
<223> OTHER INFORMATION: (S)-2-(4'-pentenyl)alanine
<220> FEATURE:
<221> NAME/KEY: SITE
<222> LOCATION: (7)..(7)
<223> OTHER INFORMATION: (S)-2-(4'-pentenyl)alanine

<400> SEQUENCE: 8

His Lys Xaa Val Tyr Leu Xaa Ala Asn Arg Ala Val
1               5                   10

<210> SEQ ID NO 9
<211> LENGTH: 13
<212> TYPE: PRT
<213> ORGANISM: Artificial Sequence
```

```
<220> FEATURE:
<223> OTHER INFORMATION: synthetic construct

<400> SEQUENCE: 9

Lys His Cys Ala Lys Thr Ile Ser Gln Ala Val Asn Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic construct

<400> SEQUENCE: 10

Pro Phe Leu Val Ser Ser Ile Glu Asp Phe Lys Asp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic construct

<400> SEQUENCE: 11

Val Leu Leu Arg Asn Ala Tyr His Ala Val Tyr Lys
1               5                   10

<210> SEQ ID NO 12
<211> LENGTH: 16
<212> TYPE: PRT
<213> ORGANISM: Homo sapiens

<400> SEQUENCE: 12

Leu Glu Cys Val Thr Asn Ile Ser Leu Ala Asn Ile Ile Arg Gln Leu
1               5                   10                  15

<210> SEQ ID NO 13
<211> LENGTH: 16
<212> TYPE: PRT
<213> ORGANISM: Homo sapiens

<400> SEQUENCE: 13

Leu Glu Cys Val Thr Asn Ile Thr Leu Ala Asn Val Ile Arg Gln Leu
1               5                   10                  15

<210> SEQ ID NO 14
<211> LENGTH: 16
<212> TYPE: PRT
<213> ORGANISM: Homo sapiens

<400> SEQUENCE: 14

Leu Glu Cys Val Thr Asn Ser Thr Leu Ala Ala Ile Ile Arg Gln Leu
1               5                   10                  15

<210> SEQ ID NO 15
<211> LENGTH: 502
<212> TYPE: PRT
<213> ORGANISM: Homo sapiens

<400> SEQUENCE: 15

Met Pro Leu Val Lys Arg Asn Ile Glu Pro Arg His Leu Cys Arg Gly
1               5                   10                  15

Ala Leu Pro Glu Gly Ile Thr Ser Glu Leu Glu Cys Val Thr Asn Ser
```

```
              20                  25                  30
Thr Leu Ala Ala Ile Ile Arg Gln Leu Ser Ser Leu Ser Lys His Ala
            35                  40                  45
Glu Asp Ile Phe Gly Glu Leu Phe Asn Glu Ala Asn Asn Phe Tyr Ile
        50                  55                  60
Arg Ala Asn Ser Leu Gln Asp Arg Ile Asp Arg Leu Ala Val Lys Val
65                  70                  75                  80
Thr Gln Leu Asp Ser Thr Val Glu Val Ser Leu Gln Asp Ile Asn
                85                  90                  95
Met Lys Lys Ala Phe Lys Ser Ser Thr Val Gln Asp Gln Gln Val Val
            100                 105                 110
Ser Lys Asn Ser Ile Pro Asn Pro Val Ala Asp Ile Tyr Asn Gln Ser
        115                 120                 125
Asp Lys Pro Pro Leu Asn Ile Leu Thr Pro Tyr Arg Asp Asp Lys
130                 135                 140
Lys Asp Gly Leu Lys Phe Tyr Thr Asp Pro Ser Tyr Phe Phe Asp Leu
145                 150                 155                 160
Trp Lys Glu Lys Met Leu Gln Asp Thr Glu Asp Lys Arg Lys Glu Lys
                165                 170                 175
Arg Arg Gln Lys Glu Gln Lys Arg Ile Asp Gly Thr Thr Arg Glu Val
            180                 185                 190
Lys Lys Val Arg Lys Ala Arg Asn Arg Arg Gln Glu Trp Asn Met Met
        195                 200                 205
Ala Tyr Asp Lys Glu Leu Arg Pro Asp Asn Arg Leu Ser Gln Ser Val
210                 215                 220
Tyr His Gly Ala Ser Ser Glu Gly Ser Leu Ser Pro Asp Thr Arg Ser
225                 230                 235                 240
His Ala Ser Asp Val Thr Asp Tyr Ser Tyr Pro Ala Thr Pro Asn His
                245                 250                 255
Ser Leu His Pro Gln Pro Val Thr Pro Ser Tyr Ala Ala Gly Asp Val
            260                 265                 270
Pro Pro His Gly Pro Ala Ser Gln Ala Ala Glu His Glu Tyr Arg Pro
        275                 280                 285
Pro Ser Ala Ser Ala Arg His Met Ala Leu Asn Arg Pro Gln Gln Pro
        290                 295                 300
Pro Pro Pro Pro Pro Gln Ala Pro Glu Gly Ser Gln Ala Ser Ala
305                 310                 315                 320
Pro Met Ala Pro Ala Asp Tyr Gly Met Leu Pro Ala Gln Ile Ile Glu
                325                 330                 335
Tyr Tyr Asn Pro Ser Gly Pro Pro Pro Pro Pro Pro Val Ile
            340                 345                 350
Pro Ser Ala Gln Thr Ala Phe Val Ser Pro Leu Gln Met Pro Met Gln
        355                 360                 365
Pro Pro Phe Pro Ala Ser Ala Ser Ser Thr His Ala Ala Pro Pro His
        370                 375                 380
Pro Pro Ser Thr Gly Leu Leu Val Thr Ala Pro Pro Pro Gly Pro
385                 390                 395                 400
Pro Pro Pro Pro Gly Pro Pro Gly Pro Gly Ser Ser Leu Ser Ser
                405                 410                 415
Ser Pro Met His Gly Pro Pro Val Ala Glu Ala Lys Arg Gln Glu Pro
            420                 425                 430
Ala Gln Pro Pro Ile Ser Asp Ala Arg Ser Asp Leu Leu Ala Ala Ile
        435                 440                 445
```

Arg Met Gly Ile Gln Leu Lys Lys Val Gln Glu Gln Arg Glu Gln Glu
        450                 455                 460

Ala Lys Arg Glu Pro Val Gly Asn Asp Val Ala Thr Ile Leu Ser Arg
465                 470                 475                 480

Arg Ile Ala Val Glu Tyr Ser Asp Ser Asp Asp Ser Glu Phe Asp
                    485                 490                 495

Glu Asn Asp Trp Ser Asp
                500

<210> SEQ ID NO 16
<211> LENGTH: 1253
<212> TYPE: PRT
<213> ORGANISM: Homo sapiens

<400> SEQUENCE: 16

Met Ala Ala Gln Val Thr Leu Glu Asp Ala Leu Ser Asn Val Asp Leu
1                   5                   10                  15

Leu Glu Glu Leu Pro Leu Pro Asp Gln Gln Pro Cys Ile Glu Pro Pro
                20                  25                  30

Pro Ser Ser Leu Leu Tyr Gln Pro Asn Phe Asn Thr Asn Phe Glu Asp
            35                  40                  45

Arg Asn Ala Phe Val Thr Gly Ile Ala Arg Tyr Ile Glu Gln Ala Thr
        50                  55                  60

Val His Ser Ser Met Asn Glu Met Leu Glu Glu Gly Gln Glu Tyr Ala
65                  70                  75                  80

Val Met Leu Tyr Thr Trp Arg Ser Cys Ser Arg Ala Ile Pro Gln Val
                85                  90                  95

Lys Cys Asn Glu Gln Pro Asn Arg Val Glu Ile Tyr Glu Lys Thr Val
                100                 105                 110

Glu Val Leu Glu Pro Glu Val Thr Lys Leu Met Asn Phe Met Tyr Phe
            115                 120                 125

Gln Arg Asn Ala Ile Glu Arg Phe Cys Gly Glu Val Arg Arg Leu Cys
        130                 135                 140

His Ala Glu Arg Arg Lys Asp Phe Val Ser Glu Ala Tyr Leu Ile Thr
145                 150                 155                 160

Leu Gly Lys Phe Ile Asn Met Phe Ala Val Leu Asp Glu Leu Lys Asn
                165                 170                 175

Met Lys Cys Ser Val Lys Asn Asp His Ser Ala Tyr Lys Arg Ala Ala
                180                 185                 190

Gln Phe Leu Arg Lys Met Ala Asp Pro Gln Ser Ile Gln Glu Ser Gln
        195                 200                 205

Asn Leu Ser Met Phe Leu Ala Asn His Asn Lys Ile Thr Gln Ser Leu
    210                 215                 220

Gln Gln Gln Leu Glu Val Ile Ser Gly Tyr Glu Glu Leu Leu Ala Asp
225                 230                 235                 240

Ile Val Asn Leu Cys Val Asp Tyr Tyr Glu Asn Arg Met Tyr Leu Thr
                245                 250                 255

Pro Ser Glu Lys His Met Leu Leu Lys Val Met Gly Phe Gly Leu Tyr
                260                 265                 270

Leu Met Asp Gly Ser Val Ser Asn Ile Tyr Lys Leu Asp Ala Lys Lys
            275                 280                 285

Arg Ile Asn Leu Ser Lys Ile Asp Lys Tyr Phe Lys Gln Leu Gln Val
        290                 295                 300

Val Pro Leu Phe Gly Asp Met Gln Ile Glu Leu Ala Arg Tyr Ile Lys

-continued

```
            305                 310                 315                 320
        Thr Ser Ala His Tyr Glu Glu Asn Lys Ser Arg Trp Thr Cys Thr Ser
                        325                 330                 335
        Ser Gly Ser Ser Pro Gln Tyr Asn Ile Cys Glu Gln Met Ile Gln Ile
                        340                 345                 350
        Arg Glu Asp His Met Arg Phe Ile Ser Glu Leu Ala Arg Tyr Ser Asn
                        355                 360                 365
        Ser Glu Val Val Thr Gly Ser Gly Arg Gln Glu Ala Gln Lys Thr Asp
                        370                 375                 380
        Ala Glu Tyr Arg Lys Leu Phe Asp Leu Ala Leu Gln Gly Leu Gln Leu
        385                 390                 395                 400
        Leu Ser Gln Trp Ser Ala His Val Met Glu Val Tyr Ser Trp Lys Leu
                        405                 410                 415
        Val His Pro Thr Asp Lys Tyr Ser Asn Lys Asp Cys Pro Asp Ser Ala
                        420                 425                 430
        Glu Glu Tyr Glu Arg Ala Thr Arg Tyr Asn Tyr Thr Ser Glu Glu Lys
                        435                 440                 445
        Phe Ala Leu Val Glu Val Ile Ala Met Ile Lys Gly Leu Gln Val Leu
                        450                 455                 460
        Met Gly Arg Met Glu Ser Val Phe Asn His Ala Ile Arg His Thr Val
        465                 470                 475                 480
        Tyr Ala Ala Leu Gln Asp Phe Ser Gln Val Thr Leu Arg Glu Pro Leu
                        485                 490                 495
        Arg Gln Ala Ile Lys Lys Lys Asn Val Ile Gln Ser Val Leu Gln
                        500                 505                 510
        Ala Ile Arg Lys Thr Val Cys Asp Trp Glu Thr Gly His Glu Pro Phe
                        515                 520                 525
        Asn Asp Pro Ala Leu Arg Gly Glu Lys Asp Pro Lys Ser Gly Phe Asp
                        530                 535                 540
        Ile Lys Val Pro Arg Arg Ala Val Gly Pro Ser Ser Thr Gln Leu Tyr
        545                 550                 555                 560
        Met Val Arg Thr Met Leu Glu Ser Leu Ile Ala Asp Lys Ser Gly Ser
                        565                 570                 575
        Lys Lys Thr Leu Arg Ser Ser Leu Glu Gly Pro Thr Ile Leu Asp Ile
                        580                 585                 590
        Glu Lys Phe His Arg Glu Ser Phe Phe Tyr Thr His Leu Ile Asn Phe
                        595                 600                 605
        Ser Glu Thr Leu Gln Gln Cys Cys Asp Leu Ser Gln Leu Trp Phe Arg
                        610                 615                 620
        Glu Phe Phe Leu Glu Leu Thr Met Gly Arg Arg Ile Gln Phe Pro Ile
        625                 630                 635                 640
        Glu Met Ser Met Pro Trp Ile Leu Thr Asp His Ile Leu Glu Thr Lys
                        645                 650                 655
        Glu Ala Ser Met Met Glu Tyr Val Leu Tyr Ser Leu Asp Leu Tyr Asn
                        660                 665                 670
        Asp Ser Ala His Tyr Ala Leu Thr Arg Phe Asn Lys Gln Phe Leu Tyr
                        675                 680                 685
        Asp Glu Ile Glu Ala Glu Val Asn Leu Cys Phe Asp Gln Phe Val Tyr
                        690                 695                 700
        Lys Leu Ala Asp Gln Ile Phe Ala Tyr Tyr Lys Val Met Ala Gly Ser
        705                 710                 715                 720
        Leu Leu Leu Asp Lys Arg Leu Arg Ser Glu Cys Lys Asn Gln Gly Ala
                        725                 730                 735
```

```
Thr Ile His Leu Pro Pro Ser Asn Arg Tyr Glu Thr Leu Leu Lys Gln
        740                 745                 750

Arg His Val Gln Leu Leu Gly Arg Ser Ile Asp Leu Asn Arg Leu Ile
        755                 760                 765

Thr Gln Arg Val Ser Ala Ala Met Tyr Lys Ser Leu Glu Leu Ala Ile
        770                 775                 780

Gly Arg Phe Glu Ser Glu Asp Leu Thr Ser Ile Val Glu Leu Asp Gly
785                 790                 795                 800

Leu Leu Glu Ile Asn Arg Met Thr His Lys Leu Leu Ser Arg Tyr Leu
                805                 810                 815

Thr Leu Asp Gly Phe Asp Ala Met Phe Arg Glu Ala Asn His Asn Val
        820                 825                 830

Ser Ala Pro Tyr Gly Arg Ile Thr Leu His Val Phe Trp Glu Leu Asn
        835                 840                 845

Tyr Asp Phe Leu Pro Asn Tyr Cys Tyr Asn Gly Ser Thr Asn Arg Phe
850                 855                 860

Val Arg Thr Val Leu Pro Phe Ser Gln Glu Phe Gln Arg Asp Lys Gln
865                 870                 875                 880

Pro Asn Ala Gln Pro Gln Tyr Leu His Gly Ser Lys Ala Leu Asn Leu
                885                 890                 895

Ala Tyr Ser Ser Ile Tyr Gly Ser Tyr Arg Asn Phe Val Gly Pro Pro
                900                 905                 910

His Phe Gln Val Ile Cys Arg Leu Leu Gly Tyr Gln Gly Ile Ala Val
        915                 920                 925

Val Met Glu Glu Leu Leu Lys Val Val Lys Ser Leu Leu Gln Gly Thr
        930                 935                 940

Ile Leu Gln Tyr Val Lys Thr Leu Met Glu Val Met Pro Lys Ile Cys
945                 950                 955                 960

Arg Leu Pro Arg His Glu Tyr Gly Ser Pro Gly Ile Leu Glu Phe Phe
                965                 970                 975

His His Gln Leu Lys Asp Ile Val Glu Tyr Ala Glu Leu Lys Thr Val
        980                 985                 990

Cys Phe Gln Asn Leu Arg Glu Val Gly Asn Ala Ile Leu Phe Cys Leu
        995                 1000                1005

Leu Ile Glu Gln Ser Leu Ser Leu Glu Glu Val Cys Asp Leu Leu
        1010                1015                1020

His Ala Ala Pro Phe Gln Asn Ile Leu Pro Arg Val His Val Lys
        1025                1030                1035

Glu Gly Glu Arg Leu Asp Ala Lys Met Lys Arg Leu Glu Ser Lys
        1040                1045                1050

Tyr Ala Pro Leu His Leu Val Pro Leu Ile Glu Arg Leu Gly Thr
        1055                1060                1065

Pro Gln Gln Ile Ala Ile Ala Arg Glu Gly Asp Leu Leu Thr Lys
        1070                1075                1080

Glu Arg Leu Cys Cys Gly Leu Ser Met Phe Glu Val Ile Leu Thr
        1085                1090                1095

Arg Ile Arg Ser Phe Leu Asp Asp Pro Ile Trp Arg Gly Pro Leu
        1100                1105                1110

Pro Ser Asn Gly Val Met His Val Asp Glu Cys Val Glu Phe His
        1115                1120                1125

Arg Leu Trp Ser Ala Met Gln Phe Val Tyr Cys Ile Pro Val Gly
        1130                1135                1140
```

```
Thr His Glu Phe Thr Val Glu Gln Cys Phe Gly Asp Gly Leu His
    1145                1150                1155

Trp Ala Gly Cys Met Ile Ile Val Leu Leu Gly Gln Gln Arg Arg
    1160                1165                1170

Phe Ala Val Leu Asp Phe Cys Tyr His Leu Leu Lys Val Gln Lys
    1175                1180                1185

His Asp Gly Lys Asp Glu Ile Ile Lys Asn Val Pro Leu Lys Lys
    1190                1195                1200

Met Val Glu Arg Ile Arg Lys Phe Gln Ile Leu Asn Asp Glu Ile
    1205                1210                1215

Ile Thr Ile Leu Asp Lys Tyr Leu Lys Ser Gly Asp Gly Glu Gly
    1220                1225                1230

Thr Pro Val Glu His Val Arg Cys Phe Gln Pro Pro Ile His Gln
    1235                1240                1245

Ser Leu Ala Ser Ser
    1250

<210> SEQ ID NO 17
<211> LENGTH: 322
<212> TYPE: PRT
<213> ORGANISM: Homo sapiens

<400> SEQUENCE: 17

Met Ser Arg Ser Val Leu Gln Pro Ser Gln Lys Leu Ala Glu Lys
1               5                   10                  15

Leu Thr Ile Leu Asn Asp Arg Gly Val Gly Met Leu Thr Arg Leu Tyr
                20                  25                  30

Asn Ile Lys Lys Ala Cys Gly Asp Pro Lys Ala Lys Pro Ser Tyr Leu
                35                  40                  45

Ile Asp Lys Asn Leu Glu Ser Ala Val Lys Phe Ile Val Arg Lys Phe
50                  55                  60

Pro Ala Val Glu Thr Arg Asn Asn Asn Gln Gln Leu Ala Gln Leu Gln
65                  70                  75                  80

Lys Glu Lys Ser Glu Ile Leu Lys Asn Leu Ala Leu Tyr Tyr Phe Thr
                85                  90                  95

Phe Val Asp Val Met Glu Phe Lys Asp His Val Cys Glu Leu Leu Asn
                100                 105                 110

Thr Ile Asp Val Cys Gln Val Phe Phe Asp Ile Thr Val Asn Phe Asp
                115                 120                 125

Leu Thr Lys Asn Tyr Leu Asp Leu Ile Ile Thr Tyr Thr Thr Leu Met
                130                 135                 140

Ile Leu Leu Ser Arg Ile Glu Glu Arg Lys Ala Ile Ile Gly Leu Tyr
145                 150                 155                 160

Asn Tyr Ala His Glu Met Thr His Gly Ala Ser Asp Arg Glu Tyr Pro
                165                 170                 175

Arg Leu Gly Gln Met Ile Val Asp Tyr Glu Asn Pro Leu Lys Lys Met
                180                 185                 190

Met Glu Glu Phe Val Pro His Ser Lys Ser Leu Ser Asp Ala Leu Ile
                195                 200                 205

Ser Leu Gln Met Val Tyr Pro Arg Arg Asn Leu Ser Ala Asp Gln Trp
                210                 215                 220

Arg Asn Ala Gln Leu Leu Ser Leu Ile Ser Ala Pro Ser Thr Met Leu
225                 230                 235                 240

Asn Pro Ala Gln Ser Asp Thr Met Pro Cys Glu Tyr Leu Ser Leu Asp
                245                 250                 255
```

```
Ala Met Glu Lys Trp Ile Ile Phe Gly Phe Ile Leu Cys His Gly Ile
            260                 265                 270

Leu Asn Thr Asp Ala Thr Ala Leu Asn Leu Trp Lys Leu Ala Leu Gln
            275                 280                 285

Ser Ser Ser Cys Leu Ser Leu Phe Arg Asp Glu Val Phe His Ile His
            290                 295                 300

Lys Ala Ala Glu Asp Leu Phe Val Asn Ile Arg Gly Tyr Asn Lys Arg
305                 310                 315                 320

Ile Asn
```